(12) United States Patent
Bodor

(10) Patent No.: US 8,071,639 B2
(45) Date of Patent: Dec. 6, 2011

(54) SOFT ANTICHOLINERGIC ZWITTERIONS

(76) Inventor: Nicholas S. Bodor, Bal Harbour, FL (US)

( * ) Notice: Subject to any disclaimer, the term of this patent is extended or adjusted under 35 U.S.C. 154(b) by 119 days.

(21) Appl. No.: 12/418,939

(22) Filed: Apr. 6, 2009

(65) Prior Publication Data

US 2009/0257969 A1    Oct. 15, 2009

Related U.S. Application Data

(62) Division of application No. 12/137,896, filed on Jun. 12, 2008, now Pat. No. 7,538,219, which is a division of application No. 11/598,076, filed on Nov. 13, 2006, now Pat. No. 7,417,147.

(60) Provisional application No. 60/735,206, filed on Nov. 10, 2005.

(51) Int. Cl.
*A01N 43/36* (2006.01)
*C07D 207/00* (2006.01)

(52) U.S. Cl. ........................ 514/424; 548/556

(58) Field of Classification Search ........................ None
See application file for complete search history.

(56) References Cited

FOREIGN PATENT DOCUMENTS

| WO | 2005/000815 A2 | 1/2005 |
|---|---|---|
| WO | 2006/066928 A1 | 6/2006 |

OTHER PUBLICATIONS

Wu et al., Pharm. Res., 22, 2035-2044 (2005).*
Wu, Whei-Mei et al.: "Pharmacokinetic and Pharmacodynamic Evaluations of the Zwitterionic Metabolite of a New Series of N-Substituted Soft Anticholinergics", Pharmaceutical Research, vol. 22, No. 12, pp. 2035-2044 Dec. 12, 2005 (available online Sep. 26, 2005), Kluwer Academic/Plenum Publishers, USA.
Banholzer, Von R. et al.: "Synthesis of anticholinergically active N-alkylnorscopolamines and their quaternary salts with particular consideration of the bronchospasmolytic compound (−)-N-ethylnorscopolamine methobromide (Ba 253 BR)", Arzneimittel-Forschung, 35(1A), pp. 217-228, 1985, Editio Cantor, Germany.
Asthma, http://www.pamf.org/asthma/medications/inhaled/atrovent.html.
Bronchitis, http://www.chemocare.com/managing/bronchitis.asp.
Allergic Rhinitis, http://www.health.am/allergies/more/allergic_rhinitis.
Allergies-NonAllergic Vasomotor Rhinitis, http://allergies.about.com/od/noseandsinusallergies/a/pnar.htm.
Mydriasis, http://en.wikipedia.org/wiki/Mydriasis.
Herbison et al., BMJ vol. 326, 2003, 841-844.
Antiperspirant, http://www.medscape.com/viewarticle/427679_6.
International Search Report for PCT/US2006/043966.
Written Opinion of the International Searching Authority for PCT/US2006/043966.

* cited by examiner

*Primary Examiner* — Sun Jae Loewe
(74) *Attorney, Agent, or Firm* — Buchanan Ingersoll & Rooney PC

(57) ABSTRACT

Soft anticholinergic zwitterions of the formulas:

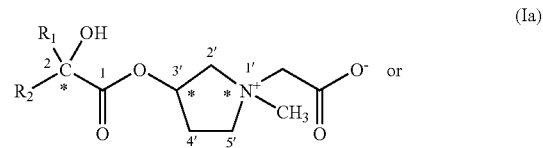

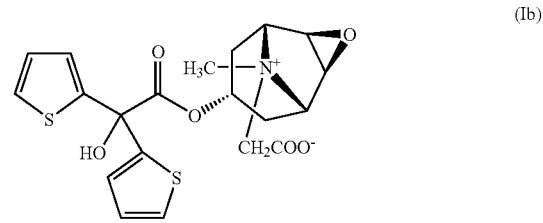

wherein $R_1$ and $R_2$ are both phenyl or one of $R_1$ and $R_2$ is phenyl and the other is cyclopentyl; and wherein each asterisk marks a chiral center; said compound having the R, S or RS stereoisomeric configuration at each chiral center unless specified otherwise, or being a mixture thereof.

6 Claims, 9 Drawing Sheets

| ATR | Atropine $10^{-8}$ (M) n = 6 |
| IPR | Ipratropium Br $10^{-8}$ (M) n = 6 |
| TIO | Tiotropium $7 \times 10^{-9}$ (M) n = 6 |
| Cpd (w) | Cpd (w) $3 \times 10^{-7}$ (M) n = 5 |
| Cpd (aa) | Cpd (aa) $3 \times 10^{-7}$ (M) n = 5 |
| Control | Vehicle treated preparations n = 10 |

ATR        Atropine $10^{-8}$ (M) n = 6
IPR        Ipratropium Br $10^{-8}$ (M) n = 6
TIO        Tiotropium $7 \times 10^{-9}$ (M) n = 6
Cpd (w)    Cpd (w) $3 \times 10^{-7}$ (M) n = 5
Cpd (aa)   Cpd (aa) $3 \times 10^{-7}$ (M) n = 5
Control    Vehicle treated preparations n = 10

SOFT ANTICHOLINERGIC ZWITTERIONS

CROSS-REFERENCE TO RELATED APPLICATIONS

This application is a divisional of U.S. application Ser. No. 12/137,896, filed Jun. 12, 2008, now U.S. Pat. No. 7,538,219, which is a divisional of U.S. application Ser. No. 11/598,076, filed Nov. 13, 2006, now U.S. Pat. No. 7,417,147, which claims benefit of U.S. Provisional Application No. 60/735,206, filed Nov. 10, 2005, all incorporated by reference herein in their entireties and relied upon.

This application is also related to U.S. application Ser. No. 11/598,079 now U.S. Pat. No. 7,399,861, said application concurrently filed with application Ser. No. 11/598,076 on Nov. 13, 2006, by the present inventor and claiming benefit of U.S. Provisional Application No. 60/735,207, filed Nov. 10, 2006, as well as U.S. application Ser. No. 12/138,013, filed Jun. 12, 2008, a divisional of application Ser. No. 11/598,079, filed concurrently herewith and claiming the same priority as its parent, said divisional now allowed, all incorporated by reference herein in their entireties and relied upon.

BACKGROUND

Various anticholinergic compounds have been previously described but are not optimal.

Muscarinic receptor antagonists are frequently used therapeutic agents that inhibit the effects of acetylcholine by blocking its binding to muscarinic cholinergic receptors at neuroeffector sites on smooth muscle, cardiac muscle, and gland cells as well as in peripherial ganglia and in the central nervous system (CNS). However, their side effects, which can include dry mouth, photophobia, blurred vision, urinary hesitancy and retention, decreased sweating, drowsiness, dizziness, restlessness, irritability, disorientation, hallucinations, tachycardia and cardiac arrhythmias, nausea, constipation, and severe allergic reactions, often limit their clinical use, and even topical anticholinergics can cause the same unwanted side effects. Glycopyrrolate and triotropium are among the quaternary ammonium anticholinergics, which have reduced CNS-related side effects as they cannot cross the blood-brain barrier; however, because glycopyrrolate (or, presumably, tiotropium) is eliminated mainly as unchanged drug or active metabolite in the urine, its administration is problematic in young or elderly patients and especially in uraemic patients. To increase the therapeutic index of anticholinergics, the soft drug approach has been applied in a number of different designs starting from various lead compounds over the past 20 years, but there is a need for yet other new soft anticholinergics. These novel muscarinic antagonists, just as all other soft drugs, are designed to elicit their intended pharmacological effect at the site of application, but they do not need to be further metabolized upon entering the systemic circulation and they are rapidly eliminated from the body, resulting in reduced systemic side effects and increased therapeutic index.

SUMMARY

New soft anticholinergic agents, pharmaceutical compositions containing them, processes for their preparation and methods for eliciting an anticholinergic response, especially for treating an inflammatory or obstructive disease of the respiratory tract or for treating overactive bladder, are provided.

In one exemplary embodiment, there is provided a compound having the formula

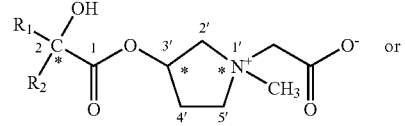

(Ia)

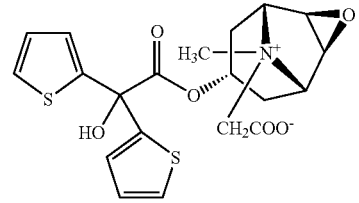

(Ib)

wherein $R_1$ and $R_2$ are both phenyl or one of $R_1$ and $R_2$ is phenyl and the other is cyclopentyl; and wherein each asterisk marks a chiral center; said compound having the R, S or RS stereoisomeric configuration at each chiral center unless otherwise specified, or being a mixture thereof.

In another exemplary embodiment there is provided a compound of the formula

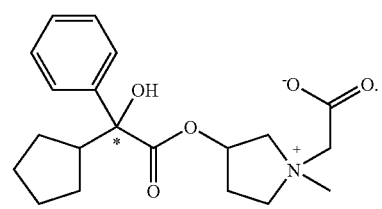

(Ia-i)

In another exemplary embodiment, there is provided a compound having the formula

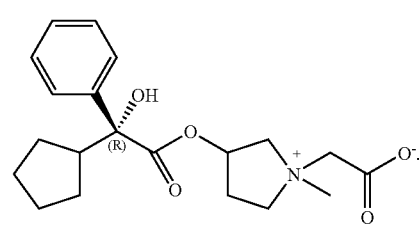

(Ia-ii)

In other exemplary embodiments, processes for preparing the compounds are provided.

In other exemplary embodiments, there are provided pharmaceutical compositions comprising one or more of the compounds of the foregoing formulas and pharmaceutically acceptable carriers therefor; pharmaceutical combinations comprising one or more of the compounds of the foregoing formulas and an anti-inflammatory corticosteroid, a betamimetic agent or an antiallergic agent; and methods of using the subject compositions and combinations.

DETAILED DESCRIPTION

Figure 1:
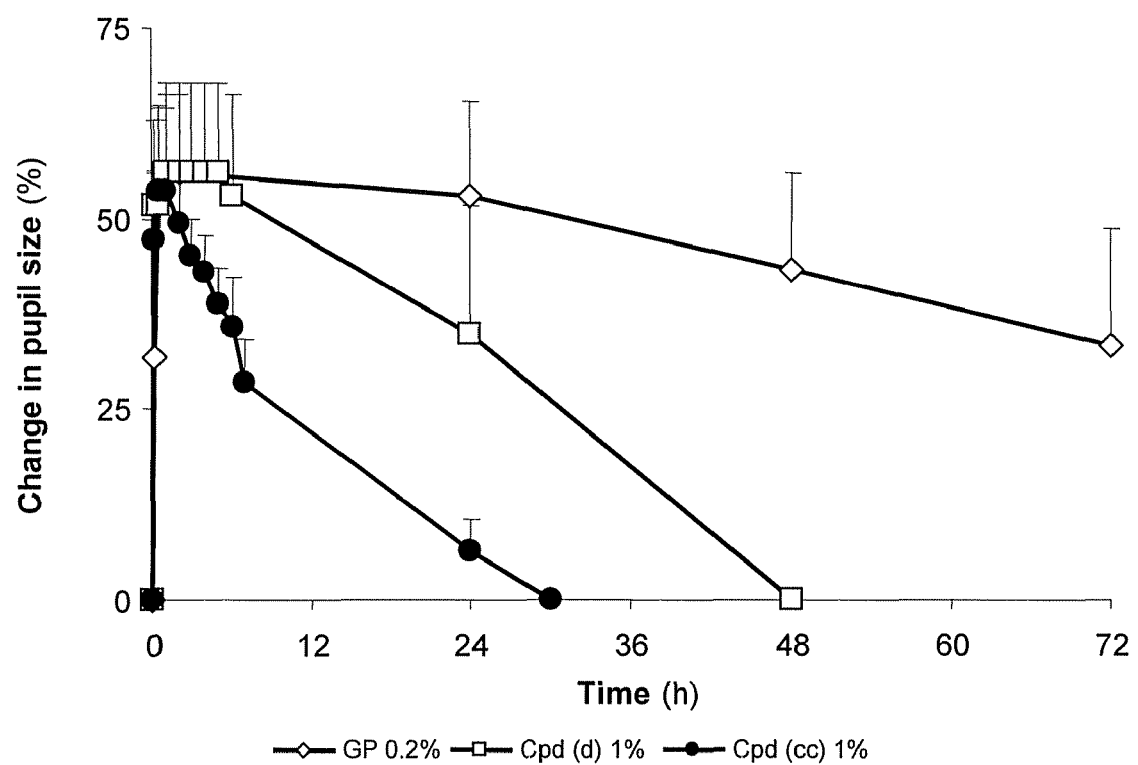
FIG. 1 is a graph showing mydriatic response (change in pupil size) with time after topical administration of zwitterion Compound (cc), its parent soft drug ester Compound (d) or glycopyrrolate in rabbits.

Throughout this specification, the following definitions, general statements and illustrations are applicable:

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compounds or compositions described herein, i.e., the process or composition is limited to the specified steps or materials and those which do not materially affect its basic and novel characteristics. The basic and novel features herein are the provision of compounds of formula (Ia) and (Ib) and combinations of those compounds with other drugs, particularly with antiinflammatory steroids, especially loteprednol etabonate or etiprednol dichloracetate, and most especially in the case of loteprenol etabonate (LE) further including an inactive metabolite enhancing agent for the LE as further defined hereinafter.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, $10^{th}$ Ed., McGraw Hill Companies Inc., New York (2001).

As used herein, "treating" means reducing, preventing, hindering or inhibiting the development of, controlling, alleviating and/or reversing the symptoms in the individual to which a combination or composition as described herein has been administered, as compared to the symptoms of an individual not being treated as described herein. A practitioner will appreciate that the combinations, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The methods described herein are intended for use with any subject/patient that may experience their benefits. Thus, in accordance herewith, the terms "subjects" as well as "patients," "individuals" and "warm-blooded animals" include humans as well as non-human subjects, particularly domesticated animals, particularly dogs, cats, horses and cows, as well as other farm animals, zoo animals and/or endangered species.

The compound of formula (Ib), which is of particular interest, can be named 6β,7β-epoxy-3β-hydroxy-8-carboxymethyl-8-methyl-1αH,5αH-tropanium, di-2-thienylglycolate inner salt and is also referred to herein as Compound (aa).

In formula (Ia), the compounds having the R configuration with respect to chiral center 2 are of particular interest.

In the compounds of formula (Ia), compounds wherein one of $R_1$ and $R_2$ is phenyl and the other is cyclopentyl are of particular interest.

Also of particular interest are the compounds of the formula:

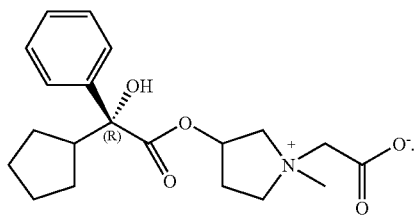

The following specific compounds of formula (Ia) are of particular interest:
(bb) (±) 3-(2-cyclopentyl-2-phenyl-2-hydroxyacetoxy)-1-(carboxymethyl)-1-methylpyrrolidinium inner salt;
(cc) (2R) 3-(2-cyclopentyl-2-phenyl-2-hydroxyacetoxy)-1-(carboxymethyl)-1-methylpyrrolidinium inner salt;
(dd) (2R, 1'R, 3'R) 3-(2-cyclopentyl-2-phenyl-2-hydroxyacetoxy)-1-(carboxymethyl)-1-methylpyrrolidinium inner salt;
(ee) (2R, 1'S, 3'R) 3-(2-cyclopentyl-2-phenyl-2-hydroxyacetoxy)-1-(carboxymethyl)-1-methylpyrrolidinium inner salt;
(ff) (2R, 1'R, 3'S) 3-(2-cyclopentyl-2-phenyl-2-hydroxyacetoxy)-1-(carboxymethyl)-1-methylpyrrolidinium inner salt;
(gg) (2R, 1'S, 3'S) 3-(2-cyclopentyl-2-phenyl-2-hydroxyacetoxy)-1-(carboxymethyl)-1-methylpyrrolidinium inner salt;
(hh) (2S,1'R,3'R) 3-(2-cyclopentyl-2-phenyl-2-hydroxyacetoxy)-1-(carboxymethyl)-1-methylpyrrolidinium inner salt;
(ii) (2S, 1'S, 3'R) 3-(2-cyclopentyl-2-phenyl-2-hydroxyacetoxy)-1-(carboxymethyl)-1-methylpyrrolidinium inner salt;
(jj) (2S, 1'R, 3'S) 3-(2-cyclopentyl-2-phenyl-2-hydroxyacetoxy)-1-(carboxymethyl)-1-methylpyrrolidinium inner salt; and
(kk) (2S, 1'S, 3'S) 3-(2-cyclopentyl-2-phenyl-2-hydroxyacetoxy)-1-(carboxymethyl)-1-methylpyrrolidinium inner salt.

Of these, particular mention may be made of:
(bb) (±) 3-(2-cyclopentyl-2-phenyl-2-hydroxyacetoxy)-1-(carboxymethyl)-1-methylpyrrolidinium inner salt; and
(cc) (2R) 3-(2-cyclopentyl-2-phenyl-2-hydroxyacetoxy)-1-(carboxymethyl)-1-methylpyrrolidinium inner salt.

Various methods of making the instant compounds are illustrated hereinafter. Generally speaking, the compounds of formula (Ia) can be prepared by hydrolysis of the corresponding esters of the formula

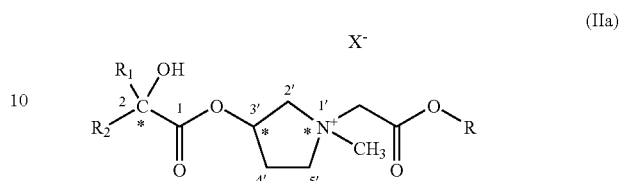

wherein $R_1$ and $R_2$, the asterisks and the stereoisomeric configurations are as defined above; R is $C_1$-$C_8$ alkyl, straight or branched chain; and $X^-$ is an anion with a single negative charge. The compounds of formula (IIa) are novel anticholinergic esters described and claimed in U.S. application Ser. No. 11/598,079, concurrently filed by the present inventor with parent application Ser. No. 11/598,076 and incorporated by reference herein in its entirety and relied upon. The compounds of formula (IIa) can be prepared by reacting a bromoacetate of the formula $$BrCH_2COOR$$

wherein R is as defined above, with a compound of the formula

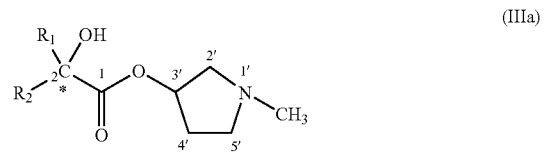

wherein $R_1$ and $R_2$, the asterisks and the stereoisomeric configurations are as defined above, and optionally separating the individual stereoisomers to afford a compound of formula (IIa) and, when desired, exchanging the bromine anion with a different $X^-$ anion wherein $X^-$ is as defined above but other than $Br^-$.

In a particular embodiment, the compound of formula (IIIa) has the R configuration with respect to chiral center 2.

In another particular embodiment, the compound of formula (IIIa) has the configuration R or S with respect to chiral center 1'. The compound of formula (IIIa) can also be made stereospecifically with respect to chiral center 3'.

In another embodiment, the process includes separating the individual stereoisomers of the compound of formula (Ia) after their formation to the extent possible.

In one particular embodiment, the process comprises preparing a compound of formula (Ia-i) or (Ia-ii) by hydrolyzing the corresponding methyl ester in aqueous sodium hydroxide solution.

In analogous fashion, methods of making the compound of formula (Ib) are illustrated hereinafter. Generally speaking, two alternate routes are proposed. One route comprises hydrolysis (for example, acid hydrolysis) of the corresponding esters of the formula

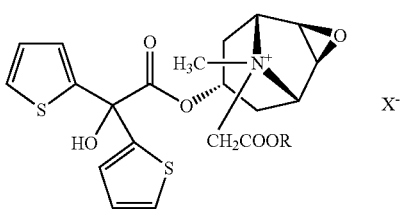

(IIb)

wherein the asterisks, stereoisomeric configuration, R and X⁻ are as defined above. The compounds of formula (IIb) are novel anticholinergic esters described and claimed in the U.S. application Ser. No. 11/598,079, concurrently filed by the present inventor with parent application Ser. No. 11/598,076, and incorporated by reference herein in its entirety and relied upon. The compounds of formula (IIb) can be prepared by reacting a bromoacetate of the formula:

BrCH₂COOR wherein R is as defined above, with a compound of the formula

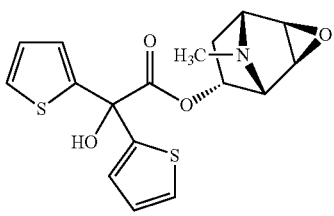

and optionally separating the individual stereoisomers to afford a compound of formula (IIb) and, when desired, exchanging the bromine anion with a different X⁻ anion wherein X⁻ is as defined above but other than Br⁻.

In an alternative route to the compound of formula (Ib), a scopine ester of the formula

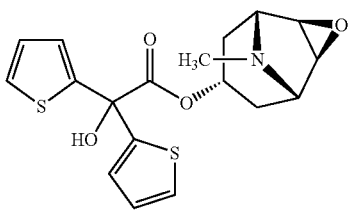

is reacted with trichloroethyl bromoacetate to afford the trichloroethyl ester

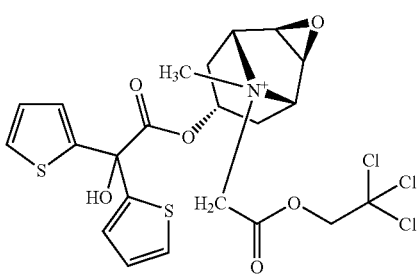

which is subjected to acid hydrolysis, using zinc dust and acetic acid, to afford the compound of formula (Ib).

The compounds of formulas (Ia) and (Ib) are of use as pharmaceutical agents because of their anticholinergic activity. An anticholinergically effective amount of such an agent inhibits the effect of acetycholine by blocking its binding to muscarinic cholinergic receptors at neuroeffector sites. Subjects in need of a method of eliciting an anticholinergic response are those suffering from conditions which respond to treatment with an anticholinergic agent. Such conditions include obstructive diseases of the respiratory tract, for example asthma and chronic obstructive pulmonary disease, vagally induced sinus bradycardia and heart rhythm disorders, spasms, for example in the gastrointestinal tract or urinary tract (including overactive bladder) and in menstrual disorders. The compounds of formulas (Ia) and (Ib) can also be used to induce short-acting mydriasis and thus can be used to dilate the pupils of the eyes in vision testing. Other uses of the compounds of formulas (Ia) and (Ib) include the treatment of ulcers as well as topical use as an antiperspirant in the treatment hyperhydrosis (sweating).

The compounds of formula (Ia) and (Ib) are particularly useful in the treatment of obstructive diseases of the respiratory tract. The expression "obstructive disease of the respiratory tract" includes breathing disorders such as asthma, bronchitis, chronic obstructive pulmonary disease (COPD), allergic rhinitis and infectious rhinitis.

"Asthma" refers to a chronic lung disease causing bronchoconstriction (narrowing of the airways) due to inflammation (swelling) and tightening of the muscles around the airways. The inflammation also causes an increase in mucus production, which causes coughing that may continue for extended periods. Asthma is generally characterized by recurrent episodes of breathlessness, wheezing, coughing, and chest tightness, termed exacerbations. The severity of exacerbations can range from mild to life threatening. The exacerbations can be a result of exposure to e.g. respiratory infections, dust, mold, pollen, cold air, exercise, stress, tobacco smoke, and air pollutants.

"COPD" refers to chronic obstructive pulmonary disease, primarily but not necessarily associated with past and present cigarette smoking. It involves airflow obstruction, mainly associated with emphysema and chronic bronchitis. Emphysema causes irreversible lung damage by weakening and breaking the air sacs within the lungs. Chronic bronchitis is an inflammatory disease, which increases mucus in the airways and bacterial infections in the bronchial tubes, resulting in obstructed airflow.

"Allergic rhinitis" refers to acute rhinitis or nasal rhinitis, including hay fever. It is caused by allergens such as pollen or dust. It may produce sneezing, congestion, runny nose, and itchiness in the nose, throat, eyes, and ears.

"Infectious rhinitis" refers to acute rhinitis or nasal rhinitis of infectious origin. It is caused by upper respiratory tract infection by infectious rhinoviruses, coronaviruses, influenza viruses, parainfluenza viruses, respiratory syncytical virus, adenoviruses, coxsackieviruses, echoviruses, or Group A beta-hemolytic Streptococci and is generically referred to as the common cold. It may produce sneezing, congestion, runny nose, and itchiness in the nose, throat, eyes, and ears.

The compounds of formula (Ia) and (Ib) are also particularly useful in the treatment of overactive bladder (OAB).

Overactive bladder is a treatable medical condition that is estimated to affect 17 to 20 million people in the United States. Symptoms of overactive bladder can include urinary frequency, urinary urgency, urinary urge incontinence (accidental loss of urine) due to a sudden and unstoppable need to urinate, nocturia (the disturbance of nighttime sleep because of the need to urinate) or enuresis resulting from overactivity of the detrusor muscle (the smooth muscle of the bladder which contracts and causes it to empty).

Neurogenic overactive bladder (or neurogenic bladder) is a type of overactive bladder which occurs as a result of detrusor muscle overactivity referred to as detrusor hyperreflexia, secondary to known neurologic disorders. Patients with neurologic disorders, such as stroke, Parkinson's disease, diabetes, multiple sclerosis, peripheral neuropathy, or spinal cord lesions often suffer from neurogenic overactive bladder. In contrast, non-neurogenic overactive bladder occurs as a result of detrusor muscle overactivity referred to as detrusor muscle instability. Detrusor muscle instability can arise from non-neurological abnormalities, such as bladder stones, muscle disease, urinary tract infection or drug side effects or can be idiopathic.

Due to the enormous complexity of micturition (the act of urination), an exact mechanism which causes overactive bladder is not known. Overactive bladder can result from hypersensitivity of sensory neurons of the urinary bladder, arising from various factors including inflammatory conditions, hormonal imbalances, and prostate hypertrophy. Destruction of the sensory nerve fibers, either from a crushing injury to the sacral region of the spinal cord, or from a disease that causes damage to the dorsal root fibers as they enter the spinal cord can also lead to overactive bladder. In addition, damage to the spinal cord or brain stem causing interruption of transmitted signals can lead to abnormalities in micturition. Therefore, both peripheral and central mechanisms can be involved in mediating the altered activity in overactive bladder.

Current treatments for overactive bladder include medication, diet modification, programs in bladder training, electrical stimulation, and surgery. Currently, antimuscarinics (which are members of the general class of anticholinergics) are the primary medication used for the treatment of overactive bladder. The antimuscarinic, oxybutynin, has been the mainstay of treatment for overactive bladder. However, treatment with known antimuscarinics suffers from limited efficacy and side effects such as dry mouth, dry eyes, dry vagina, blurred vision, cardiac side effects, such as palpitations and arrhythmia, drowsiness, urinary retention, weight gain, hypertension and constipation, which have proven difficult for some individuals to tolerate. Thus, the need for new anticholinergic agents is evident.

The compounds of formulas (Ia) and (Ib) are the zwitterion metabolites of the corresponding esters of formulas (IIa) and (IIb). While the compounds of formulas (Ia) and (Ib) are less active than the corresponding esters (by about an order of magnitude), the zwitterions are very rapidly eliminated from the systemic circulation mainly through urinary excretion in their unchanged form. This makes them particularly desirable for use in treating urinary tract disorders, especially overactive bladder. Moreover, their $M_3/M_2$ subtype selectively is greatly enhanced as compared to the parent esters, reducing the likelihood of cardiac side effects. The significantly reduced toxicity of the zwitterions also makes the zwitterions particularly desirable for long-term use, for example in the treatment of chronic conditions such as COPD or asthma.

The compounds of formula (Ia) or (Ib) may be used on their own or combined with other active substances of formula (Ia) or (Ib) according to the invention.

The compounds of formula (Ia) or (Ib) may optionally also be combined with other pharmacologically active substances. These include, in particular, betamimetics, antiallergic agents, and corticosteroids (also termed "anti-inflammatory steroids", "anti-inflammatory costicosteroids" or simply "steroids") and combinations of these active substances. The combinations with betaminetics, antiallergics or corticosteroids are of interest in the treatment of obstructive diseases of the respiratory tract, especially COPD or asthma. Accordingly, they are intended for administration by oral inhalation as powders or aerosols.

Examples of betamimetics which may be used in conjunction with the compounds of formula (Ia) or (Ib) include compounds selected from the group consisting of bambuterol, bitolterol, carbuterol, clenbuterol, fenoterol, formoterol, hexoprenaline, ibuterol, pirbuterol, procaterol, reproterol, salmeterol, sulfphonterol, terbutaline, tulobuterol, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)ethanol, optionally in the form of their racemates, their enantiomers, their diastereomers, as well as optionally their pharmacologically acceptable acid addition salts and hydrates. It is particularly preferable to use, as betamimetics, active substances of this kind, combined with the compounds of formula (Ia) or (Ib), selected from among fenoterol, formoterol, salmeterol, 1-[3-(4-methoxybenzylamino)-4-hydroxyphenyl]-2-[4-(1benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of their racemates, their enantiomers, their diastereomers, as well as optionally their pharmacologically acceptable acid addition salts and hydrates. Of the betamimetics mentioned above, the compounds formoterol and salmeterol, optionally in the form of their racemates, their enantiomers, their diastereomers, as well as optionally their pharmacologically acceptable acid addition salts and hydrates, are particularly important.

The acid addition salts of the betamimetics selected from among the hydrochloride, hydrobromide, sulfate, phosphate, fumarate, methanesulfonate and xinafoate are preferred. In the case of salmeterol, the salts selected from among the hydrochloride, sulfate and xinafoate are particularly preferred, especially the sulfates and xinafoates. In the case of formoterol, the salts selected from among the hydrochloride, sulfate and fumarate are particularly preferred, especially the hydrochloride and fumarate. Of outstanding importance is formoterol fumarate.

The corticosteroids which may optionally be used in conjunction with the compounds of formula (Ia) or (Ib), include compounds selected from among flunisolide, beclomethasone, triamcinolone, budesonide, fluticasone, mometasone, ciclesonide, rofleponide, GW 215864, KSR 592, ST-126, loteprednol etabonate, etiprednol dichloracetate and dexamethasone. The preferred corticosteroids are those selected from among flunisolide, beclomethasone, triamcinolone, loteprednol etabonate, etiprednol dichloracetate, budesonide, fluticasone, mometasone, ciclesonide and dexamethasone, while budesonide, fluticasone, loteprednol etabonate, etiprednol dichloracetate, mometasone and ciclesonide, especially budesonide, fluticasone, loteprednol etabonate and etiprednol dichloracetate, are of particular importance. Any reference to steroids herein also includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates or furoates. The corticosteroids may optionally also be in the form of their hydrates.

When the corticosteroid is loteprednol etabonate, it may be advantageously combined with an enhancing agent selected from the group consisting of:
(a) 11β,17α-dihydroxyandrost-4-en-3-one-17β-carboxylic acid (cortienic acid, or CA);
(b) 11β,17α-dihydroxyandrosta-1,4-dien-3-one-17β-carboxylic acid ($\Delta^1$ cortienic acid or $\Delta^1$-CA);
(c) methyl 11β,17α-dihydroxyandrost-4-en-3-one-17β-carboxylate (cortienic acid methyl ester, or MeCA);
(d) ethyl 11β,17α-dihydroxyandrost-4-en-3-one-17β-carboxylate (cortienic acid ethyl ester, or EtCA);
(e) methyl 11β,17α-dihydroxyandrosta-1,4-dien-3-one-17β-carboxylate (($\Delta^1$ cortienic acid methyl ester, or $\Delta^1$-MeCA); and
(f) ethyl 11β,17α-dihydroxyandrosta-1,4-dien-3-one-17β-carboxylate ($\Delta^1$ cortienic acid ethyl ester, or $\Delta^1$-EtCA),
wherein the mole ratio of loteprednol etabonate to enhancing agent is from about 5:1 to about 0.5:1. Such combinations with these inactive metabolites are described in detail in WO 2005/000317 A1, incorporated by reference herein in its entirety and relied upon.

Examples of antiallergic agents which may be used as a combination with the compounds of formula (Ia) or (Ib) include epinastin, cetirizin, azelastin, fexofenadin, levocabastin, loratadine, mizolastin, ketotifen, emedastin, dimetinden, clemastine, bamipin, cexchlorpheniramine, pheniramine, doxylamine, chlorophenoxamine, dimenhydrinate, diphenhydramine, promethazine, ebastin, desloratidine and meclizine. Preferred antiallergic agents which may be used in combination with the compounds of formula (Ia) or (Ib) are selected from among epinastin, cetirizin, azelastin, fexofenadin, levocabastin, loratadine, ebastin, desloratidine and mizolastin, epinastin and desloratidine being particularly preferred. Any reference to the abovementioned antiallergic agents also includes a reference to any pharmacologically acceptable acid addition salts thereof which may exist.

When the compounds of formula (Ia) or (Ib) are used in conjunction with other active substances, the combination with steroids or betamimetics is particularly preferred of the various categories of compounds mentioned above.

Whether or not the compounds of formula (Ia) or (Ib) are used in conjunction with other active substances as described above, they are typically administered in the form of a pharmaceutical composition comprising an anticholinergically effective amount of a compound of formula (Ia) or (Ib) and a non-toxic pharmaceutically acceptable carrier therefor. Pharmaceutically acceptable carriers, or diluents, are well-known in the art. The carriers may be any inert material, organic or inorganic, suitable for administration, such as: water, gelatin, gum arabic, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, as noted above, and/or conventional additives such as stabilizers, wetting agents, emulsifiers, flavoring agents, buffers, binders, disintegrants, lubricants, glidants, antiadherents, propellants, and the like. The carrier, e.g., non-active ingredient, can be just (sterile) water with the pH adjusted to where the active pharmaceutical agent is very soluble. It is preferred that the pH be at or near 7. Alternatively and preferably, the non-active carrier agent should be physiological saline with the pH adjusted appropriately.

The novel compounds of formula (Ia) or (Ib) can be administered in any suitable way. The compounds can be made up in solid or liquid form, such as tablets, capsules, powders, syrups, elixirs and the like, aerosols, sterile solutions, suspensions or emulsions, and the like.

The compounds of formula (Ia) or (Ib) can be brought into suitable dosage forms, such as compositions for administration through the oral, rectal, transdermal, parenteral, nasal, pulmonary (typically via oral inhalation) or topical (including ophthalmic) route in accordance with accepted pharmaceutical procedures. The route of administration and thus the dosage form will be chosen in light of the condition to be treated with the instant anticholinergic agents. By way of illustration only, when the compound of formula (Ia) or (Ib) is administered to treat COPD or asthma, of other serious obstructive disease of the respiratory tract, the compounds may be advantageously administered via inhalation or insufflation; for such purposes, the compounds are advantageously in the form of an aerosol or a powder for inhalation. When administered to treat less serious respiratory disorders such as rhinitis, a nasal spray, mist or gel may be advantageous. For inducing mydriasis, an ophthalmic formulation such as eye drops may be most appropriate. For OAB, a formulation for oral administration such as tablet or capsules or a transdermal preparation may be preferred. For treating hyperhydrosis, an topical preparation formulated as an antiperspirant stick, gel, spray, cream or the like would be preferred.

For purposes of illustration, dosages are expressed based on the inhalation of an aerosol solution, such as the product Atrovent Inhalation Aerosol (Boehringer Ingelheim). Adjustments in dosages for administration by other modes of inhaled administration are well known to those skilled in the art.

In general, a therapeutically effective amount of compound of formula (Ia) or (Ib) is from about 4 μg to about 1,000 μg, e.g., from about 30 μg to about 1,000 μg or from about 200 μg to about 1000 μg. However, the exact dosage of the specific compound of formula (Ia) or (Ib) will vary depending on its potency, the mode of administration, the age and weight of the subject and the severity of the condition to be treated. The daily dosage may, for example, range from about 0.03 μg to about 40 μg per kg of body weight, administered singly or multiply in doses e.g. from about 3 μg to about 4,000 μg each. The compounds of formula (Ia) or (Ib) can be administered from one to four times daily, e.g., once or twice daily.

The dosage form for inhalation can be an aerosol. The minimum amount of an aerosol delivery is about 0.2 ml and the maximum aerosol delivery is about 5 ml. The concentration of the compounds of formula (Ia) or (Ib) may vary as long as the total amount of spray delivered is within the about 0.2 to about 5 ml amount and as long as it delivers an anticholinergically effective amount of the compound of formula (Ia) or (Ib). It is well known to those skilled in the art that if the concentration is higher, one gives a smaller dose to deliver the same effective amount.

The dosage form for inhalation can also be via intranasal spray. The minimum amount of an aerosol delivery is about 0.02 ml per nostril and the maximum aerosol delivery is about 0.2 ml per nostril. The concentration of the compounds of formula (Ia) or (Ib) may vary as long as the total amount of spray delivered is within about 0.02 ml per nostril to about 0.2 ml per nostril, e.g., between about 0.05 ml per nostril and about 0.08 ml per nostril, and it delivers an anticholinergically effective amount of the compound of formula (Ia) or (Ib).

Of course, the volume of aerosol or intranasal spray for delivering an anticholinergically effective amount of the compound of formula (Ia) or (Ib) depends upon the concentration of the compound in the aerosol or intranasal spray, i.e., higher concentrations of the compound of formula (Ia) or (Ib) require smaller dosage volumes to deliver a therapeutically effective amount and lower concentrations of the compound of formula (Ia) or (Ib) require larger dosage volumes to deliver the same anticholinergically effective amount.

Aerosols for inhalation of various pharmaceutical agents are well known to those skilled in the art, including many aerosols for treating asthma. Aerosols may be produced with a nebulizer. Typically, the nebulizer is charged with a carrier solution and the compound of formula (Ia) or (Ib) in an amount sufficient to effectively deliver an anticholinergically effective amount of the compound of formula (Ia) or (Ib). For instance, depending upon the nebulizer and its operating conditions, the nebulizer may be charged with several hundred mg of anticholinergic compound in order to deliver about 4 μg to about 1000 μg, e.g., from about 30 μg to about 1000 μg or from about 150 μg to about 800 μg, of the compound of formula (Ia) or (Ib).

The dosage form for inhalation may also be in powder form. Powders for inhalation of various pharmaceutical agents are well known to those skilled in the art, including many powders for treating asthma. When the dosage form is a powder, the compounds of formula (Ia) or (Ib) can be administered in pure form or diluted with an inert carrier. When an inert carrier is used, the compounds are compounded such that the total amount of powder delivered delivers an "effective amount" of the compounds according to the invention. The actual concentration of the active compound may vary. If the concentration is lower, then more powder must be delivered, if the concentration is higher, less total material must be delivered to provide an effective amount of the active compound according to the invention. Any of the foregoing pharmaceutical compositions may further comprise one or more additional active substances, particularly corticosteroids and/or betamimetics as discussed earlier.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Suitable preparations for administering the compounds of formula (Ia) or (Ib) include tablets, capsules, suppositories, solutions, etc. Of particular importance (particularly when treating asthma or COPD or other respiratory disorders) is the administration of the compounds by inhalation. The proportion of pharmaceutically active compound or compounds should be in the range from 0.05 to 90% by weight, preferably 0.1 to 50% by weight of the total composition. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatin, lubricants such as magnesium stearate or talc and/or agents for delaying release, such as carboxymethyl cellulose, cellulose acetate phthalate, or polyvinyl acetate. The tablets may also comprise several layers. Tablets and other solid oral formulations are of particular interest in the treatment of OAB or ulcers while opthalmic solutions, suspensions and gels are of special interest for inducing mydriasis and topical gels, solids and sprays are of particular use as antiperspirants.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances of formulas (Ia) or (Ib) or combinations thereof as described above may additionally contain a sweetener such as saccharin, cyclamate, aspartame, sucralose, glycerol or sugar and a flavor enhancer, e.g. a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates, or stabilizers such as alkali metal salts of ethylenediamine tetraacetic acid, optionally using emulsifiers and/or dispersants, while if water is used as the diluent, for example, organic solvents may optionally be used as solvating agents or dissolving aids, and transferred into injection vials or ampules or infusion bottles.

Capsules containing one or more active substances or combinations of active substances may for example be prepared by mixing the active substances with inert carriers such as lactose or sorbitol and packing them into gelatin capsules. Suitable suppositories may be made for example by mixing with carriers provided for this purpose, such as neutral fats or polyethyleneglycol or the derivatives thereof. Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulfite liquors, methylcellulose, starch and polyvinylpyrrolidone) and lubricants (e.g. magnesium stearate, talc, stearic acid and sodium lauryl sulphate).

The preparations are administered by the usual methods, preferably by inhalation in the treatment of asthma or COPD or other respiratory disorders. For oral administration the tablets may, of course, contain, apart from the above-mentioned carriers, additives such as sodium citrate, calcium carbonate and dicalcium phosphate together with various additives such as starch, preferably potato starch, gelatin and the like. Moreover, lubricants such as magnesium stearate, sodium lauryl sulfate and talc may be used at the same time for the tabletting process. In the case of aqueous suspensions the active substances may be combined with various flavor enhancers or colorings in addition to the excipients mentioned above.

The dosage of the compounds of formula (Ia) and (Ib) is naturally greatly dependent on the route of administration and the complaint to be treated. When administered by inhalation the compounds of formula (Ia) or (Ib) are characterized by high efficacy even at doses in the µg range. The compounds of formula (Ia) or (Ib) can also be used effectively above the µg range. The dosage may then be in the gram range, for example. Particularly when administered by a method other than inhalation, the compounds according to the invention may be given in higher doses (in the range from 3 to 1000 mg, for example, although this does not imply any limitation).

The compounds of formula (Ia) and (Ib), combinations of a compound of formula (Ia) or (Ib) with one or more other active agents, and compositions comprising a compound of formula (Ia) or (Ib), with or without one or more other active agents, as described hereinabove are thus useful in a method for eliciting an anticholinergic response in a subject in need of same, comprising administering to said subject an anticholinergically effective amount of said compound or composition. In particular embodiments, the method is for treating an obstructive disease of the respiratory tract, especially when the disease is chronic obstructive pulmonary disease or asthma, or for treating overactive bladder. In another embodiment, the method comprises inducing mydriasis in the eye(s) of a subject in need of such treatment, comprising topically applying to the eye(s) of said subject a mydriatically effective amount of a compound of formula (Ia) or (Ib) or combination or composition comprising it as described hereinabove. Use of compounds of formula (Ia) or (Ib) in the preparation of a medicament for treating a condition responsive to an anticholinergic agent (such as any of these conditions disclosed above) is likewise provided herein.

In particular embodiments there are provided combinations of the compound of formula (Ia) or (Ib) with other active agents, especially one or more antiinflammatory corticosteroids, betamimetic agents or antiallergic agents. In the combination products, the active agents are present in a combined amount effective to treat the target condition, especially to treat an obstructive disease of the respiratory tract, most especially to treat chronic obstructive pulmonary disease or asthma. In preferred embodiments, the other active agent is a betamimetic agent or an antiinflammatory corticosteroid. Of particular interest are combinations of a compound of formula (Ia) or (Ib) and a corticosteroid, especially loteprednol etabonate or etiprednol dichloracetate. When loteprednol etabonate is selected as the corticosteroid, its activity can be enhanced by combination with cortienic acid or $\Delta^1$-cortienic acid or a methyl or ethyl ester of cortienic acid or $\Delta^1$-cortienic acid, in a mole ratio of from about 5:1 to about 0.5:1. A molar ratio of about 1:1, which can be approximated by a 1:1 ratio by weight, is particularly convenient.

Initial Studies
Purpose

Evaluation of the zwitterionic common metabolite of a novel series of N-substituted soft analogs of glycopyrrolate both as racemates and as 2R isomers.

Methods

Activities have been assessed using both in vitro (receptor-binding assay, guinea pig ileum $pA_2$-assay) and in vivo techniques (rabbit mydriatic response, rat cardiac effects). Pharmacokinetic characterizations in rats also have been performed.

Results

The metabolite was highly water-soluble and very stable in buffer solutions as well as in rat biological media. Following i.v. administration in rats, it was very rapidly eliminated, mainly through renal excretion with a half-life of about 10 min. Receptor-binding and guinea pig ileum assays indicated this metabolite as more than an order of magnitude less active than its parent soft drugs or glycopyrrolate. Moderate $M_3/M_2$ muscarinic-receptor subtype-selectivity was observed, further reducing the likelihood of cardiac side-effects. The metabolite showed some mydriatic effect and some protecting effect against carbachol-induced bradycardia, but of much shorter durations than glycopyrrolate, and it had no effect on resting heart rate.

Conclusions

N-substituted zwitterionic metabolites retain some, but reduced activity of their parent quaternary ammonium-ester soft anticholinergic drugs, and they are very rapidly eliminated from the systemic circulation.

A recently developed series of N-substituted soft glycopyrrolate anticholinergics [exemplified below and represented by formula (IIa) hereinabove] have a zwitterionic metabolite in which the positive quaternary nitrogen and the negative acid moiety formed by hydrolysis are spatially very close, and, hence, the overall electron distribution is somewhat similar to that of the neutral compound, which is active. Therefore, because this metabolite might still retain some activity, a detailed investigation of its pharmacokinetic and pharmacodynamics (PK/PD) was undertaken to ensure that the corresponding N-substituted soft anticholinergics still can be considered as undergoing a facile, essentially one-step metabolic deactivation as required by the principles of soft drug design. Because stereospecificity is known to affect pharmacological activity at muscarinic receptors, in addition to the racemic metabolite, (±) 3-(2-cyclopentyl-2-phenyl-2-hydroxyacetoxy)-1-(carboxymethyl)-1-methylpyrrolidinium inner salt, the corresponding 2R isomer has also been prepared and examined.

Receptor binding affinity is a major determinant of drug activity. For muscarinic receptors, five subtypes, $M_1$-$M_5$, have been found and cloned from human tissue, and there is sufficient correlation among these molecular subtypes and pharmacological subtypes to warrant use of a unified $M_1$-$M_5$ notation. Subtype selectivity (e.g., $M_3/M_2$) could be useful in eliminating many potential side effects, but most currently used anticholinergics show no subtype selectivity; a few newer ones that show muscarinic receptor subtype selectivity are being pursued for development. For soft anticholinergics, such subtype selectivity could also further enhance their therapeutic advantage by further decreasing their side effects.

In the present study, chemical and biological stabilities have been evaluated in vitro in aqueous solutions and in rat blood, plasma, and lung and liver homogenates. In vitro anticholinergic activities were characterized through $M_1$-$M_4$ receptor binding affinities ($pK_i$), and through guinea pig ileum assay $pA_2$ values. In vivo pharmacological activities were evaluated through mydriatic effects in rabbits and cardiac effects in rats. Pharmacokinetics after i.v. administration in rats has also been evaluated.

Material and Methods
Materials

Glycopyrrolate (glycopyrronium bromide) was kindly provided by Boehringer Ingelheim Chemicals, Inc. Carbamylcholine bromide (carbachol), atropine methylbromide (atropine MeBr), and scopolamine methylbromide (scopolamine MeBr) were obtained from Sigma Chemicals Co. (St. Louis, Mo.); tropicamide (1%) was obtained from Bausch & Lomb Pharmaceutical (Tampa, Fla.). N-[$^3$H]-Methyl-scopolamine (NMS) was obtained from Amersham Biosciences UK Limited (Buckinghamshire, UK). Cloned human muscarinic receptor subtypes $M_1$-$M_4$ were obtained from Applied Cell Science Inc. (Rockville, Md.). Scintiverse BD was from Fisher Scientific Co. (Pittsburgh, Pa.). Animal studies were conducted in accordance with the Guide for the Care and Use of Laboratory Animals adopted by the National Institute of Health. Institutional animal care and use committee (IACUC) approval was obtained prior to the initiation of this research and during its execution.

Synthesis

Racemic Cyclopentylmandelic Acid (1)

Cyclopentylmagnesium bromide ether solution (100 ml, 2M; 0.2 mol) was added drop-wise to benzoylformic acid (15 g, 0.1 mol) in 330 ml of anhydrous ethyl ether at 0° C. The mixture was stirred at 0° C. for 30 min and at room temperature for 24 h. The reaction mixture was treated with 1 N HCl, and the aqueous solution was extracted with ether. The combined ether solution was treated with $K_2CO_3$ solution. The potassium carbonate solution was acidified with HCl and extracted with ether twice. The ether solution was dried with anhydrous sodium sulfate and evaporated to give a crude product. The crude product was washed with water to get pure racemic cyclopentylmandelic acid 1 (8.0 g, 36.4%). Needle-like crystals, m.p.: 153-154° C. $^1$H NMR (CDCl$_3$, 500 MHz): 1.28-1.39, 1.42-1.50, 1.51-1.61, 1.63-1.72 [8H, m, (CH$_2$)$_4$], 2.93 [1H, p, CHC(OH)], 7.26-7.30, 7.33-7.36, 7.65-7.67 (5H, m, Ph) ppm.

Methyl Cyclopentylmandelate (2)

To a mixture of racemic cyclopentylmandelic acid R/S(±)1 (4.47 g, 20 mmol) and potassium carbonate (7.01 g, 50 mmol) in DMF (50 ml), methyl iodide (8.64 g, 60 mmol) was added at room temperature. The mixture was stirred at room temperature for 2 h, and then poured into water and extracted with hexanes three times. Evaporation of the dried hexanes extract gave a crude product. Flash chromatography of the crude product on silica gel with 1.5:1 hexanes:methylene chloride gave the pure product 2 (3.02 g, 64%). $^1$H NMR (CDCl$_3$, 300 MHz): 1.32-1.37, 1.43-1.69 [8H, m, (CH$_2$)$_4$], 2.90 [1H, p, CHC(OH)], 3.74 (1H, s, OH), 3.77 (3H, s, CH$_3$), 7.25-7.37, 7.63-7.65 (5H, m, Ph) ppm.

N-Methyl-3-pyrrolidinyl Cyclopentylmandelate (4)

A solution of 2 (2.20 g, 9.4 mmol) and N-methyl-3-pyrrolidinol (3, 1.30 g, 13 mmol) in 40 ml of n-heptane was heated until 20 ml of heptane had been distilled. About 0.003 g of sodium was added, and the solution was stirred and heated for 2 h as the distillation was continued. More heptane was added at such a rate as to keep the reaction volume constant. Additional sodium was added at the end of an hour. The solution was then cooled and extracted with 3N HCl. The acid extract was made alkaline with concentrated NaOH and extracted three times with ether. Removal of the dried ether solution gave a crude oil. Flash chromatography of the crude product on silica gel with 8:1 EtOAc:EtOH gave pure product 4 (2.053 g, 72%). Analysis for $C_{18}H_{25}NO_3$. Calcd: C, 71.26; H, 8.31; N, 4.62. Found: C, 71.55; H, 8.44; N, 4.68. $^1$H NMR (CDCl$_3$, 500 MHz): 1.27-1.35, 1.40-1.47, 1.54-1.60, 1.75-1.90 [8H, m, (CH$_2$)$_4$], 2.12-2.30, 2.52-2.57, 2.64-2.81 (6H, m CH$_2$NCH$_2$CH$_2$), 2.33, 2.36 (3H, 2s, NCH$_3$), 2.93 [(1H, p, CHC(OH)], 3.83 (1H, bs, OH), 5.23 (1H, m, CO$_2$CH), 7.23-7.36, 7.64-7.67 (5H, m, Ph) ppm.

3-(2-Cyclopentyl-2-phenyl-2-hydroxyacetoxy)-1-(methoxycarbonylmethyl)-1-methylpyrrolidinium Bromide, Compound (a)

To compound 4 (0.8235 g, 2.71 mmol) in 30 ml of dry acetonitrile, methyl bromoacetate (1.08 g, 7.06 mmol) was added at room temperature. The mixture was stirred for 2 h. Evaporation of acetonitrile gave a crude product. The crude product was dissolved in a small volume of methylene chloride and then poured into 100 ml of dry ethyl ether to precipitate. This procedure was repeated three times to obtain Compound (a) as pure product (0.9912 g, 80%). White powder, m.p.: 192-194° C. Analysis for $C_{21}H_{30}BrNO_5$. Calcd: C, 55.27; H, 6.63; N, 3.07. Found: C, 55.11; H, 6.59; N, 3.03. $^1$H NMR (CDCl$_3$, 500 MHz): 1.23-1.29, 1.31-1.37, 1.41-1.47, 1.53-1.67 [8H, m, (CH$_2$)$_4$], 2.18-2.23, 2.73-2.80, 4.04-4.16, 4.21-4.25 (6H, m, CH$_2$NCH$_2$CH$_2$), 2.85 [1H, p, CHC(OH)], 3.57 (3H, s, NCH$_3$), 3.80 (3H, s, CO$_2$CH$_3$), 4.66, 4.85 (2H, 2dd, CH$_2$CO$_2$), 5.27 (1H, s, OH), 5.52 (1H, m, CO$_2$CH), 7.25-7.28, 7.32-7.35, 7.57-7.59 (5H, m, Ph) ppm.

3-(2-Cyclopentyl-2-phenyl-2-hydroxyacetoxy)-1-(ethoxycarbonylmethyl)-1-methylpyrrolidinium Bromide, Compound (b)

To compound 4 (0.369 g, 1.22 mmol) in 10 ml of dry acetonitrile, ethyl bromoacetate (0.377 g, 2.25 mmol) was added at room temperature. The mixture was stirred for 2 h. Evaporation of acetonitrile gave a crude product. The crude product was dissolved in a small volume of ethylene chloride and then poured into 50 ml of dry ethyl ether to precipitate. This procedure was repeated three times to obtain Compound (b) as pure product (0.45 g, 79%). White powder, m.p.: 192-194° C.

Analysis for $C_{22}H_{32}BrNO_5$. Calcd: C, 56.17; H, 6.86; N, 2.98. Found: C, 56.14; H, 6.89; N, 2.94. $^1$H NMR (CDCl$_3$, 500 MHz): 1.35 (3H, t, CH$_3$CH$_2$), 1.26-1.33, 1.42-1.47, 1.55-1.67 [8H, m, (CH$_2$)$_4$], 2.14-2.21, 2.73-2.79, 4.12-4.17, 4.22-4.29 (6H, m, CH$_2$NCH$_2$CH$_2$), 2.86 [1H, p, CHC(OH)], 3.62 (3H, s, NCH$_3$), 4.25 (2H, q, CH$_3$CH$_2$), 4.67, 4.83 (2H, dd, CH$_2$CO$_2$), 4.91 (1H, s, OH), 5.53 (1H, m, CO$_2$CH), 7.25-7.27, 7.32-7.34, 7.57-7.59 (5H, m, Ph) ppm.

Resolution of Racemic Cyclopentylmandelic Acid (1)

(–)-Strychnine (6.10 g) in 50 ml of methanol (suspension) was added to racemic cyclopentylmandelic acid 1, (3.96 g) in methanol (20 ml) at room temperature. The reaction solution was let to stand for overnight. The crystals were removed by filtration and crystallized again with hot methanol. The second crop of crystals was collected by filtration and treated with sodium hydroxide solution. The basic solution was extracted with methylene chloride twice (methylene chloride solution discarded), and then acidified with hydrochloric acid to recover the resolved cyclopentylmandelic acid. To this resolved acid (20.6 mg in 0.1 ml of ethyl acetate), 13 µL of (+)-α-phenylethylamine was added. The precipitate which formed was washed with hexane three times and dried under vacuum. The precipitate was identified by NMR as optically pure cyclopentylmandelic acid, R(–)1, (1.49 g, 37.6%). M.p.: 121-122° C. $[\alpha]^{25°}_D = -22.5°$ (c=1 g/100 ml, CHCl$_3$). $^1$H NMR (CDCl$_3$, 500 MHz): 1.28-1.39, 1.42-1.50, 1.51-1.61, 1.64-1.73 [8H, m, (CH$_2$)$_4$], 2.93 [1H, p, CHC(OH)], 7.25-7.28, 7.32-7.35, 7.64-7.65 (5H, m, Ph) ppm.

Methyl(–)-cyclopentylmandelate, R(–)2

To a mixture of (–)-cyclopentylmandelic acid, R(–)1, (1.83 g, 8.3 mmol) and potassium carbonate (2.87 g, 21 mmol) in DMF (21 ml), methyl iodide (3.53 g, 25 mmol) was added at room temperature. The mixture was stirred at room temperature for 2 h, and then poured into water and extracted with hexanes three times. Evaporation of the dried hexanes extract gave a crude product. Flash chromatography of the crude product on silica gel with 1.5:1 hexanes:methylene chloride gave pure product R(−)2 (1.95 g, 100%). Analysis for $C_{18}H_{18}O_3$. Calcd: C, 71.77; H, 7.74. Found: C, 71.88; H, 7.80. $^1$H NMR (CDCl$_3$, 500 MHz): 1.32-1.36, 1.43-1.61 [8H, m, (CH$_2$)$_4$], 2.90 [1H, p, CHC(OH)], 3.71 (1H, s, OH), 3.79 (3H, s, CH$_3$), 7.25-7.28, 7.31-7.35, 7.63-7.65 (5H, m, Ph) ppm.

N-Methyl-3-pyrrolidinyl(−)-cyclopentylmandelate, 2R-4

A solution of R(−)2 (1.85 g, 7.9 mmol) and N-methyl-3-pyrrolidinol (3, 1.05 g, 10.4 mmol) in 40 ml of n-heptane was heated until 20 ml of heptane had distilled. Approximately 0.003 g of sodium was added, and the solution was stirred and heated for 2 h as the distillation was continued. More heptane was added at such a rate as to keep the reaction volume constant. Additional sodium was added at the end of an hour. The solution was then cooled and extracted with 3N HCl. The acid extract was made alkaline with concentrated NaOH and extracted three times with ether. Removal of dried ether solution gave a crude oil. Flash chromatography of the crude product on silica gel with 8:1 EtOAc:EtOH gave 2R-4 as a mixture of two diastereoisomers in an NMR-estimated ratio of 1:1, (1.68 g, 70%). Analysis for $C_{18}H_{25}NO_3.0.2H_2O$. Calcd: C, 70.42; H, 8.34; N, 4.5. Found: C, 70.60; H, 8.26; N, 4.63. $^1$H NMR (CDCl$_3$, 500 MHz): 1.28-1.37, 1.40-1.47, 1.51-1.70, 1.73-1.80, 1.83-1.90 [8H, m, (CH$_2$)$_4$], 2.14-2.21, 2.27-2.35, 2.36-2.42, 2.52-2.55, 2.64-2.81 (6H, m, CH$_2$NCH$_2$CH$_2$), 2.33, 2.37 (3H, 2s, NCH$_3$), 2.93 [1H, p, CHC(OH)], 3.78 (1H, bs, OH), 5.22 (1H, m CO$_2$CH), 7.24-7.27, 7.31-7.35, 7.64-7.66 (5H, m, Ph) ppm.

(2R) 3-(2-Cyclopentyl-2-phenyl-2-hydroxyacetoxy)-1-(methoxycarbonylmethyl)-1-methylpyrrolidinium Bromide, Compound (c)

To compound 2R-4 (0.15 g, 0.49 mmol) in 6 ml of dry acetonitrile, methyl bromoacetate (0.194 g, 1.27 mmol) was added at room temperature. The mixture was stirred for 6 h. Evaporation of acetonitrile gave a crude product. The crude product was dissolved in a small volume of methylene chloride and then poured into 50 ml of dry ethyl ether to precipitate. This procedure was repeated three times to obtain the product, Compound (c) (0.1879 g, 83%), as a mixture of four diastereoisomers in an NMR-estimated ratio of 1:1:2:2. White powder, m.p.: 153-155° C. $[\alpha]^{25°}_D$=+0.5° (c=1 g/100 ml CHCl$_3$). Analysis for $C_{21}H_{30}BrNO_5.0.2H_2O$. Calcd: C, 54.86; H, 6.62; N, 3.05. Found: C, 54.75; H, 6.66; N, 3.01. $^1$H NMR (CDCl$_3$, 500 MHz): 1.30-1.37, 1.41-1.50, 1.55-1.73 [8H, m, (CH$_2$)$_4$], 1.93-2.00, 2.12-2.26, 2.75-2.95, 3.00-3.03, 4.30-4.50, 4.57-4.61 [7H, m, CHC(OH) and CH$_2$NCH$_2$CH$_2$], 3.09, 3.30 (1H, 2s, OH), 3.64, 3.66, 3.84, 3.95, 3.97 (3H, 5s, NCH$_3$), 3.74, 3.77, 3.79, 3.81 (3H, 4s, CO$_2$CH$_3$), 4.78, 4.83; 4.90, 4.97; 5.30, 5.35; 5.37, 5.41 (2H, 4 groups of 2dd, CH$_2$CO$_2$), 5.53 (1H, m, CO$_2$CH), 7.23-7.29, 7.31-7.38, 7.56-7.60 (5H, m, Ph) ppm.

(2R) 3-(2-Cyclopentyl-2-phenyl-2-hydroxyacetoxy)-1-(ethoxycarbonylmethyl)-1-methylpyrrolidinium Bromide, Compound (d)

To compound 2R-4 (0.22 g, 0.73 mmol) in 10 ml of dry acetonitrile, ethyl bromoacetate (0.21 ml, 0.316 g, 1.89 mmol) was added at room temperature. The mixture was stirred for 22 hours. Removal of acetonitrile gave a crude product. The crude product was dissolved in small volume of ethylene chloride and then poured into 50 ml of dry ethyl ether to precipitate. This procedure repeated three times to obtain the product, Compound (d) (0.3085 g, 90%) as a mixture of four diastereoisomers in an NMR-estimated ratio of 1:1:2:2. White powder, m.p.: 143-145° C. $[\alpha]^{25°}_D$=+5.6° (c=1 g/100 ml CHCl$_3$). Analysis for $C_{22}H_{32}BrNO_5.0.3H_2O$. Calcd: C, 55.53; H, 6.91; N, 2.94. Found: C, 55.46; H, 6.85; N, 2.97. $^1$H NMR (CDCl$_3$, 500 MHz): 1.26, 1.28, 1.32, 1.35 (3H, 4t, CH$_3$CH$_2$), 1.44-1.50, 1.53-1.63, 1.65-1.70 [8H, m, (CH$_2$)$_4$], 1.93-2.00, 2.04-2.11, 2.18-2.25, 2.76-2.96, 3.01-3.04, 4.09-4.26 [7H, m, CHC(OH) and CH$_2$NCH$_2$CH$_2$], 3.06, 3.28 (1H, 2s, OH), 3.66, 3.69, 3.81, 3.82, 3.94, 3.96 (3H, 6s, NCH$_3$), 4.61, 4.69; 4.76, 4.85; 5.17, 5.22; 5.26, 5.30 (2H, 4 set of dd, CH$_2$CO$_2$), 4.26-4.52 (2H, m, CH$_3$CH$_2$), 5.53 (1H, m, CO$_2$CH), 7.24-7.29, 7.31-7.38, 7.56-7.60 (5H, m, Ph) ppm.

Preparation of (±) 3-(2-cyclopentyl-2-phenyl-2-hydroxyacetoxy)-1-(carboxymethyl)-1-methylpyrrolidinium inner salt [Compound (bb)] and (2R) 3-(2-cyclopentyl-2-phenyl-2-hydroxyacetoxy)-1-(carboxymethyl)-1-methylpyrrolidinium Inner Salt [Compound (cc)]

Both the racemic and isomeric acids were prepared by hydrolysis from the corresponding methyl esters, (±) and (2R) 3-(2-cyclopentyl-2-phenyl-2-hydroxyacetoxy)-1-(methoxycarbonylmethyl)-1-methylpyrrolidinium bromide, that have been synthesized and characterized (elemental analysis, NMR) as described above. To Compounds (bb) and (cc) in aqueous solutions, equimolar ratios of 0.1 N NaOH were added. The mixture was stirred at room temperature for 3 h, and completion of reaction was verified by HPLC. After volume adjustment by water, a 1% solution of Compound (bb), or Compound (cc), pH about 6.5, was obtained. The resulting solution was used as is or diluted with normal saline for the experiments.

Analytical Methods

A high performance liquid chromatographic (HPLC) method was developed for the quantitative analysis of Compound (cc). The system consisted of a Spectra Physics (San Jose, Calif.) SP 8810 isocratic pump, a SP 8450 Uv/Vis detector (wavelength set to 230 nm), a SP 4290 integrator, and a Supelco Discovery C16 column. The mobile phase consisted of acetonitrile, water, and acetic acid at a ratio of 30:70:0.1. At a flow rate of 1 mL/min and an injection volume of 10 μL, the retention time was 7.10 min, and the detection limit was 1 μg/mL.

Stability Studies

Stability in Aqueous Solutions

A 0.1% water solution of Compound (cc) (pH 6.5) was kept at room temperature or 37° C. At various time points, samples were withdrawn and analyzed by HPLC.

Stability in Biological Media

Freshly collected rat blood, plasma, and 30% liver and lung homogenates were used. Aliquots of 1% of Compound (cc) in water solution were added to the biological mediums at 37° C., to yield final concentrations of 0.1%. At appropriate time intervals, samples (0.1 mL) were withdrawn and mixed with 0.2 mL of 5% dimethylsulfoxide in acetonitrile solution. The mixtures were centrifuged, and the supernatants were further diluted two times by water and analyzed by HPLC. The extraction rate was compared to a calibration standard and determined to be 100±3% (n=4).

In Vitro Pharmacodynamic Evaluations
Receptor Binding Affinity

Receptor binding studies on Compound (bb), Compound (cc), glycopyrrolate, and N-methylscopolamine were performed with N—[$^3$H]-methyl-scopolamine (NMS) in assay buffer (phosphate-buffered saline, PBS, without $Ca^{++}$ or $Mg^{++}$, pH 7.4), following the protocol from Applied Cell Science Inc. (Rockville, Md.). A 10 mM NaF solution was added to the buffer as an esterase inhibitor. The assay mixture (0.2 mL) contained 20 μL diluted receptor membranes (receptor proteins: $M_1$, 38 μg/mL; $M_2$, 55 μg/mL; $M_3$, 27 μg/mL; $M_4$, 84 μg/mL). The final concentration of NMS for the binding studies was 0.5 μM. Specific binding was defined as the difference in [$^3$H]NMS binding in the absence and presence of 5 μM atropine for $M_1$ and $M_2$ or 1 μM atropine for $M_3$ and $M_4$. Incubation was carried out at room temperature for 120 min. The assay was terminated by filtration through a Whatman GF/C filter (presoaked overnight with 0.5% polyethyleneimine). The filter was then washed six times with 1 mL ice cold buffer (50 mM Tris-HCl, pH 7.8, 0.9% NaCl), transferred to vials, and 5 mL of Scintiverse was added. Detection was performed on a Packard 31800 liquid scintillation analyzer (Packard Instrument Inc., Downer Grove, Ill.). Data obtained from the binding experiments were fitted to the % [$^3$H]NMS bound=$100-[100x''/k/(1+x''/k)]$ equation, to obtain the Hill coefficient n, and then to % [$^3$H]NMS bound=$100-[100x''/IC_{50}/(1+x'')/IC_{50})]$, to obtain the $IC_{50}$ values (x being the concentration of the tested compound). Based on the method of Cheng and Prusoff [*Biochem. Pharmacol.* 22: 3099-3108 (1973)], $K_i$ was derived from the equation $K_i=IC_{50}/(1+L/K_d)$, where L is the concentration of the radioligand. $IC_{50}$ represents the concentration of the drug causing 50% inhibition of specific radioligand binding, and $K_d$ represents the dissociation constant of the radioligand receptor complex. Data were analyzed by a non-linear least-square curve-fitting procedure using Scientist software (MicroMath Inc., Salt Lake City, Utah).

Determination of $pA_2$ Values

Male guinea pigs obtained from Harlan Sprague Dawley Inc. (Indianapolis, Ind.) and weighing about 400 g were used after overnight fasting. Animals were sacrificed by decapitation, and the ileum (the region of 5 cm upward of the cecum) was isolated and removed. The ileum was cut into 2.5 cm pieces and suspended in an organ bath containing 30 mL of mixture of Tyrode's solution and 0.1 mM hexamethonium bromide. The organ bath was constantly aerated with oxygen and kept at 37° C. One end of the ileum strip was attached to a fixed support at the bottom of the organ bath, and the other end to an isometric force transducer (Model TRN001, Kent Scientific Corp., Conn.) operated at 2-10 g range. The ileum strip was kept at a 2 g tension, and carbachol was used as antagonist. The ileum contracted cumulatively upon the addition of consecutive doses of carbachol (10-20 μL of $2\times10^{-4}$-$2\times10^{-3}$ M in water solution). Contractions were recorded on a physiograph (Kipp & Zonen Flarbed Recorder, Holland). After the maximum response was achieved, the ileum was washed three times, and a fresh Tyrode's solution containing appropriate concentration of the antagonist [Compound cc), Compound (bb), Compound (c), glycopyrrolate, or scopolamine] was replaced. An equilibration time of 10 min was allowed for the antagonists before the addition of carbachol. In each experiment, 5 to 6 different concentrations were used, and a Schild plot was used to obtain the $pA_2$ values. Four to six trials were performed for each antagonist.

In Vivo Pharmacodynamic Evaluations
Mydriatic Studies

Topical administration. The mydriatic effects of Compound (cc) have been compared to those of glycopyrrolate, tropicamide, and its parent soft drugs, Compounds (c) and (d), in rabbit eyes. Four healthy, male New-Zealand white rabbits weighting about 3.5 kg were used. To investigate the dose-mydriatic-response relationships, 100 μL of various concentrations of the compounds (0-1%) were administered in the eyes to determine the pharmacodynamically equivalent doses, the lowest doses that induce the maximum pupil dilations. Drug solutions were applied to one eye; only water was applied to the other eye that served as control. Experiments were carried out in a light- and temperature-controlled room. At appropriate time intervals, the pupil diameters of both eyes were recorded. Difference in pupil diameters between each time-point and zero time-point were calculated for both treated and control eyes and reported as mydriatic responses [(treated-control)/control in %]. Control eye dilations were monitored to determine whether systemic absorption had occurred or not. The area under the mydriatic response-time curve ($AUC^{eff}$) was calculated by the trapezoidal rule, and it was used to compare the activity and duration of action of the tested compounds.

Intravenous Administration.

New-Zealand white rabbits (4 kg) were injected i.v. with Compound (cc) or glycopyrrolate at a dose of 2.5 μmol/kg (about 1 mg/kg), and the mydriatic response was recorded for both eyes at various time points.

Cardiac Studies
Effect on Resting Heart Rate

Male Sprague-Dawley rats, weighing 300±30 g, were anesthetized with 50 mg/kg (i.p.) of sodium pentobarbital. Needle electrodes were inserted s.c. into the limbs of the anesthetized rats and were joined to a GOULD 2000 recorder (GOULD Inc., Cleveland, Ohio). Standard leads I, II, and III were recorded at a paper speed of 25 mm/sec. After a 15 min period of stabilization, baseline electrocardiography (ECG) was taken, and drug was administrated. Compound (cc) in normal saline (5 μmol/kg, about 2 mg/kg) or vehicle only, was administered in the jugular vein (1 mL/kg). Heart rate was recorded at designated time-points for 2.5 h.

Effect on Carbachol-Induced Bradycardia

Rats were prepared as previously described. Recording was taken before, during, and after the administration of any of the compounds, until all basic ECG parameters returned to the baseline. ECG recordings were evaluated for the following parameters: PP cycle length (msec), RR cycle length (msec), heart rate (1/min) by the equation of 60000/RR cycle length, and presence of Mobitz II type atrio-ventricular (A-V) block (2:1, 3:1, etc.). To evaluate the effects of carbachol, the negative chronotropic and dromotropic effects were analyzed. These effects of carbachol were manifested on the surface ECG as sinus bradycardia (lengthening of the PP cycle) and as a development of Mobitz II type A-V block. After analyzing the ECG recordings, the percent changes of heart rate, as compared to that of the baseline, were plotted against time, and the effects of drugs on the percent changes of the heart rate were characterized. Compound (cc) (0 to 5 μmol/kg) and glycopyrrolate (0.5 μmol/kg) were dissolved in 0.9% NaCl and injected into the jugular veins (1 mL/kg) at time 0, while carbachol (80 μg/mL, 0.06-0.1 mL volume according to the initial individual ECG response of each rat) was injected at various time-points after drug administration. Student's t-test was used for statistical evaluations.

Pharmacokinetic Studies
Pharmacokinetics after Intravenous Administration

Male Sprague-Dawley rats (body weight about 400 g) were anesthetized with 30 mg/kg of sodium pentobarbital (i.p.). A 1% solution of Compound (cc) was injected in the jugular vein. Due to the low sensitivity of HPLC detection (1 µg/mL), a dose of 30 mg/kg was used. Blood samples, 0.12 mL, were collected through heparinized syringe from the contralateral jugular vein at appropriate time intervals, and plasma (0.05 mL) was separated. The plasma samples were mixed with 0.1 mL of acetonitrile containing 5% dimethyl sulfoxide and centrifuged. The supernatants were further mixed with one volume of water, centrifuged, and analyzed by HPLC. The concentrations of Compound (cc) have been determined using a calibration curve obtained by addition of known amounts of the compound to plasma and prepared following the same methodology for HPLC analysis (r=0.995). Non-compartmental and compartmental pharmacokinetic analysis was performed using WinNonlin (Pharsight Corp., Mountain View, Calif.). In noncompartmental analysis, the area under the curve (AUC) of the plasma concentration versus time was calculated using the trapezoidal rule. The area from the last concentration measured ($C_t$) to infinity was calculated as $C_t/\beta$, where $\beta$ is the terminal disposition rate constant. Total body clearance ($CL_{tot}$) was calculated as Dose/AUC. Mean residence time (MRT) was calculated as AUMC/AUC, where AUMC, the area under the first moment curve, was calculated using the trapezoidal rule from the graph of plasma concentration×time vs. time. Extrapolation of AUMC from the last time point t to infinity was calculated as $C_t/\beta+C_t/\beta^2$. The volume of distribution at the steady state ($Vd_{ss}$) was determined as the product of $CL_{tot}$ and MRT. For compartmental analysis, data were fitted with a two-compartment model, $C=Ae^{-\alpha t}+Be^{-\beta t}$, where C is the drug concentration in plasma, A and B are the exponential multipliers, $\alpha$ and $\beta$ are the hybrid rate constants for the distribution and elimination phase, respectively. AUC was calculated as $A/\alpha+B/\beta$, and the half-life of the terminal phase ($t_{1/2}$) was obtained as $\ln2/\beta$. The volume of distribution of the central compartment, $Vd_c$, was calculated as Dose/A+B. The elimination rate constant, $K_{el}$, was calculated as $CL_{tot}/Vd_c$. Unweighted data were used in all analyses.

Excretion after Intravenous Administration

Male Sprague-Dawley rats (350±10 g) were anesthetized by injection of sodium pentobarbital (30 mg/kg, i.p.). The urinary tract was closed to prevent urination, and urine samples were collected directly from the urinary bladder through a 26 gauged needle. The peritoneal cavity was exposed, and the bile duct was cannulated using a polyethylene tube (PE 10). Compound (cc) (10 mg as 1 mL 1% solution) was administered intravenously (jugular vein). At various time intervals after administration, total bile juice and urine were collected and weighed in centrifuge tubes. Samples were taken at 0 min (control) and then every 15 min until 2 h after i.v. administration. A 5% mannitol in normal saline solution was injected (0.5 mL) in the jugular vein every 30 min to increase the volume of the urine for sample collections (about 0.2 mL per 15 min). The collected bile and urine samples were prepared, diluted properly, and analyzed by HPLC as described in the pharmacokinetic studies. Noncompartmental analysis for the urine data after bolus i.v. was performed using WinNonlin. Maximum observed excretion rate ($C_{max}$) was recorded, and the first order elimination rate constant (k) was estimated via linear regression using the logarithmic plot. The half life ($t_{1/2}$) was calculated as $\ln2/k$, and the amount of cumulative elimination, $A_e$, was calculated by summation of the concentration-volume products of each sample. Using the remaining amounts vs. time, a sigma (−) plot was also developed, and k and $t_{1/2}$ were calculated subsequently for comparison.

Results and Discussion
Preparation of Zwitterions

Both Compound (cc) and its racemic equivalent Compound (bb) are hydrolytic products of soft anticholinergic compounds, (2R) 3-(2-cyclopentyl-2-phenyl-2-hydroxyacetoxy)-1-(methoxycarbonylmethyl)-1-methylpyrrolidinium bromide, Compound (c), or the corresponding (±) compound, Compound (a). They were prepared by simple hydrolysis in basic aqueous solution of the corresponding ester.

Solubility and Stability

Both zwitterionic Compound (cc) and Compound (bb) are very soluble in aqueous solutions (pH 6.5) and biological media, and they are also very stable. A 0.1% water solution kept at room temperature showed no decomposition after one year. In freshly collected rat blood, plasma, and 30% liver and lung homogenates, there was no change in the HPLC peak area after two hours at 37° C. Thus, Compound (cc) (0.1%) is also very stable toward metabolic transformations.

Pharmacodynamic Evaluations
Receptor Binding Affinity

The receptor binding affinities, $pK_i$, of Compound (cc) and Compound (bb) are presented in Table 1 together with that of the parent soft drugs of Compound (cc), that is, the methyl ester Compound (cc) and the ethyl ester Compound (d), and those of glycopyrrolate and N-methylscopolamine for comparison. The receptor binding affinity of the zwitterionic metabolite is considerably less than that of glycopyrrolate or N-methylscopolamine, and is about an order of magnitude less than that of their parent methyl ester soft drugs; i.e., Compound (cc) vs. Compound (c) (all differences statistically significant at the p<0.05 level using either t-tests or nonparametric Mann-Whitney U tests). This is in good agreement with the hypothesis that presence of the acidic moiety formed by hydrolysis of the parent soft drug ester inactivates the drug, but because in these zwitterionic structures, the electronic distribution somewhat resembles those of the neutral (and active) anticholinergics, and thus significant activity is still retained. Contrary to its parents Compound (c) or Compound (d) that show no $M_3/M_2$ subtype selectivity, Compound (cc) shows a significantly better (p<0.01, t-test assuming equal variances), almost five-fold subtype selectivity (Table 1 below), further increasing its safety profile. Furthermore, even on these structures, the 2R isomer shows increased affinity confirming the stereospecificity of muscarinic receptors. Hill coefficients (n) were not very different from unity indicating that, in general, drug-receptor interactions obeyed the law of action and binding took place at only one site. The receptor binding affinity of N-methylscopolamine determined here was in good agreement with previously published results.

TABLE 1

Receptor binding affinities, $M_3/M_2$ selectivities, and $pA_2$ values.

| Cpd. | Subtypes of cloned muscarinic receptors[a] | | | | Selectivity | |
|---|---|---|---|---|---|---|
| | $M_1$ | $M_2$ | $M_3$ | $M_4$ | $M_3/M_2$ | $pA_2$[b] |
| Cpd (cc) | 8.11 ± 0.16 | 7.48 ± 0.12 | 8.12 ± 0.10 | 8.23 ± 0.12 | 4.4 ± 0.3 | 7.20 ± 0.19 |
| | (0.83 ± 0.11) | (1.10 ± 0.11) | (0.83 ± 0.01) | (0.83 ± 0.01) | | |
| Cpd (bb) | 6.19 ± 0.06 | 5.48 ± 0.13 | 5.84 ± 0.07 | 6.44 ± 0.06 | 2.3 ± 0.7 | 6.42 ± 0.30 |
| | (1.11 ± 0.06) | (1.02 ± 0.20) | (1.01 ± 0.07) | (0.84 ± 0.06) | | |
| Cpd (c) | 8.89 ± 0.04 | 8.87 ± 0.05 | 9.00 ± 0.06 | 9.52 ± 0.01 | 1.4 ± 0.1 | 8.31 ± 0.05 |
| | (0.83 ± 0.11) | (1.10 ± 0.11) | (0.83 ± 0.01) | (0.83 ± 0.01) | | |
| Cpd (d) | 8.67 ± 0.16 | 8.84 ± 0.34 | 8.74 ± 0.02 | 8.85 ± 0.13 | 0.9 ± 0.6 | 8.55 ± 0.16 |
| | (0.86 ± 0.08) | (0.92 ± 0.01) | (1.09 ± 0.15) | (0.89 ± 0.02) | | |
| glycopyrrolate | 9.76 ± 0.05 | 9.19 ± 0.18 | 8.73 ± 0.05 | 9.90 ± 0.08 | 0.4 ± 0.1 | 8.57 ± 0.12 |
| | (1.37 ± 0.20) | (0.99 ± 0.11) | (1.14 ± 0.25) | (1.02 ± 0.01) | | |
| scopolamine methyl bromide | 9.69 ± 0.01 | 9.18 ± 0.21 | 9.29 ± 0.12 | 9.92 ± 0.21 | 1.3 ± 0.4 | 9.16 ± 0.19 |
| | (0.92 ± 0.10) | (1.02 ± 0.02) | (1.07 ± 0.01) | (0.90 ± 0.04) | | |

[a]Receptor binding $pK_i$ data represent mean ± S.D. of 3 experiments. The numbers in parentheses denote Hill slopes.
[b]$pA_2$ values were determined on 4-6 ileum strips obtained from different animals. Data represent mean ± S.D.

Guinea Pig Ileum Assay, $pA_2$ Value

The $pA_2$ values determined from guinea pig ileum contraction assays, which represent the negative logarithm of the molar concentration of the antagonist that produces a two-fold shift to the right in an agonist's concentration-response curve, are a classical functional study of anticholinergic affinity (at $M_3$ muscarinic receptors). Values obtained for the present compounds from ileum longitudinal contractions by using carbachol as agonists with the method of van Rossum (50) are presented in Table 1 above. Compared to the parent esters Compound (c) and (d), glycopyrrolate, or N-methylscopamine, $pA_2$ values indicate even somewhat less activity for the zwitterionic Compound (cc) than the receptor binding assays, and this assay also confirmed the higher activity of the 2R isomers. The $pA_2$ values of the Compound (cc) and (bb) metabolites are 1.1±0.3 and 1.3±0.3 less than those of the corresponding ethyl and methyl parent ester soft drugs, respectively indicating again that they are a good order of magnitude less active. Comparison of this to the average of close to two orders of magnitude decrease in activity seen previously in the same $pA_2$ assay for three other acidic metabolites versus their corresponding ethyl ester parents, 1.8±0.5 (31-33), confirms the hypothesis that these spatially-close zwitterions are likely to retain more activity than the previous metabolite structures, but are still inactivated to a good extent.

Mydriatic Studies

These studies were performed to evaluate the in vivo potency of these metabolites following local or systemic administration.

Topical Administration

The potency and duration of action of Compound (cc) was compared to those of its parent ester soft drugs Compounds (c) and (d), glycopyrrolate, and tropicamide (the most frequently used short acting mydriatic agent). Following topical administration of 100 µL drug solution to one eye in rabbits, the pupil size was measured, and the maximum mydriatic effect (% change in pupil size) and area under the mydriatic response-time curves ($AUC^{eff}_{0-168h}$) were determined. See Table 2.

TABLE 2

Maximum response ($R_{max}$, maximum % change in pupil size) and area under the response-time curve ($AUC^{eff}$) after topical administration (0.1 mL).[a]

| Compound | Conc. (%) | $R_{max}$ (%) | $AUC^{eff}_{0-168h}$ |
|---|---|---|---|
| Cpd (cc) | 0 | 0.00 ± 0.00 | 0 ± 0 |
| | 0.01 | 31.00 ± 7.14 | 73 ± 24 |
| | 0.02 | 38.79 ± 7.45 | 103 ± 22 |
| | 0.05 | 51.38 ± 8.81 | 175 ± 46 |
| | 0.1 | 50.34 ± 7.92 | 182 ± 40 |
| | 0.2 | 55.65 ± 9.24 | 240 ± 38 |
| | 0.5 | 56.79 ± 10.71 | 590 ± 205 |
| | 1 | 53.65 ± 10.84 | 612 ± 115 |
| Cpd (bb) | 0.01 | 1.85 ± 2.14 | 0.7 ± 0.9 |
| | 1 | 45.37 ± 8.19 | 119 ± 34 |
| Cpd (c) | 0.5 | 52.92 ± 13.41 | 752 ± 342 |
| | 1 | 57.08 ± 11.66 | 875 ± 197 |
| Cpd (d) | 0.5 | 53.96 ± 13.27 | 1170 ± 308 |
| | 1 | 56.04 ± 11.69 | 1532 ± 526 |
| glycopyrrolate | 0.02 | 35.97 ± 9.84 | 1879 ± 664 |
| | 0.05 | 48.73 ± 12.66 | 2476 ± 847 |
| | 0.1 | 52.95 ± 10.93 | 3732 ± 866 |
| | 0.2 | 53.24 ± 14.49 | 4923 ± 2175 |
| tropicamide | 0.02 | 30.27 ± 9.74 | 99 ± 40 |
| | 0.05 | 35.00 ± 9.18 | 167 ± 116 |
| | 0.2 | 42.72 ± 9.60 | 435 ± 150 |
| | 0.5 | 44.64 ± 11.17 | 622 ± 171 |

[a]Data represent mean ± SD of four trials.

Accordingly, it was found that Compound (cc) produces local mydriatic activity ($R_{max}$), but only with short duration of action ($AUC^{eff}_{0-168h}$). See FIG. 1. Recovery times, time-periods needed for the size of pupil in the treated eye to recover within less than 1 mm of the control, were approximately 102, 24, and 6 h after administration of 0.2% of glycopyrrolate, 1.0% Compound (d), and Compound (cc), respectively. Compound (cc) was less potent and shorter acting than its parent esters, Compound (a) and Compound (d). In agreement with previous results, its racemic form Compound (bb) showed even lower potency. Furthermore, Compound (cc) did not cause any observable irritation reactions, such as eye-closing, lacrimation, or mucous discharge; and unlike conventional anticholinergics, it did not cause pupil dilation in the contralateral, untreated eye, indicating not only low topical and systemic side effects, but also rapid elimination from the systemic circulation.

Intravenous Administration

Figure 2:
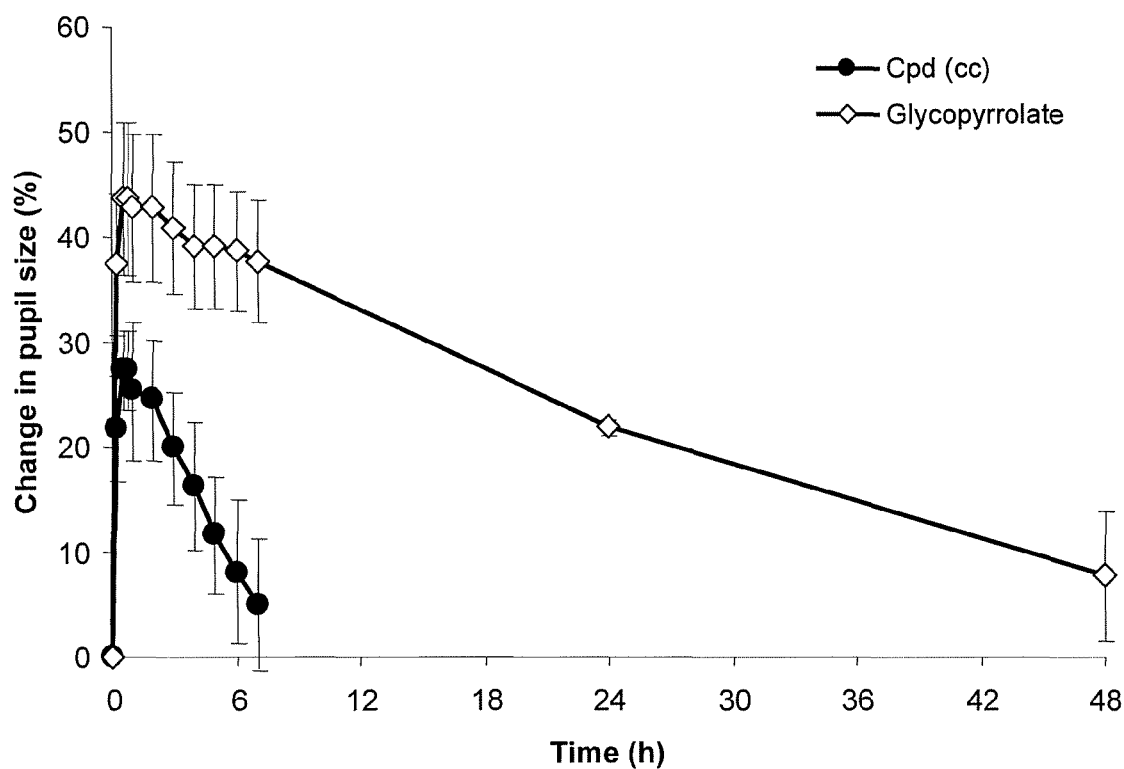
FIG. 2 is a graph showing mydriatic response (change in pupil size) with time after intravenous administration of 2.5 µmol/kg of Compound (cc) or glycopyrrolate in rabbits (n=4).

To evaluate the likelihood of causing side effects after systemic administration, the mydriatic response following an intravenous (i.v.) dose of 2.5 µmol/kg (about 1 mg/kg through ear vein) also was investigated in rabbits. As shown in FIG. 2, Compound (cc) produced some mydriasis after i.v. administration, but its magnitude and duration of action were much less than those produced by glycopyrrolate.

Cardiac Studies

Effect on Resting Heart Rate

Figure 3:
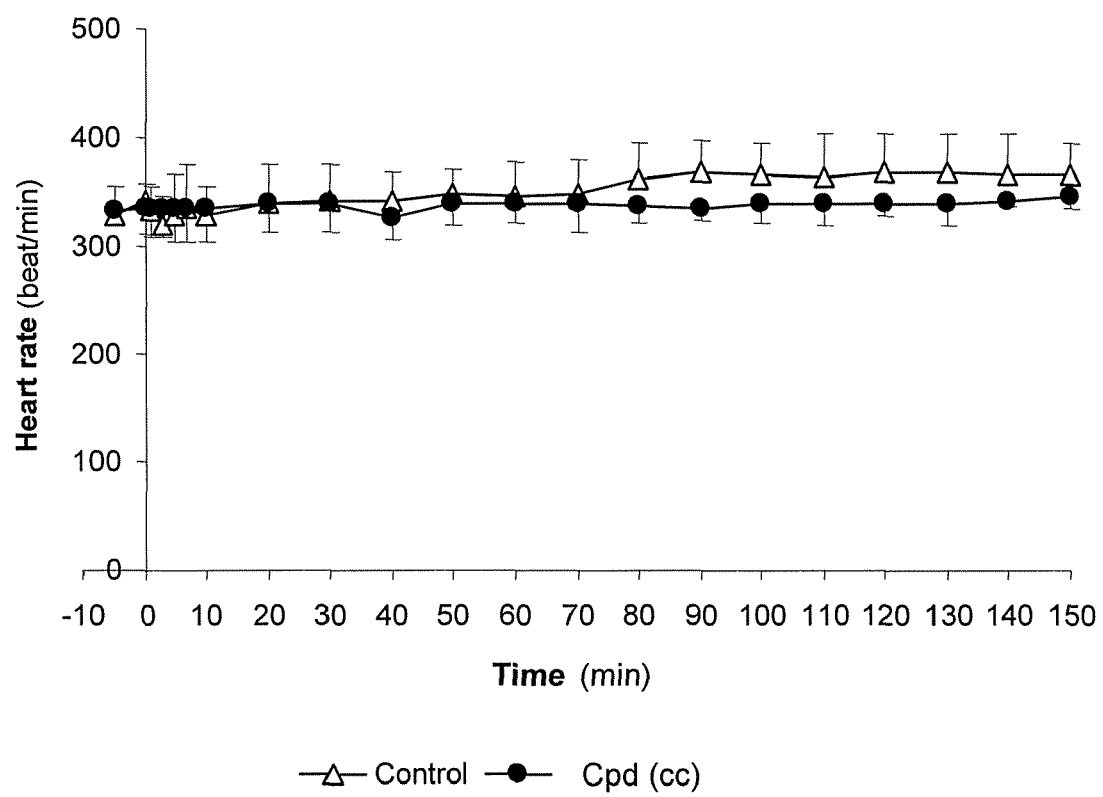
FIG. 3 is a graph showing the effect of Compound (cc) (5 µmol/kg) on the resting heart rate in anesthetized rats (n=4) as compared to control rats.

After i.v. administration of normal saline (vehicle control) or Compound (cc) in pentobarbital-anesthetized rats, the heart rate was recorded every 10 min up to 2.5 h. Results indicate that at a dose of 5 µmol/kg (about 2 mg/kg), Compound (cc) did not affect the resting heart rate in any of the four animals, further confirming its slight subtype selectivity. Results are depicted in FIG. 3.

Effect on Carbachol-Induced Bradycardia.

Figure 4:
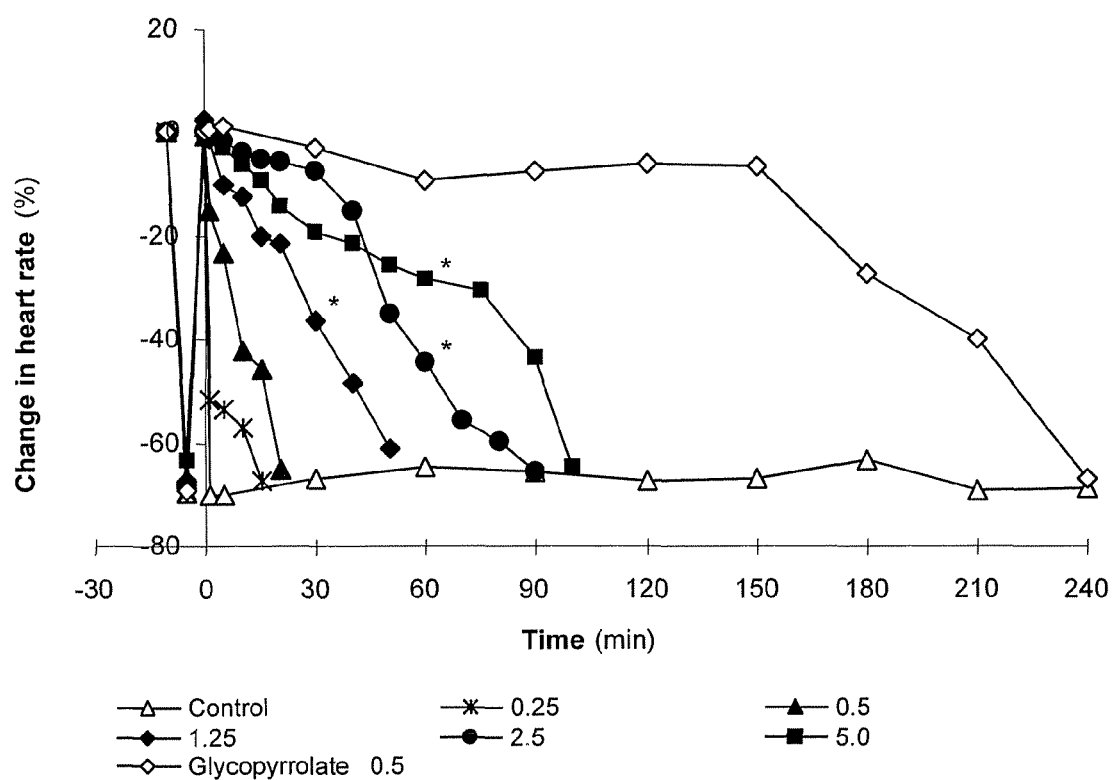
FIG. 4 is a graph showing the protective effect of varying doses of Compound (cc) (0.25, 0.5, 1.25, 2.5 and 5.0 µmol/kg) and glycopyrrolate (0.5 µmol/kg) on carbachol-induced bradycardia (n=4), where the asterisks indicate p<0.005 compared to glycopyrrolate.

The magnitude of cardiac effects of Compound (cc) and glycopyrrolate were assessed by measuring the extent and duration of their bradycardia protecting activities. Intravenous injection of carbachol at a dose of 16-26 µg/kg to rats produces a temporary sinus bradycardia and Mobitz II A-V block in a safe and reproducible manner. This can be fully prevented by prior administration of an anticholinergic agent, and the effects of various anticholinergics differ greatly in their extent and duration of action. In this study, various doses (0.25-5 µmol/kg) of Compound (cc) have been investigated and compared to glycopyrrolate (0.5 µmol/kg). As shown in FIG. 4, carbachol injection (e.g., at −5 min) induced a temporary Mobitz II A-V block with more than 60% inhibition of the normal heart rate (control). After i.v. injection at 0 min of Compound (cc) or glycopyrrolate at various doses, carbachol at the same dose induced various degrees of inhibition. The zwitterionic Compound (cc) showed bradycardia-protecting activity immediately after i.v. administration, but this diminished rapidly. At a dose of 0.5 µmol/kg, two out of three rats showed full prevention of the carbachol induced bradycardia at 1 min, and at a dose of 1.251 µmol/kg, all three rats showed full prevention. These protecting effects disappeared completely in less than 30 and 60 min, respectively. Even at higher doses, such as 2.5 and 5 µmol/kg, the effect of Compound (cc) disappeared in less than 100 min indicating that fast elimination from the systemic circulation rapidly reduces the potential to induce heart-related side effects. For comparison, glycopyrrolate showed full protection for more than 2.5 h and partial effect for another 1.5 h even at a ten-times smaller dose (0.5 µmol/kg).

Pharmacokinetic Studies

Pharmacokinetics after Intravenous Administration

Figure 5:
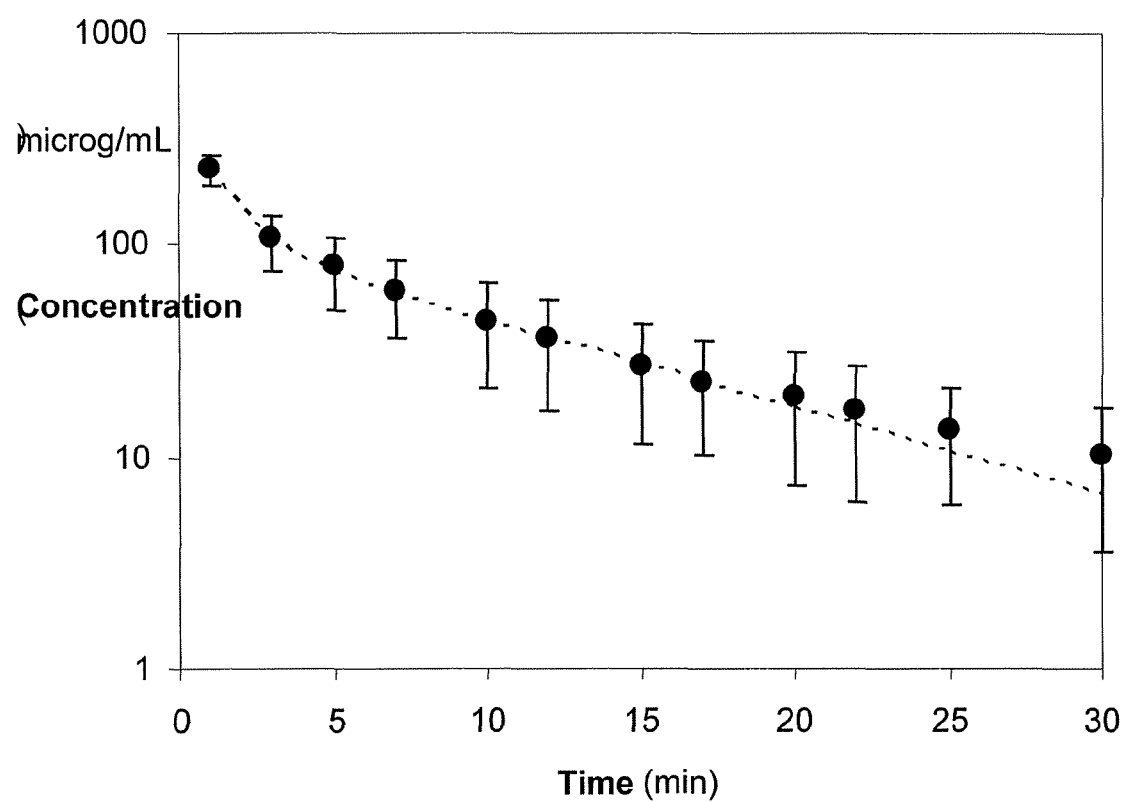
FIG. 5 is a graph depicting a mean plasma concentration-time profile after intravenous injection of Compound (cc) at a dose of 30 mg/kg in rats (n=4), where the line represents data predicted by the two compartment model (Table 3).

An in vivo pharmacokinetic evaluation of Compound (cc) was performed in rats. After a single i.v. bolus injection, plasma concentrations at predetermined time points were quantified by HPLC. The observed plasma concentration time-profile of Compound (cc) (FIG. 5) could be best described by a two-compartmental body model corresponding to a bi-exponential equation, $C = Ae^{-\alpha t} + Be^{-\beta t}$. Pharmacokinetic parameters obtained from non-compartmental (NCA) and compartmental analyses are shown in Table 3 below. The elimination half-life $t_{1/2}$ was about 10.7 min with a volume of distribution $Vd_{ss}$ of 193 mL/kg and a total body clearance $CL_{tot}$ of about 20 mL/min/kg (NCA). For the compartmental analysis, the correlation coefficient, r, was >0.999 in all individuals. Parameters were in general agreement with the NCA results. These clearly demonstrate that even a high dose (30 mg/kg) of Compound (cc) is rapidly cleared and well-tolerated in animals, an important requirement for soft drug metabolites.

TABLE 3

Pharmacokinetics of Compound (cc) after i.v. bolus administration in rats.

| Parameter | Mean | SD |
|---|---|---|
| Dose, mg/kg | 30 | |
| Noncompartmental analysis results | | |
| $C_{max}$, µg/mL | 330.74 | 31.96 |
| $k_e$, min$^{-1}$ | 0.066 | 0.01 |
| $t_{1/2}$, min | 10.7 | 1.40 |
| $AUC_\infty$, (µg · min/mL) | 1676 | 637 |
| $CL_{tot}$, (mL/min)/kg | 19.59 | 6.05 |
| $AUMC_\infty$, (µg · min²/mL) | 18281 | 10850 |
| $MRT_\infty$, min | 10.33 | 2.12 |
| $Vd_{ss}$, mL/kg | 192.99 | 30.94 |
| Compartmental analysis results | | |
| A, µg/mL | 292.46 | 25.37 |
| B, µg/mL | 111.41 | 39.71 |
| α, min$^{-1}$ | 0.851 | 0.145 |
| β, min$^{-1}$ | 0.094 | 0.012 |
| $t_{1/2\alpha}$, min | 0.832 | 0.14 |
| $t_{1/2\beta}$, min | 7.44 | 0.96 |
| $Vd_c$, mL/kg | 75.20 | 9.86 |
| $Vd_{ss}$, mL/kg | 167.91 | 22.76 |
| r | 0.9994 | 0.0005 |

Excretion after Intravenous Administration

Total bile juice and urine were collected every 15 min for up to 2 h and analyzed by HPLC after i.v. administration of a dose of 10 mg of Compound (cc) (1 mL of 1% solution). No detectable levels of Compound (cc) were excreted in the bile, but relatively large amounts of Compound (cc) were excreted in the urine. Table 4 below presents the results of non-compartmental analysis of the urine data (log rate plot and sigma minus plot). At one hour after injection, the cumulative excretion amount was about 50% of the administered dose. The first order elimination rate constants $k_e$ were estimated, and the elimination half lives $t_{1/2}$ were derived from the slopes of these two plots (14.0 and 13.1 min, respectively). These results, again, indicate a rapid elimination of Compound (cc) from the systemic circulation mainly through urinary excretion.

TABLE 4

Excretion of Compound (cc) in urine after i.v. bolus administration in rats.

| Parameter | Mean | SD |
|---|---|---|
| Dose, mg | 10 | |
| Log rate plot | | |
| $C_{max}$, mg/mL | 0.193 | 0.046 |
| $A_e$, mg (cumm. excr.) | 5.08 | 0.46 |
| $k_e$, min$^{-1}$ | 0.050 | 0.0062 |
| $t_{1/2}$, min | 14.02 | 1.73 |
| $AUC_{0-last}$, (mg/mL) × min | 4.36 | 0.34 |
| $AUC_\infty$, (mg/mL) × min | 4.46 | 0.31 |
| r | 0.974 | 0.021 |
| Sigma minus plot | | |
| $k_e$, min$^{-1}$ | 0.0539 | 0.0089 |
| $t_{1/2}$, min | 13.13 | 2.22 |
| r | 0.995 | 0.003 |

Conclusion

The present PK/PD studies demonstrated that the zwitterionic metabolite Compound (cc) retains significant but reduced activity of its parent quaternary ammonium ester soft drugs, and is very rapidly eliminated from the systemic circulation mainly through urinary excretion of its unchanged form. Furthermore, as Compound (cc) also showed moderate $M_3/M_2$ muscarinic receptor subtype selectivity, the likelihood of cardiac side effects is further reduced for this metabolite.

Further Studies

Purpose. Because stereospecificity is known to be important at muscarinic receptors, isomers of both N-substituted soft anticholinergics based on glycopyrrolate, (2R) 3-(2-cyclopentyl-2-phenyl-2-hydroxyacetoxy)-1-(alkoxycarbonylmethyl)-1-methylpyrrolidinium bromide methyl and ethyl esters, Compounds (c) and (d), and their zwitterionic metabolite, (2R) 3-(2-cyclopentyl-2-phenyl-2-hydroxyacetoxy)-1-methyl-1-carboxymethylpyrrolidinium inner salt [Compound (cc)], were synthesized and their pharmacological activities were evaluated in vitro and in vivo.

Methods. The isomers of Compounds (c) and (d) were synthesized with both optically pure methyl-cyclopentyl-mandelate and 3-hydroxy-N-methylpyrrolidine. Trans-esterification followed by quarternization with alkyl bromoacetate gave four isomers of the methyl or ethyl ester with the nitrogen chiral center unresolved. The hydrolysis of these four isomers followed by HPLC separation resulted in eight fully resolved isomers of the corresponding acid. The pharmacological activities were assessed using the in vitro receptor-binding assay, guinea pig ileum $pA_2$-assay, and in vivo rabbit mydriatic effect. The results were compared with that of conventional anticholinergic agents such as glycopyrrolate, N-meythylscopolamine, and tropicamide as well as that of previously prepared racemates and 2R isomers.

Results. The receptor binding at cloned human muscarinic receptors ($M_1$-$M_4$ subtypes), $pK_i$ values, of these newly synthesized methyl and ethyl ester isomers were in the 6.0-9.5 range, and zwitterion isomers in 5.0-8.6 range. In both cases, 2R isomers were found significantly more active than 2S isomers (27-447 times for methyl ester isomers, and 6 to 4467 times for zwitterion isomers). Among four isomers of the methyl ester Compound (c) (with chiral center 1' unresolved), the 3'R isomers were more active than the corresponding 3'S isomers (1.5-12.9 times). However, in the case of zwitterion isomers, the 3'S isomers were not always more active than the corresponding 3'R isomers, indicating that activity determined based on chiral center 3' is significantly affected by the configuration of other two chiral centers, 2 and 1'. In the completely resolved 8 zwitterion isomers (all the three chiral centers resolved), it was found that 1'S isomers were more active than the corresponding 1'R isomers in all cases (1.8-22.4 times). The results also indicate that some isomers showed good $M_3/M_2$ muscarinic-receptor subtype-selectivities (about 3-5 times), and 2R and 3'S were the determining configurations for this property. Guinea pig ileum assays and rabbit mydriasis test on zwitterion isomers also confirmed the stereospecificity. In rabbit eyes, some 2R-zwitterion isomers showed mydriatic potencies similar to glycopyrrolate and exceeded tropicamide, but their mydriatic effects lasted considerably less time, and they did not induce dilation of the pupil in the contralateral, water-treated eyes. These results indicate that, in agreement with their soft nature, they are locally active, but safe and have a low potential to cause systemic side effects. The pharmacological potency of eight zwitterion isomers was concluded to be (2R1'S3'S, 2R1'S3'R and 2R1'R3'S)>2R1'R3'R>2S1S3'R>(2S1'S3'S and 2S1'R3'R)>2S1'R3'S.

Conclusions. The stereospecificity and $M_3/M_2$ muscarinic-receptor subtype-selectivity of soft anti-cholinergics, Compounds (c) and (d) and their zwitterionic metabolite Compound (cc), have been demonstrated. Adding to the previous results, safe use of these soft drugs has been confirmed.

Introduction

Stereospecificity of anticholinergics is important at muscarinic receptors. Compounds (c) and (d), (2R) 3-(2-cyclopentyl-2-phenyl-2-hydroxyacetoxy)-1-(alkoxycarbonylmethyl)-1-methylpyrrolidinium bromide, and their common zwitterionic metabolite, (2R) 3-(2-cyclopentyl-2-phenyl-2-hydroxyacetoxy)-1-methyl-1-carboxymethylpyrrolidinium inner salt, have shown promising activity and safety in animal studies. These compounds indeed exhibited stereospecificity toward muscarinic receptors, and the anticholinergic activity has been improved with the 2R configuration. In addition, the zwitterionic metabolite also showed a moderate $M_3/M_2$ muscarinic-receptor subtype-selectivity that indicates a reduced systemic cardiac side effect. However, the molecules of this type of soft analogs possess three chiral centers, so that each racemic compound may contains up to eight different isomers, that is 2R1'R3'R, 2R1'R3'S, 2R1'S3'R, 2R1'S3'S, 2S1'R3'R, 2S1'R3'S, 2S1'S3'R, and 2S1'S3'S as displayed below:

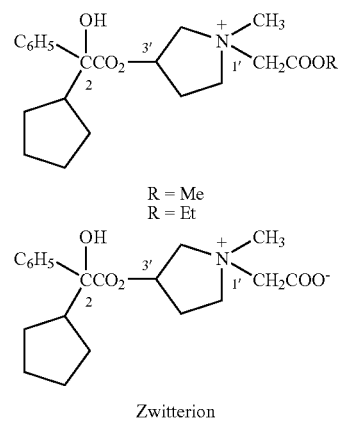

Zwitterion

Thus, the above-described investigations in the soft glycopyrrolate isomers based on one resolved chiral center (2R or 2S) only expressed that 2R enantiomers (a mixture of four diastereoisomers 2R1'3'R, 2R1'R3'S, 2R1'S3'R, 2R1'S3'S) were more active than 2S enantiomers (a mixture of 2S1'R3'R, 2S1'R3'S, 2S1'S3'R, 2S1'S3'S). In this section, further investigations in the stereospecificity of these soft glycopyrrolates are reported using five partially-resolved soft anticholinergic ester isomers and eight fully resolved zwitterion metabolite, isomers (as described for 2R and 2S enantiomers). The compounds were systematically synthesized and isomers were separated. The relative pharmacological activities and $M_3/M_2$ muscarinic-receptor subtype-selectivities were investigated by in vitro receptor-binding assay, in vitro guinea pig ileum $pA_2$-assay, and in vivo mydriatic effect in rabbits.

Materials and Methods

Materials

Glycopyrrolate (glycopyrronium bromide) was kindly provided by Boehringer Ingelheim Chemicals, Inc. Carbamylcholine bromide (carbachol), atropine methylbromide (atropine MeBr), and scopolamine methylbromide (scopolamine MeBr) were obtained from Sigma Chemicals Co. (St. Louis, Mo.), and tropicamide (1%) was obtained from Bausch & Lomb Pharmaceutical (Tampa, Fla.). N—[$^3$H]-Methyl-scopolamine (NMS) was obtained from Amersham Biosciences UK Limited (Buckinghamshire, UK). Cloned human muscarinic receptor subtypes $M_1$-$M_4$ were obtained from Applied Cell Science Inc. (Rockville, Md.). Scintiverse BD was from Fisher Scientific Co. (Pittsburgh, Pa.). (R)-3-hydroxy pyrrolidine hydrochloride and (S)-3-hydroxy pyrrolidine hydrochloride were from Astatech Inc. (Monmouth Junction, N.J.). N—[$^3$H]-Methyl-scopolamine (NMS) was from Amersham Biosciences UK Limited (Buckinghamshire, UK). Cloned human muscarinic receptor subtypes $M_1$-$M_4$ were from Applied Cell Science Inc. (Rockville, Md.). Scintiverse BD was from Fisher Scientific Co. (Pittsburgh, Pa.). Other chemicals used for synthesis were reagent or HPLC grade, and were obtained from Aldrich (Milwaukee, Wis.) and Fisher Scientific Co. Melting points were taken on Fisher-Johns melting apparatus. NMR spectra were recorded on Bruker Advance 300, 400 and 500 MHz NMR spectrometers, and are reported in ppm relative to TMS. NOESY was performed using 2D NMR spectrometer, Mercury-300BB. Animal studies were performed in accordance with the Guide for the Care and Use of Laboratory Animals adopted by the National Institute of Health, USA. Institutional animal care and use committee (IACUC) approval was obtained prior to the initiation of this research and during its execution.

Synthesis of 2R-Isomers

Racemic Cyclopentylmandelic Acid, 1

Cyclopentylmagnesium bromide ether solution (100 ml, 2M; 0.2 mol) was added drop-wise to benzoylformic acid (15 g, 0.1 mol) in 330 ml of anhydrous ethyl ether at 0° C. The mixture was stirred at 0° C. for 30 min and at room temperature for 24 h. The reaction mixture was treated with 1 N HCl, and the aqueous solution was extracted with ether. The combined ether solution was treated with $K_2CO_3$ solution. The potassium carbonate solution was acidified with HCl and extracted with ether twice. The ether solution was dried with anhydrous sodium sulfate and evaporated to give a crude product. The crude product was washed with water to get pure racemic cyclopentylmandelic acid 1 (8.0 g, 36.4%). Needle-like crystal, m.p.: 153-154° C. $^1$H NMR (CDCl$_3$, 300 MHz): 1.28-1.39, 1.42-1.50, 1.51-1.61, 1.63-1.72 [8H, m, (CH$_2$)$_4$], 2.93 [1H, p, CHC(OH)], 7.26-7.30, 7.33-7.36, 7.65-7.67 (5H, m, Ph) ppm.

Resolution of Racemic Cyclopentylmandelic Acid, R(−)1

(−)-Strychnine (11.4 g) in 100 ml of methanol (suspension) was added to racemic cyclopentylmandelic acid 1 (7.5 g) in methanol (20 ml) at room temperature. The reaction solution was allowed to stand overnight. The crystals were filtered and crystallized again with hot methanol. The second crop of crystals was collected by filtration and treated with sodium hydroxide solution. The basic solution was extracted with methylene chloride twice (methylene chloride solution discarded), and then acidified with hydrochloric acid to recover the resolved cyclopentylmandelic acid. To this resolved acid (20.6 mg in 0.1 ml of ethyl acetate), 13 μL of (+)-α-phenylethylamine was added. The precipitate which formed was washed with hexane three times and dried under vacuum. The precipitate was identified by NMR as optically pure cyclopentylmandelic acid, R(−)1, (2.5 g, 33.3%). M.p.: 121-122° C. $[\alpha]^{25}_D$=−22.5° (c=1 g/100 ml, CHCl$_3$). $^1$H NMR (CDCl$_3$, 300 MHz): 1.28-1.39, 1.42-1.50, 1.51-1.61, 1.64-1.73 [8H, m, (CH$_2$)$_4$], 2.93 [1H, p, CHC(OH)], 7.25-7.28, 7.32-7.35, 7.64-7.65 (5H, m, Ph) ppm.

Methyl(−)-cyclopentylmandelate, R(−)2

To a mixture of (−)-cyclopentylmandelic acid, R(−)1, (1.83 g, 8.3 mmol) and potassium carbonate (2.87 g, 21 mmol) in DMF (21 ml), methyl iodide (3.53 g, 25 mmol) was added at room temperature. The mixture was stirred at room temperature for 2 h, and then poured into water and extracted with hexane three times. Evaporation of dried hexane extract gave a crude product. Flash chromatography of the crude product on silica gel with 1.5:1 hexane:methylene chloride gave pure product R(−)$_2$ (1.90 g, 95%). $^1$H NMR (CDCl$_3$, 300 MHz): 1.32-1.36, 1.43-1.61 [8H, m, (CH$_2$)$_4$], 2.90 [1H, p, CHC(OH)], 3.71 (1H, s, OH), 3.79 (3H, s, CH$_3$), 7.25-7.28, 7.31-7.35, 7.63-7.65 (5H, m, Ph) ppm.

(R)-3-Hydroxy-N-Methyl Pyrrolidine, (R)3

In a 100 ml flask, 2 g (R)-3-Hydroxy pyrrolidine, 25 ml THF, 0.49 g paraformaldehyde and 1.5 g formic acid (90%) were added. The mixture was stirred under reflux for 5 hours (until all solid disappeared), then cooled at 0° C. and added with 10 ml of NaOH solution (10 N) to adjust the pH to about 10. The organic layer was separated and dried over MgSO$_4$. After filtering the dried solution and removing the solvent (THF), an oily product (1.5 g, 92%) of (R)3 was obtained. $^1$H NMR (CDCl$_3$, 300 MHz): 1.50-1.60 (m, 1H), 1.98-2.10 (m, 1H), 2.25 (s, 3H), 2.25-2.40 (m, 2H), 2.50-2.60 (m, 1H), 2.61-2.70 (m, 1H), 3.80 (brs, 1H), 4.20-4.30 (m, 1H).

(S)-3-Hydroxy-N-Methyl Pyrrolidine, (S)3

Synthesis of (S)3 was the same as for (R)3, except that the starting material was (S)-3-Hydroxy pyrrolidine. The resultant product (S)3 (1.5 g, 92%) was also an oil. $^1$H NMR (DMSO-D6 300 MHz): 1.50-1.60 (m, 1H), 1.98-2.05 (m, 1H), 2.15 (s, 3H), 2.15-2.35 (m, 2H), 2.45-2.52 (m, 1H), 2.61-2.70 (m, 1H), 4.20 (brs, 1H), 4.60-4.70 (m, 1H).

3(R)—N-Methyl-3-pyrrolidinyl-2(R)-cyclopentyl-mandelate, 4

A solution of R(−)2 (0.7 g, 3 mmol) and (R)3 (0.7 g, 7 mmol) in 40 ml of toluene was heated until 20 ml of toluene had distilled. Approximately 0.003 g of sodium was added, and the solution was stirred and heated for 2 h as the distillation was continued. More toluene was added at such a rate as to keep the reaction volume constant. Additional sodium was added at the end of an hour. The solution was then cooled and extracted with 3N HCl. The acid extract was made alkaline with concentrated NaOH and extracted three times with ether. Removal of dried ether solution gave a crude oil. Flash chromatography of the crude product on silica gel with 8:1 of EtOAc and EtOH gave an oil product of 4 (0.4 g, 44%). $^1$H NMR (CDCl$_3$, 300 MHz): 1.28-1.37, 1.51-1.70, 1.83-1.90 [8H, m, (CH$_2$)$_4$], 2.27-2.40 (m, 3H), 2.52-2.55 (m, 1H), 2.64-2.72 (m, 1H), 2.74-2.81 (m, 1H), 2.33 (3H, s, NCH$_3$), 2.93 [1H, p, CHC(OH)], 3.85 (1H, bs, OH), 5.22 (m, 1H), 7.24-7.27, 7.31-7.35, 7.64-7.66 (5H, m, Ph) ppm.

3(S)—N-Methyl-3-pyrrolidinyl-2(R)-cyclopentyl-mandelate, 5

Synthesis of 5 was the same as for 4, except (S)3 was used instead of (R)3. The resultant product 5 (0.35 g, 39%) was also an oil. $^1$H NMR (CDCl$_3$, 400 MHz): 1.28-1.37, 1.51-1.70, 1.75-1.82[8H, m, (CH$_2$)$_4$], 2.15-2.22 (m, 1H), 2.30-2.40 (m, 2H), 2.65-2.70 (m, 1H), 2.70-2.82 (m, 2H), 2.35 (3H, s, NCH$_3$), 2.95[1H, p, CHC(OH)], 3.82 (1H, bs, OH), 5.22 (m, 1H), 7.24-7.27, 7.31-7.35, 7.64-7.66 (5H, m, Ph) ppm.

(2R,3'R) 3-(2-Cyclopentyl-2-phenyl-2-hydroxyacetoxy)-1-(methoxycarbonylmethyl)-1-methylpyrrolidinium bromide, 6 [Compound (e)]

To Compound 4 (0.3 g, 0.98 mmol) in 12 ml of dry acetonitrile, methyl bromoacetate (0.5 g, 3.2 mmol) was added at room temperature. The mixture was stirred for 6 h. Evaporation of acetonitrile gave a crude product. The crude product was dissolved in a small volume of methylene chloride and then poured into 50 ml of dry ethyl ether to precipitate. This step was repeated three times to obtain the pure product 6, or Compound (e), (0.3 g, 70%) as a white powder that was a mixture of two diastereoisomers in a NMR-estimated ratio of 2:1. $^1$H NMR (CDCl$_3$, 400 MHz): 1.30-1.37, 1.41-1.50, 1.55-1.70[8H, m, (CH$_2$)$_4$], 2.10-2.27 (m, 1H), 2.79-2.95 (m, 2H), 3.05, 3.60 (2s, total 3H, N—CH3), 3.75, 3.79 (2s, total 3H, O-Me), 3.95-4.40 (m, 4H), 4.68, 5.16 (2AB, total 2H, N—CH2—COOMe), 5.52-5.58 (m, 1H), 7.23-7.29, 7.31-7.38, 7.56-7.60 (5H, m, Ph) ppm.

(2R,3'S) 3-(2-Cyclopentyl-2-phenyl-2-hydroxyacetoxy)-1-(methoxycarbonylmethyl)-1-methylpyrrolidinium Bromide, 7a [Compound (f)]

To Compound 5 (0.16 g, 0.52 mmol) in 8 ml of dry acetonitrile, methyl bromoacetate (0.3 g, 1.9 mmol) was added at room temperature. Following the same procedure for 6 [Compound (e)] the pure product 7a [Compound (f)] (0.16 g, 80%) was obtained. Compound (f) was also a white powder and a mixture of two diastereoisomers in a NMR-estimated ratio of 2:1. $^1$H NMR (CDCl$_3$, 400 MHz): 1.30-1.70[8H, m, (CH$_2$)$_4$], 1.95-2.00, 2.10-2.20 (m, 1H), 2.75-2.95 (m, 2H), 3.30, 3.70 (2s, total 3H, N—CH3), 3.78, 3.82 (2s, total 3H, O-Me), 4.00-4.42 (m, 4H), 4.90, 5.38 (2AB, total 2H, N—CH2—COOMe), 5.52-5.58 (m, 1H), 7.23-7.29, 7.31-7.38, 7.56-7.60 (5H, m, Ph) ppm.

(2R,3'S) 3-(2-Cyclopentyl-2-phenyl-2-hydroxyacetoxy)-1-(ethoxycarbonylmethyl)-1-methylpyrrolidinium Bromide, 7b [Compound (g)]

To Compound 5 (0.16 g, 0.52 mmol) in 10 ml of dry acetonitrile, ethyl bromoacetate (0.32 g, 1.9 mmol) was added at room temperature. The mixture was stirred for 22 hours, and the removal of acetonitrile gave a crude product. The crude product was dissolved in small volume of ethylene chloride, and then poured into a 50 ml of dry ethyl ether to afford a precipitate. This procedure was repeated three times, and the pure product 7b, or Compound (g) (0.16 g, 80%) was obtained. Compound (g) was also a white powder and a mixture of two diastereoisomers in a NMR-estimated ratio of 2:1. $^1$H NMR (CDCl$_3$, 400 MHz): 1.32, 1.35 (2t, 3H, CH$_3$CH$_2$), 1.40-1.50, 1.53-1.63, 1.65-1.80[8H, m, (CH$_2$)$_4$], 1.93-2.11 (m 2H), 2.80-2.96 M, 2H), 3.30, 3.70 (2s, 3H, N—CH3), 4.10-4.60 (m, 6H), 4.79, 5.30 (2H, 2 set of dd, CH$_2$CO$_2$), 5.53 (1H, m), 7.24-7.29, 7.31-7.38, 7.56-7.60 (5H, m, Ph) ppm.

Hydrolysis of Esters

Compounds (e) and (f) were combined with equimolar ratios of 0.1 N NaOH. The mixtures were stirred at room temperature for 3 hours to obtain the corresponding racemic zwitterionic products, 8 and 9 in aqueous solution (colorless, pH about 6.5). Compound 8 is (2R,3'R) 3-(2-cyclopentyl-2-phenyl-2-hydroxyacetoxy)-1-(carboxymethyl)-1-methylpyrrolidinium inner salt. Compound 9 is (2R,3'S) 3-(2-cyclopentyl-2-phenyl-2-hydroxyacetoxy)-1-(carboxymethyl)-1-methylpyrrolidinium inner salt.

HPLC Separations for 8a, 8b, and 9a, 9b

The solutions of 8 and 9 each contained two isomers, 8a, 8b and 9a, 9b, at a ratio of 2:1 that could be separated by HPLC. The HPLC system consisted of a Spectra Physics (San Jose, Calif.) SP 8810 isocratic pump, a SP 8450 UV/Vis detector (wavelength set to 230 nm), a SP 4290 integrator, and a Supelco Discovery RP Amide C16 column. The mobile phase consisted of acetonitrile and water at a ratio of 30:70. With 100 µL injection at a flow rate of 1 mL/min, the retention times were 7.2 min for 8a and 9a, and 8.5 min for 8b and 9b. The effluence corresponding to each isomer was collected, and the solvent was evaporated to obtain the final zwitterionic isomers, 8a, 8b, and 9a, 9b as following:

(2R,1'R,3'R) 3-(2-cyclopentyl-2-phenyl-2-hydroxyacetoxy)-1-(carboxymethyl)-1-methylpyrrolidinium inner salt, 8a [Compound (dd)]: white powder $^1$H NMR (CDCl$_3$, 300 MHz): 1.30-1.65 (m, 8H), 2.02-2.12 (m, 1H), 2.20-2.60 (brs, 1H), 2.60-2.80 (m, 1H), 2.82-2.92 (m, 1H), 3.30 (s, 3H), 3.55-3.65 (m, 1H), 3.72-3.82 (m, 1H), 3.90-4.05 (m, 2H), 4.10-4.15 (m, 1H), 5.38-5.45 (m, 1H), 7.15-7.20 (m, 1H), 7.32-7.38 (m, 2H), 7.55-7.62 (m, 2H).

(2R,1'S,3'R) 3-(2-cyclopentyl-2-phenyl-2-hydroxyacetoxy)-1-(carboxymethyl)-1-methylpyrrolidinium inner salt, 8b [Compound (ee)]: $^1$H NMR (CDCl$_3$, 300 MHz): 1.30-1.75 (m, 8H), 2.02-2.10 (m, 1H), 2.10-2.40 (brs, 2H), 2.70-2.80 (m, 1H), 2.80-2.90 (m, 1H), 2.95 (s, 3H), 3.55-3.65 (m, 2H), 3.85-4.0 (m, 3H), 4.05-4.10 (m, 1H), 5.38-5.45 (m, 1H), 7.15-7.20 (m, 1H), 7.25-7.30 (m, 2H), 7.50-7.60 (m, 2H).

(2R,1'R,3'S) 3-(2-cyclopentyl-2-phenyl-2-hydroxyacetoxy)-1-(carboxymethyl)-1-methylpyrrolidinium inner salt, 9a [Compound (ff)]: white powder, $^1$H NMR (CDCl$_3$, 500 MHz): 1.30-1.65 (m, 8H), 2.02-2.12 (m, 1H), 2.50-2.60 (m, 1H), 2.78-2.88 (m, 1H), 3.25 (s, 3H), 3.65-4.05 (m, 4H), 4.15-4.30 (brs, 2H), 5.30-5.40 (m, 1H), 7.13-7.23 (m, 1H), 7.26-7.32 (m, 2H), 7.55-7.60 (m, 2H).

(2R,1'S,3'S) 3-(2-cyclopentyl-2-phenyl-2-hydroxyacetoxy)-1-(carboxymethyl)-1-methylpyrrolidinium inner salt, 9b [Compound (gg)]: white powder, $^1$H NMR (CDCl$_3$, 500 MHz): 1.30-1.70 (m, 8H), 1.90-1.98 (m, 1H), 2.65-2.70 (m, 1H), 2.85-2.90 (m, 1H), 3.15 (s, 3H), 3.65-3.90 (m, 4H), 4.05-4.10 (M, 1H), 4.15-4.22 (brs, 1H), 5.35-5.42 (m, 1H), 7.18-7.23 (m, 1H), 7.27-7.32 (m, 2H), 7.53-7.58 (m, 2H).

Determination of Absolute Configurations

Nuclear overhauser effect (NOE) has been used to identify the absolute configuration of the product 8b. Compound was dissolved in CDCl$_3$, and the 2D $^1$H—$^1$H NOESY spectrum was taken by Mercury-300BB.

Synthesis of 2S-isomers

Cis-(2S,5S)-2-(tert-butyl)-5-phenyl-1,3-dioxolan-4-one, 10

S(+)-mandelic acid in hexane suspension (50 g, 328 mmol) was added with pivaldehyde (42.7 ml, 396 mmol) then trifluoromethanesulfonic acid (1.23 ml, 14 mmol) at room temperature. The mixture was warmed to 36° C., and the reaction was followed by TLC for 5 hr until no starting material could be detected. The mixture was then cooled to room temperature and added with 8% aqueous NaHCO$_3$. The water layer was removed and the organic layer was dried over Na$_2$SO$_4$. After filtration and removal of the solvent, 62.17 g of the crude product was obtained. Recrystallization of the crude product gave 44.71 g of pure cis-(2S,5S)-2-(tert-butyl)-5-phenyl-1,3-dioxolan-4-one in 88% yield as a needle-like crystal. $^1$H NMR (CDCl$_3$, 300 MHz): 1.08 (s. 9H), 5.24 (s, 1H), 5.33 (s, 1H), 7.40-7.46 (m, 5H) ppm. $^{13}$C NMR (CDCl$_3$, 300 MHz): 23.6, 34.4, 77.0, 109.3, 127.0, 128.7, 129.2, 133.4, 147.2.

Cis-(2S,5S)-2-(tert-butyl)-5-phenyl-5-cyclopentyl-1, 3-dioxolan-4-one, 11

At −78° C., a lithium bis-(trimethylsilyl)amide in hexane solution (120 ml, 120 mmol, 1.0M in hexane) was added to compound 10 (25 g, 113.5 mmol, dissolved in 100 ml of dried THF), stirred for 1 hr, followed by addition of cyclopentyl bromide (25 g, 168 mmol). This reaction was kept at −78° C. for 4 hr, then slowly warmed up to room temperature and continued for overnight. The completion of the reaction was followed by TLC. With stirring, a solution of 10% of NH$_4$Cl (25 ml) was added in the mixture. Then, the mixture was poured into a separation funnel containing 10% NH$_4$Cl solution (200 ml). The aqueous layer was discarded, and the organic layer was dried over Na$_2$SO$_4$. The solvent was removed to give a crude product, which was then re-crystallized in hexane to give a pure product, 11 (20.36 g, yield 63%, white crystal). $^1$H NMR (CDCl$_3$, 300 MHz): 1.15 (s, 9H), 1.55-1.95 (m, 8H), 2.74 (m, 1H), 5.62 (s, 1H), 7.44-7.56 (m, 3H), 7.88-7.91 (m, 2H) ppm. $^{13}$C NMR (CDCl$_3$, 300 MHz): 23.5, 24.5, 25.3, 26.6, 35.6, 50.9, 83.2, 110.6, 124.9, 127.5, 127.9, 138.9, 173.7.

S(+)-Cyclopentylmandelic Acid, 12

To a solution of cis-(2S,5S)-2-(tert-butyl)-5-cyclopentyl-5-phenyl-1,3-dioxolan-4-one (14.35 g, 50 mmol) in 100 ml methanol and 50 ml water, 15 g of KOH was added slowly. The mixture was stirred and heated (65° C.) to reflux for 3-4 hr, then cooled down to the room temperature, and methanol was removed. To the aqueous solution, 100 ml of ethyl acetate was added, then acidified to pH 1 with 3N HCl. The mixture was poured into a separation funnel, and the organic layer was separated. The aqueous layer was extracted two times with ethyl acetate (50 ml). The combined organic layers were dried over Na$_2$SO$_4$, filtered, and the solvent was removed to provide 13.44 g of yellowish crude product, which was re-crystallized to give a pure product of S(+)-cyclopentylmandelic acid, 12 (6.89 g, yield 62%, white crystal). $^1$H NMR (CDCl$_3$, 300 MHz): 1.28-1.75 (m, 8H), 2.94 (m, 1H), 7.24-7.34 (m, 3H), 7.62-7.68 (m, 2H). $^{13}$C NMR (CDCl$_3$, 300 MHz): 25.9, 26.3, 26.4, 26.9, 47.1, 79.2, 125.8, 127.7, 128.2, 140.8, 180.9.

Methyl S(+)-cyclopentylmandelate, 13

S(+)-cyclopentylmandelic acid, 12 (5.5 g, 25 mmol), and potassium carbonate (8.61 g, 63 mmol) in DMF (60 ml) solution was added with methyl iodide (10.6 g, 75 mmol). The mixture was stirred at room temperature for 3 hr, poured into water, and extracted with hexane for three times. Evaporation of dried hexane extract gave a pure product of S(+)-cyclopentylmandelate, 13 (5.85 g, 100%, clear oil). $^1$H NMR (CDCl$_3$, 300 MHz): 1.32-1.61 [8H, m, (CH$_2$)$_4$], 2.90 [1H, p, CHC(OH)], 3.76 (s, 3H), 3.78 (s, 1H), 7.25-7.35 (m, 3H), 7.63-7.65 (m, 2H). $^{13}$C NMR (CDCl$_3$, 300 MHz): 25.9, 26.2, 26.3, 26.8, 47.1, 53.2, 79.1, 125.8, 127.3, 128.0, 141.6, 176.0.

(R)-3-Hydroxy-N-Methylpyrrolidine, (R)3

In a 100 ml flask, 4 g (R)-3-Hydroxy pyrrolidine hydrochloride salt, 50 ml THF and 1.3 g NaOH were added and stirred for 20 min. Then, 1.1 g paraforaldehyde and 4.8 g formic acid (90%) were added. The mixture was heated (60° C.) and stirred at reflux for 2 hr until all solid disappeared. The mixture was cooled to 0° C., combined with 6.5 ml of 10 N NaOH solution (pH about 10), and extracted twice with ethyl ether (50 ml). The combined organic layer was dried over Na$_2$SO$_4$. Evaporation of the dried organic layer gave a yellowish, oily product of (R)3 (3.0 g, 92%). $^1$H NMR (CDCl$_3$, 300 MHz): 1.65-1.75 (m, 1H), 2.15-2.36 (m, 2H), 2.33 (s, 3H), 2.55-2.59 (m, 2H), 2.76-2.85 (m, 1H), 4.30-4.40 (m, 1H), 4.8-5.10 (brs, 1H). $^{13}$C NMR (CDCl$_3$, 300 MHz): 35.4, 41.9, 54.7, 64.9, 70.9.

(S)-3-Hydroxy-N-Methylpyrrolidine, (S)3

Synthesis of (S)3 was the same as for (R)3, except the starting material was (S)-3-Hydroxypyrrolidine hydrochloride salt. The resultant product (S)3 (3.10 g, 95%) was also an oil. $^1$H NMR (CDCl$_3$, 300 MHz): 1.50-1.60 (m, 1H), 2.05-2.30 (m, 2H), 2.28 (s, 3H), 2.40-2.50 (m, 2H), 2.70-2.80 (m, 1H), 4.25-4.30 (m, 1H), 4.80 (brs, 1H). $^{13}$C NMR (CDCl$_3$, 300 MHz): 35.4, 41.9, 54.7, 64.9, 70.9.

(3R) N-Methyl-3-pyrrolidinyl-(S)-cyclopentylmandelate, 14

In a 250 ml 3-neck flask equipped with Dean-Stark condenser, a mixture of methyl S(+)-cyclopentylmandelate, 13 (2 g, 8.8 mmol), (R)-3-hydroxy-N-methylpyrrolidine, (R)-3 (2 g, 20 mmol), and 100 ml of heptane was stirred and heated (110° C.) until 20 ml of heptane had been distilled. The temperature was reduced to 25° C., and approximately 0.003 g of sodium was added. The mixture was stirred and heated to 110° C. again for 3 hr as the distillation was continued. An additional piece of sodium (0.002 g) was added at the 1 hr point. More heptane was added at such a rate as to keep the reaction volume constant. The mixture was cooled to 0° C., mixed with 5 ml of water, and the organic layer was separated. The organic layer was extracted with 3N HCl. The acid extract was made alkaline (pH 10) with 5N NaOH and extracted three times with ether. Removal of dried ether solution (over Na$_2$SO$_4$) gave a clear, oily product 14 (1.6 g, 61.5%). $^1$H NMR (CDCl$_3$, 300 MHz): 1.28-1.80 [m, 9H], 2.15-2.25 (m, 1H), 2.30-2.40 (m, 1H), 2.37 (s, 3H), 2.65-2.80 (m, 3H), 2.90-3.00 (m, 1H), 3.85 (1H, brs, OH), 5.22 (m, 1H), 7.20-7.35 (m, 3H), 7.64-7.70 (m, 2H). $^{13}$C NMR (CDCl$_3$, 300 MHz): 26.0, 26.4, 26.5, 26.7, 32.1, 42.0, 47.1, 54.8, 62.0, 76.5, 79.1, 125.8, 127.3, 128.0, 141.7, 175.3.

(3S) N-Methyl-3-pyrrolidinyl-(S)-cyclopentylmandelate, 15

Following the same procedure as for 14, except (S)-3 was used instead of (R)-3, a clear, oily product of 15 (2.33 g, 89.6%) was obtained. $^1$H NMR (CDCl$_3$, 300 MHz): 1.24-1.70 (m, 9H), 1.80-1.88 (m, 1H), 2.25-2.40 (m, 2H), 2.35 (s, 3H), 2.55-2.70 (m, 2H), 2.75-2.82 (m, 1H), 2.90-3.00 (m, 1H), 3.95 (1H, bs, OH), 5.22 (m, 1H), 7.24-7.40 (m, 2H), 7.64-7.69 (m, 5H). $^{13}$C NMR (CDCl$_3$, 300 MHz): 26.0, 26.3, 26.4, 26.7, 32.6, 42.0, 47.1, 54.9, 61.6, 76.4, 79.2, 125.8, 127.3, 128.0, 141.7, 175.2.

(2S,3'R) 3-(2-Cyclopentyl-2-phenyl-2-hydroxyacetoxy)-1-(methoxycarbonylmethyl)-1-methylpyrrolidinium bromide, 16 [Compound (h)]

Compound 14 (0.6 g, 1.96 mmol) in 30 ml of dry acetonitrile was combined with methyl bromoacetate (1.0 g, 6.4 mmol) at room temperature. The mixture was stirred for 3 hr. Evaporation of acetonitrile gave a crude product. The crude product was dissolved in a small volume of methylene chloride and poured into a 100 ml of dry ethyl ether to obtain a precipitate. This procedure was repeated three times and gave compound (h) as the product (0.81 g, 89%, white powder). $^1$H NMR (CDCl$_3$, 300 MHz): 1.30-1.70 (m, 8H), 1.82-1.95 (brs, 1H), 2.10-2.20 (m, 1H), 2.75-2.90 (m, 2H), 3.25, 3.60 (2s, total 3H, N—CH3), 3.75, 3.79 (2s, total 3H, O-Me), 4.10-4.60 (m, 4H), 4.92, 5.35 (2AB, total 2H, N—CH2—COOMe), 5.52-5.58 (m, 1H), 7.23-7.38 (m, 3H), 7.56-7.60 (m, 2H). $^{13}$C NMR (CDCl$_3$, 300 MHz): 25.8, 25.9; 26.3, 26.4; 26.4, 26.5; 27.0, 27.0; 29.8, 30.1; 45.9, 46.8; 50.2, 51.4; 53.2, 53.2; 62.2, 63.2; 64.6, 64.7; 69.6, 69.7; 72.8, 73.1; 79.4, 79.6; 125.7, 125.7; 127.6, 127.9; 128.2, 128.4; 141.0, 141.2; 165.3, 165.5; 173.9, 174.2.

(2S,3'S) 3-(2-Cyclopentyl-2-phenyl-2-hydroxyacetoxy)-1-(methoxycarbonylmethyl-1-methylpyrrolidinium bromide, 17 [Compound (i)]

Following the same procedure as for Compound (h), except compound 15 was used instead of compound 14, the product Compound (i) (0.8 g, 88%, white powder) was obtained. $^1$H NMR (CDCl$_3$, 300 MHz): 1.30-1.75 (m, 8H), 1.80-1.90 (brs, 1H), 2.15-2.30 (m, 1H), 2.78-2.95 (m, 2H), 3.10, 3.65 (2s, total 3H, N—CH3), 3.75, 3.78 (2s, total 3H, O-Me), 4.15-4.52 (m, 4H), 4.85, 5.38 (2AB, total 2H, N—CH2—COOMe), 5.50-5.58 (m, 1H), 7.23-7.38 (m, 3H), 7.56-7.66 (m, 2H). $^{13}$C NMR (CDCl$_3$, 300 MHz): 25.8, 25.9; 26.2, 26.3; 26.3, 26.4; 26.8, 26.9; 29.4, 29.6; 45.6, 46.9; 50.1, 51.4; 53.1, 53.1; 62.2, 63.3; 64.8, 64.8; 69.5, 69.8; 72.8, 73.2; 79.4, 79.6; 125.6, 125.9; 127.6, 127.9; 128.2, 128.4; 140.7, 141.1; 165.2, 165.5; 173.9, 174.2.

Hydrolysis of Esters & HPLC Separations

The procedures used for obtaining the 2S-isomers 18a, 18b, 19a and 19b (white powder) were the same as for 2R-isomers 8a, 8b, 9a and 9b.

(2S,1'R,3'R) 3-(2-cyclopentyl-2-phenyl-2-hydroxyacetoxy)-1-(carboxymethyl)-1-methylpyrrolidinium inner salt, 18a [Compound (hh)]: $^1$H NMR (CDCl3, 300 MHz): 1.30-1.65 (m, 8H), 2.02-2.45 (m, 2H), 2.82-2.90 (m, 1H), 3.10-3.18 (m, 1H), 3.25 (s, 3H), 3.50-4.05 (m, 6H), 5.34-5.40 (m, 1H), 7.23-7.38 (m, 3H), 7.50-7.68 (m, 2H).

(2S,1'S,3'R) 3-(2-cyclopentyl-2-phenyl-2-hydroxyacetoxy)-1-(carboxymethyl)-1-methylpyrrolidinium inner salt, 18b [Compound (ii)]: $^1$H NMR (CDCl3, 300 MHz): 1.45-1.85 (m, 9H), 2.05-2.15 (m, 1H), 2.80-2.90 (m, 1H), 3.00-3.10 (m, 1H), 3.35 (s, 3H), 3.70-3.80 (m, 1H), 3.90-4.10 (m, 4H), 4.22-4.35 (m, 1H), 5.50-5.60 (m, 1H), 7.36-7.55 (m, 3H), 7.72-7.80 (m, 2H).

(2S,1'R,3'S) 3-(2-cyclopentyl-2-phenyl-2-hydroxyacetoxy)-1-(carboxymethyl)-1-methylpyrrolidinium inner salt, 19a [Compound (jj)]: $^1$H NMR (CDCl3, 300 MHz): 1.20-1.65 (m, 8H), 1.95-2.10 (m, 1H), 2.20 (brs, 1H), 2.40-2.50 (m, 1H), 2.78-2.90 (m, 1H), 3.15 (s, 3H), 3.70-3.90 (m, 2H), 3.96-4.20 (m, 4H), 5.38-5.50 (m, 1H), 7.20-7.38 (m, 3H), 7.55-7.65 (m, 2H).

(2S,1'S,3'S) 3-(2-cyclopentyl-2-phenyl-2-hydroxyacetoxy)-1-(carboxymethyl)-1-methylpyrrolidinium inner salt, 19b [Compound (kk)]: $^1$H NMR (CDCl3, 300 MHz): 1.35-1.70 (m, 8H), 2.00-2.15 (m, 1H), 2.70-2.90 (m, 2H), 3.00 (s, 3H), 3.42 (brs, 1H), 3.58-3.68 (m, 2H), 3.80-3.95 (m, 3H), 4.08-4.18 (m, 1H), 5.38-5.48 (m, 1H), 7.20-7.40 (m, 3H), 7.55-7.62 (m, 2H).

Receptor Binding Affinity

Receptor binding studies on soft anticholinergics isomers and their zwitterionic metabolite isomers, as well as glycopyrrolate, and N-methylscopolamine were performed with N—[$^3$H]-methyl-scopolamine (NMS) in assay buffer (phosphate-buffered saline, PBS, without Ca$^{++}$ or Mg$^{++}$, pH 7.4), following the protocol from Applied Cell Science Inc. (Rockville, Md.). A 10 mM NaF solution was added to the buffer as an esterase inhibitor. The assay mixture (0.2 mL) contained 20 μL diluted receptor membranes (receptor proteins: M$_1$, 38 μg/mL; M$_2$, 55 μg/mL; M$_3$, 27 μg/mL; M$_4$, 84 μg/mL). The final concentration of NMS for the binding studies was 0.5 nM. Specific binding was defined as the difference in [$^3$H] NMS binding in the absence and presence of 5 μM atropine for M$_1$ and M$_2$ or 1 μM atropine for M$_3$ and M$_4$. Incubation was carried out at room temperature for 2 hr. The assay was terminated by filtration through a Whatman GF/C filter (presoaked overnight with 0.5% polyethyleneimine). The filter was then washed six times with 1 mL ice cold buffer (50 mM Tris-HCl, pH 7.8, 0.9% NaCl), transferred to vials, and 5 mL of Scintiverse was added. Detection was performed on a Packard 31800 liquid scintillation analyzer (Packard Instrument Inc., Downer Grove, Ill.). Data obtained from the binding experiments were fitted to the equation %[$^3$H]NMS bound=100−[100x$^n$/k/(1+x$^n$/k)], to obtain the Hill coefficient n, and then to the equation %[$^3$H]NMS bound=100−[100x$^n$/IC$_{50}$/(1+x$^n$/IC$_{50}$)], to obtain the IC$_{50}$ values (x being the concentration of the tested compound). Based on the method of Cheng and Prusoff, K$_i$ was derived from the equation K$_i$=IC$_{50}$/(1+L/K$_d$), where L is the concentration of the radioligand. IC$_{50}$ represents the concentration of the drug causing 50% inhibition of specific radioligand binding, and K$_d$ represents the dissociation constant of the radioligand receptor complex. Data were analyzed by a non-linear least-square curve-fitting procedure using Scientist software (MicroMath Inc., Salt Lake City, Utah).

Determination of pA$_2$ Values

Male guinea pigs weighing about 400 g were obtained from Harlan Inc. (Indianapolis, Ind.) and fasted overnight. Animals were sacrificed by decapitation, and the ileum (the region of 5 cm upward of the cecum) was isolated and removed. The ileum was cut into 2.5 cm pieces and suspended in an organ bath containing 30 mL of mixture of Tyrode's solution and 0.1 mM hexamethonium bromide. The organ bath was constantly aerated with oxygen and kept at 37° C. One end of the ileum strip was attached to a fixed support at the bottom of the organ bath, and the other end to an isometric force transducer (Model TRN001, Kent Scientific Corp., Conn.) operated at 2-10 g range. The ileum strip was kept at a 2 g tension, and carbachol was used as antagonist. The ileum contracted cumulatively upon the addition of consecutive doses of carbachol (10-20 μL of 2×10$^{-4}$-2×10$^{-3}$ M in water solution). Contractions were recorded on a physiograph (Kipp & Zonen Flarbed Recorder, Holland). After the maximum response was achieved, the ileum was washed three times, and a fresh Tyrode's solution containing appropriate concentration of the antagonist (anticholinergic compound tested) was replaced. An equilibration time of 10 min was allowed for the antagonists before the addition of carbachol. In each experiment, 5 to 6 different concentrations were used, and a Schild plot was used to obtain the pA$_2$ values. Four trials were performed for each antagonist.

In Vivo Mydriatic Studies

The mydriatic effects of eight completely resolved zwitterionic isomers were compared to those of glycopyrrolate, tropicamide, (±) 3-(2-cyclopentyl-2-phenyl-2-hydroxyacetoxy)-1-(carboxymethyl)-1-methylpyrrolidinium inner salt

[(±)-GA or Compound (bb)] and (2R) 3-(2-cyclopentyl-2-phenyl-2-hydroxyacetoxy)-1-(carboxymethyl)-1-methylpyrrolidinium inner salt [(2R)-GA or Compound (cc)] in rabbit eyes. Four healthy, male New-Zealand white rabbits weighting about 3.5 kg were used. 100 μL of compound in water solution (pH 6.5) at various concentrations were administered in the eyes. Compound solutions were applied to one eye, and water was applied to the other eye that served as control. Experiments were carried out in a light- and temperature-controlled room. At appropriate time intervals, the pupil diameters of both eyes were recorded. Percent difference in pupil diameters between each time-point and zero time-point were calculated for both treated and control eyes and reported as mydriatic responses. Control eye dilations were monitored to determine whether systemic absorption had occurred or not. The area under the mydriatic response-time curve ($AUC^{eff}$) was calculated by the trapezoidal rule, and it was used to compare the activity and duration of action of the tested compounds.

Statistical Analysis

Receptor binding affinities and $pA_2$ values were compared using student t-tests. Mydriatic activities (maximum response Rmax % and area under the effect curves $AUC_{eff}$) were compared using ANOVA. A significance level of $P<0.05$ was used in all cases.

Results and Discussion

Synthesis

Five soft anticholinergic ester isomers and eight zwitterionic metabolite acid isomers were newly synthesized. The 2R diastereoisomers [Compounds (e), (f), (g), (dd), (ee), (ff) and (gg)] were obtained by the synthetic pathways described below.

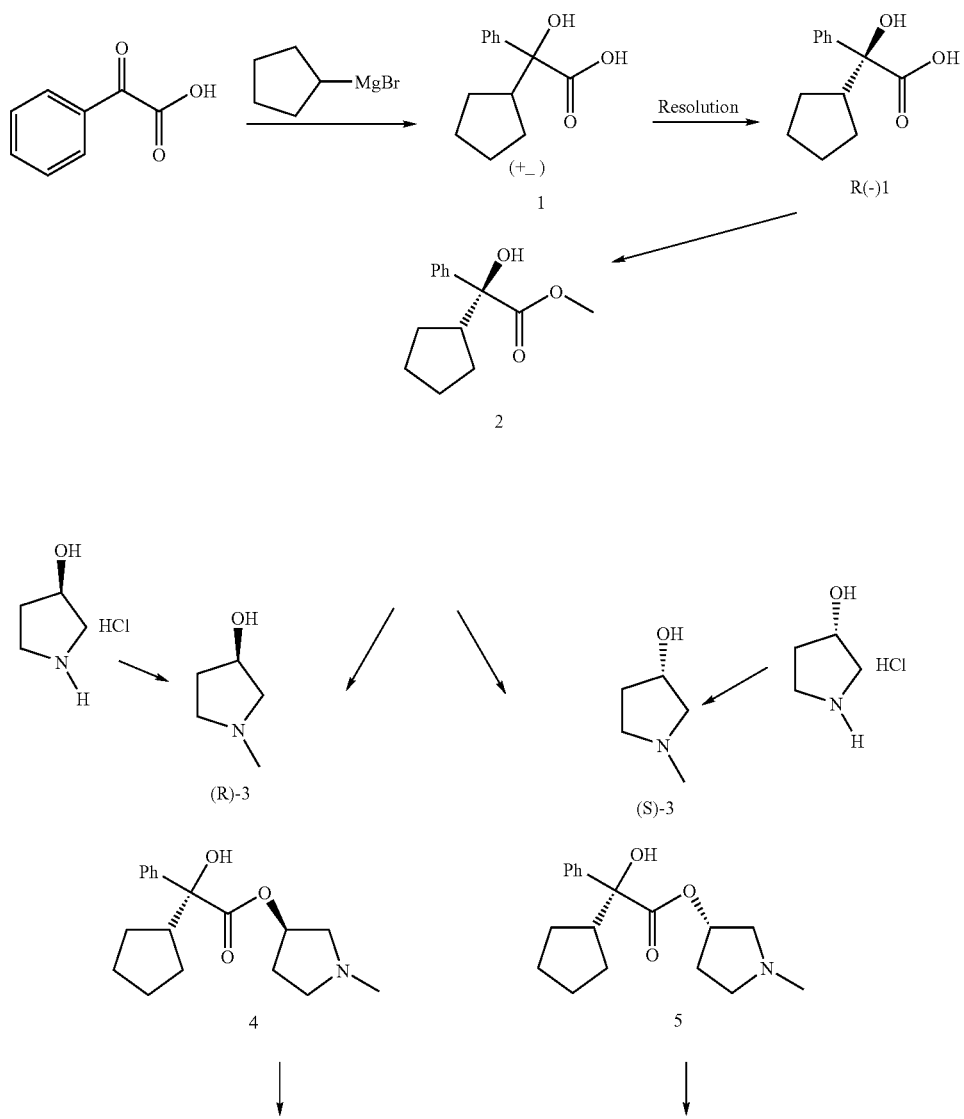

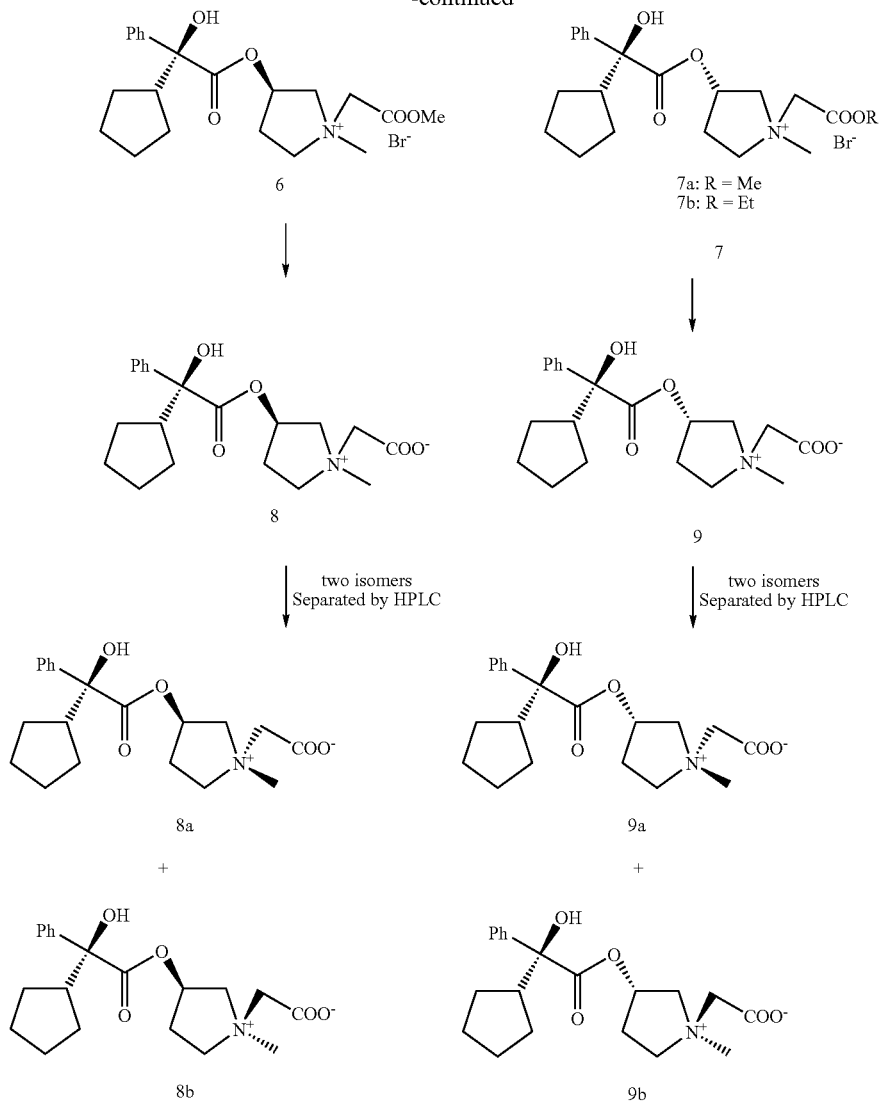

As shown in Scheme 1, first the racemic cyclopentylmandelic acid 1 was synthesized with cyclopentylmagnesium bromide and benzoylformic acid. This racemic acid was resolved by repeated crystallization of the salts produced between this acid and (−)-strychnine. The left rotatory (−22.5°) optically pure free acid R(−)1 was recovered by basification of the salts with sodium hydroxide solution followed by acidification with hydrochloric acid. Methylation of R(−)1 with methyl iodide and potassium carbonate in DMF at room temperature yields methyl 2R(−)cyclopentylmandelate, R(−)2. Transesterfication of R(−)2 with R-3-hydroxy-N-methylpyrrolidine, (R)-3 (made from R-3-hydroxypyrrolidine with paraformaldehyde and formic acid), gave (3R)—N-methyl-3-pyrrolidinyl-2R-cyclopentylmandelate 4; or with S-3-hydroxy-N-methylpyrrolidine (S)-3 (made from S-3-hydroxypyrrolidine with paraformaldehyde and formic acid), gave (3S)—N-methyl-3-pyrrolidinyl-2R-cyclopentyl mandelate 5. Quartemization of 4 and 5 with methyl or ethyl bromoacetate in acetonitrile gave 6 [Compound (e)], 7a [Compound (f)], and 7b [Compound (g)]. Each of these has two diastereoisomers, due to the nitrogen chiral center, with a ratio of 2 to 1 (R:S=2:1) that was shown in 1H NMR spectra.

Hydrolysis of 6 [Compound (e)] and 7a [Compound (f)] gave their zwitterionic inner salts 8 and 9. Each zwitterionic salt also possesses two diastereoisomers with a ratio of 2 to 1 that could be separated by HPLC to give zwitterionic isomers 8a, 8b & 9a and 9b. From 1H NMR, 8a, 8b, and 9a, 9b were evidenced to be pairs of diastereoisomers based on chiral nitrogen. To identify the absolute configuration of these isomers, 8b was chosen and dissolved in CDCl₃ for the investigation of nuclear overhauser effect (NOE). The 2D $^1$H—$^1$H NOESY spectrum showed that the methyl group on the nitrogen was at the same side as the hydrogen at the 3-position of pyrrolidinium ring. Accordingly, the configuration of the nitrogen should be the S form, and the absolute stereochemistry of 8b was proved to be (2R,1'R,3'S) 3-(2-cyclopentyl-2-phenyl-2-hydroxyacetoxy)-1-(carboxymethyl)-1-methylpyrrolidinium inner salt [Compound (ee)]. Therefore, 8a was (2R,1'R,3'R) 3-(2-cyclopentyl-2-phenyl-2-hydroxyacetoxy)-1-(carboxymethyl)-1-methylpyrrolidinium inner salt [Compound (dd)]; 9a was (2R,1'R,3'S) 3-(2-cyclopentyl-2-phenyl-2-hydroxyacetoxy)-1-(carboxymethyl)-1-methylpyrrolidinium inner salt [Compound (ff)]; and 9b was (2R, 1'S,3'S) 3-(2-cyclopentyl-2-phenyl-2-hydroxyacetoxy)-1-(carboxymethyl)-1-methylpyrrolidinium inner salt [Compound (gg)].

Grover and coworkers previously reported [*J. Org. Chem.* 65: 6283-6287 (2000)] the highly stereoselective synthesis of (S)-cyclopentylmandelic acid in five steps starting with (S)-mandelic acid. Modification of their procedure afforded pure S(+)-cyclopentylmandelic acid in three steps with good yield. As depicted in Scheme 2, reaction of S(+)-mandelic acid with pivaldehyde in the presence of the catalyst trifluoromethanesulfonic acid gave the product of cis-(2S,5S)-2-(tert-butyl)-5-phenyl-1,3-dioxolan-4-one, 10, in about 90% yield. At −78° C., deprotonation of 10 with lithium bis(trimethylsilyl)amide followed by adding cyclopentyl bromide generated cis-(2S,5S)-2-(tert-butyl)-5-cyclopentyl-5-phenyl-1,3-dioxolan-4-one, 11. Base hydrolysis of 11 with potassium hydroxide, followed by acidification with hydrochloric acid provided the expected (S)-(+)-cyclopentylmandelic acid 12. After this step, the same procedures as for 8a, 8b, 9a and 9b including methylation, esterification, quaternization and hydrolyses were followed to give the final four zwitterionic isomers, (2S,1'R,3'R) 3-(2-cyclopentyl-2-phenyl-2-hydroxyacetoxy)-1-(carboxymethyl)-1-methylpyrrolidinium inner salt 18a [2S1'R3'R-GA or Compound (hh)]; (2S,1'S,3'R) 3-(2-cyclopentyl-2-phenyl-2-hydroxyacetoxy)-1-(carboxymethyl)-1-methylpyrrolidinium inner salt 18b [2S1'S3'R-GA or Compound (ii)]; (2S,1'R,3'S) 3-(2-cyclopentyl-2-phenyl-2-hydroxyacetoxy)-1-(carboxymethyl)-1-methylpyrrolidinium inner salt 19a [2S1'R3'S-GA or Compound (jj)]; and (2S,1'S,3'S) 3-(2-cyclopentyl-2-phenyl-2-hydroxyacetoxy)-1-(carboxymethyl)-1-methylpyrrolidinium inner salt 19b [2S1'S3'S-GA or Compound (kk)]. They were also characterized by NMR.

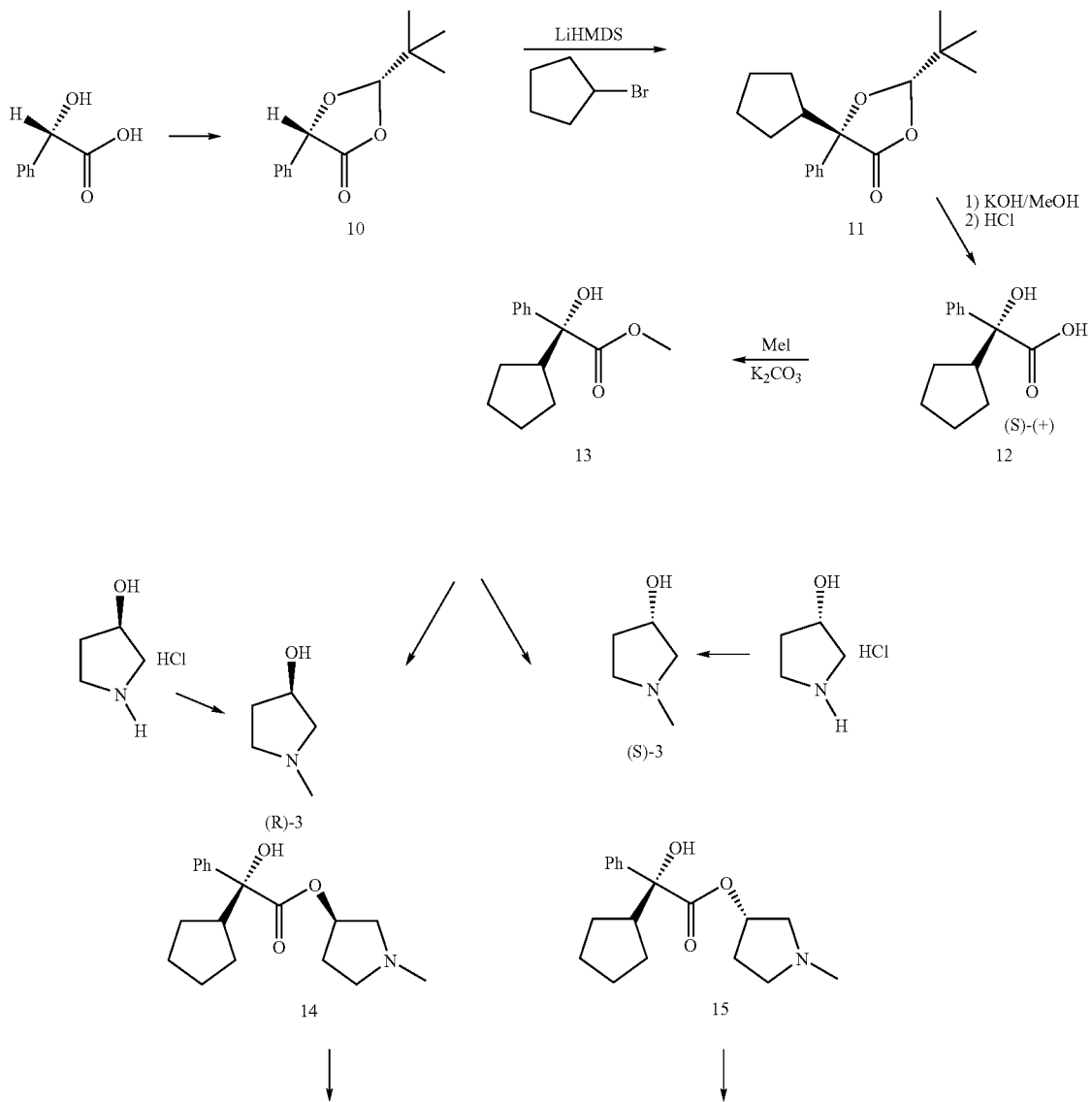

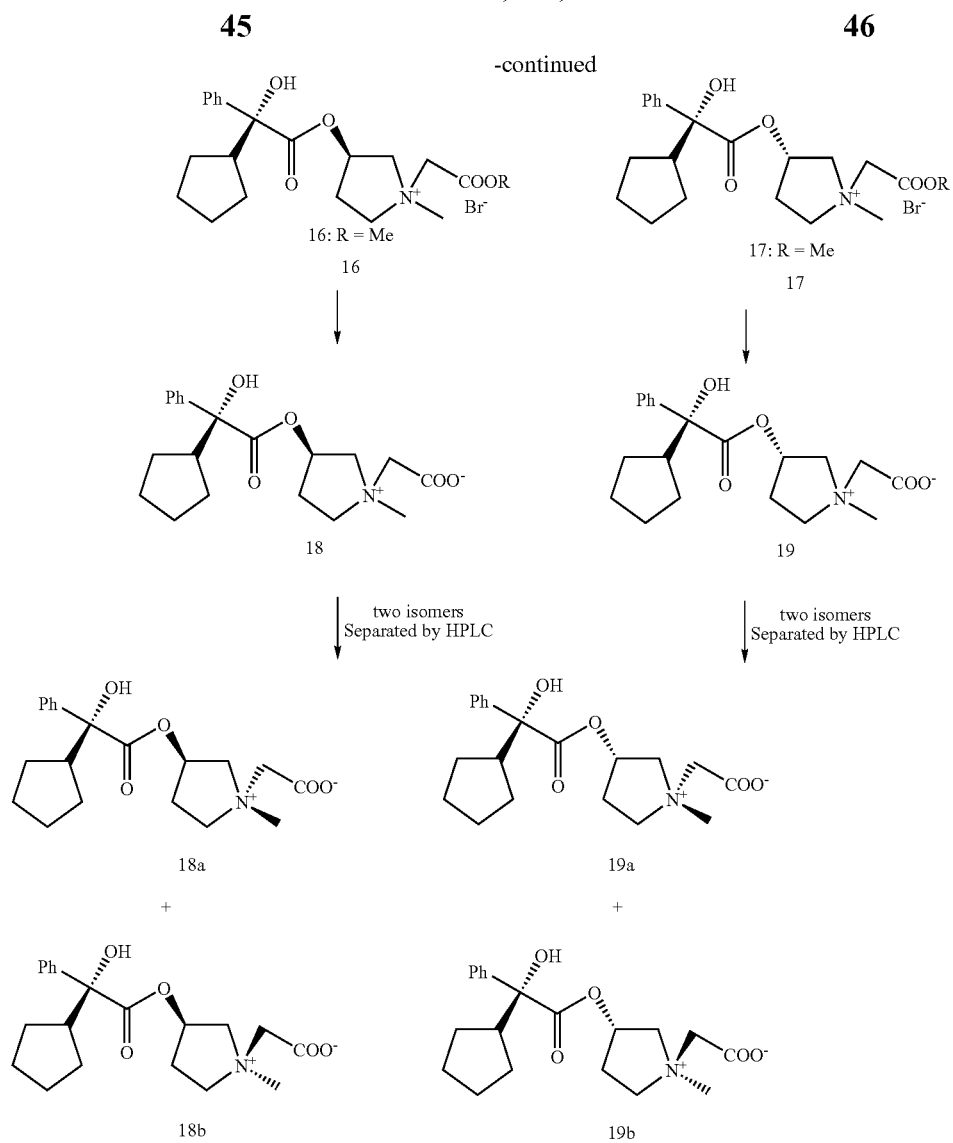

Receptor Binding Studies

The receptor binding affinities of soft analogs, $pK_i$, determined by radioligand binding assays using human cloned muscarinic receptor subtypes, $M_1$-$M_4$, are presented in Table 6.

TABLE 6

Receptor binding affinities, $M_3/M_2$ selectivities, and $pA_2$ values.

| Compound | Subtypes of cloned muscarinic receptors[a] | | | | Selectivity[b] | |
| --- | --- | --- | --- | --- | --- | --- |
| | $M_1$ | $M_2$ | $M_3$ | $M_4$ | $M_3/M_2$ | $pA_2$[c] |
| (a)[d] | 7.91 ± 0.05 | 7.79 ± 0.11 | 7.80 ± 0.10 | 8.29 ± 0.19 | 1.0 ± 0.0 | 7.90 ± 0.13 |
| | (1.02 ± 0.12) | (1.25 ± 0.08) | (1.17 ± 0.18) | (1.12 ± 0.05) | | |
| (b)[d] | 7.51 ± 0.17 | 7.32 ± 0.07 | 7.54 ± 0.15 | 7.94 ± 0.09 | 1.8 ± 0.7 | 7.36 ± 0.34 |
| | (0.91 ± 0.09) | (1.23 ± 0.06) | (1.18 ± 0.08) | (1.18 ± 0.09) | | |
| (bb)[d] | 6.19 ± 0.06 | 5.48 ± 0.13 | 5.84 ± 0.07 | 6.44 ± 0.06 | 2.4 ± 0.7 | 6.42 ± 0.30 |
| | (1.11 ± 0.06) | (1.02 ± 0.20) | (1.01 ± 0.07) | (0.84 ± 0.06) | | |
| (c)[e] | 8.89 ± 0.04 | 8.87 ± 0.05 | 9.00 ± 0.06 | 9.52 ± 0.01 | 1.4 ± 0.2 | 8.31 ± 0.05 |
| | (0.83 ± 0.11) | (1.10 ± 0.11) | (0.83 ± 0.01) | (0.83 ± 0.01) | | |
| (d)[e] | 8.67 ± 0.16 | 8.84 ± 0.34 | 8.74 ± 0.02 | 8.85 ± 0.13 | 1.1 ± 1.1 | 8.55 ± 0.16 |
| | (0.86 ± 0.08) | (0.92 ± 0.01) | (1.09 ± 0.15) | (0.89 ± 0.02) | | |
| (cc)[e] | 8.11 ± 0.16 | 7.48 ± 0.12 | 8.12 ± 0.10 | 8.23 ± 0.12 | 4.4 ± 0.3 | 7.20 ± 0.19 |
| | (1.12 ± 0.25) | (0.95 ± 0.11) | (0.80 ± 0.01) | (1.02 ± 0.10) | | |

TABLE 6-continued

Receptor binding affinities, $M_3/M_2$ selectivities, and $pA_2$ values.

| Compound | Subtypes of cloned muscarinic receptors[a] | | | | Selectivity[b] | |
| --- | --- | --- | --- | --- | --- | --- |
| | $M_1$ | $M_2$ | $M_3$ | $M_4$ | $M_3/M_2$ | $pA_2$[c] |
| (e)[f] | 8.99 ± 0.04 | 9.01 ± 0.06 | 9.06 ± 0.14 | 9.45 ± 0.01 | 1.1 ± 0.1 | — |
| | (1.19 ± 0.12) | (1.03 ± 0.09) | (1.03 ± 0.18) | (1.52 ± 0.66) | | |
| (f)[f] | 8.50 ± 0.03 | 7.90 ± 0.04 | 8.60 ± 0.09 | 8.87 ± 0.09 | 5.0 ± 1.1 | —[h] |
| | (1.30 ± 0.20) | (1.07 ± 0.17) | (1.04 ± 0.27) | (1.08 ± 0.01) | | |
| (h)[f] | 7.23 ± 0.01 | 7.22 ± 0.03 | 6.99 ± 0.08 | 7.57 ± 0.01 | 0.6 ± 0.1 | — |
| | (0.98 ± 0.06) | (1.09 ± 0.18) | (1.15 ± 0.13) | (1.11 ± 0.03) | | |
| (i)[f] | 6.40 ± 0.05 | 6.47 ± 0.08 | 5.95 ± 0.02 | 6.39 ± 0.01 | 0.3 ± 0.0 | — |
| | (0.92 ± 0.09) | (0.99 ± 0.16) | (1.06 ± 0.03) | (1.44 ± 0.75) | | |
| (j)[f] | 8.68 ± 0.11 | 8.21 ± 0.10 | 8.64 ± 0.07 | 8.71 ± 0.38 | 2.8 ± 0.8 | — |
| | (1.21 ± 0.33) | (1.27 ± 0.11) | (1.33 ± 0.16) | (1.15 ± 0.03) | | |
| (dd)[g] | 7.04 ± 0.09 | 6.43 ± 0.07 | 6.95 ± 0.04 | 7.00 ± 0.05 | 3.5 ± 0.2 | 6.32 ± 0.23 |
| | (0.97 ± 0.13) | (0.85 ± 0.21) | (1.06 ± 0.04) | (0.93 ± 0.01) | | |
| (ee)[g] | 8.13 ± 0.06 | 7.63 ± 0.02 | 8.15 ± 0.02 | 8.33 ± 0.04 | 3.3 ± 0.0 | 7.45 ± 0.21 |
| | (1.25 ± 0.01) | (0.82 ± 0.15) | (0.84 ± 0.17) | (1.00 ± 0.06) | | |
| (ff)[g] | 7.98 ± 0.01 | 7.39 ± 0.09 | 8.04 ± 0.01 | 8.15 ± 0.06 | 5.2 ± 0.7 | 7.33 ± 0.28 |
| | (1.02 ± 0.03) | (0.80 ± 0.22) | (0.96 ± 0.03) | (1.01 ± 0.06) | | |
| (gg)[g] | 8.32 ± 0.04 | 7.64 ± 0.01 | 8.46 ± 0.12 | 8.56 ± 0.07 | 5.5 ± 1.1 | 7.15 ± 0.12 |
| | (1.01 ± 0.01) | (1.00 ± 0.04) | (0.80 ± 0.21) | (0.86 ± 0.06) | | |
| (hh)[g] | 5.87 ± 0.04 | 5.65 ± 0.06 | 5.54 ± 0.16 | 5.79 ± 0.12 | 0.8 ± 0.1 | 5.14 ± 0.38 |
| | (1.06 ± 0.05) | (1.24 ± 0.07) | (1.02 ± 0.12) | (0.88 ± 0.04) | | |
| (ii)[g] | 6.67 ± 0.06 | 6.35 ± 0.01 | 6.22 ± 0.05 | 6.47 ± 0.01 | 0.7 ± 0.0 | 5.69 ± 0.13 |
| | (1.08 ± 0.03) | (1.01 ± 0.01) | (1.04 ± 0.08) | (1.30 ± 0.28) | | |
| (jj)[g] | <4.5 | <4.5 | <4.5 | <4.5 | — | <4 |
| | — | — | — | — | | |
| (kk)[g] | 5.84 ± 0.06 | 5.61 ± 0.00 | 5.61 ± 0.09 | 5.85 ± 0.05 | 1.0 ± 0.2 | 5.03 ± 0.26 |
| | (1.13 ± 0.10) | (1.20 ± 0.02) | (1.03 ± 0.01) | (0.95 ± 0.18) | | |
| glycopyrrolate | 9.76 ± 0.05 | 9.19 ± 0.18 | 8.73 ± 0.05 | 9.90 ± 0.08 | 0.4 ± 0.2 | 8.57 ± 0.12 |
| | (1.37 ± 0.20) | (0.99 ± 0.11) | (1.14 ± 0.25) | (1.02 ± 0.01) | | |
| scopolamine methyl bromide | 9.69 ± 0.01 | 9.18 ± 0.21 | 9.29 ± 0.12 | 9.92 ± 0.21 | 1.3 ± 0.4 | 9.16 ± 0.19 |
| | (0.92 ± 0.10) | (1.02 ± 0.02) | (1.07 ± 0.01) | (0.90 ± 0.04) | | |

[a]Receptor binding at cloned human muscarinic receptors ($M_1$-$M_4$ subtypes); $pK_i$ data represent mean ± SD of 3 experiments, and the numbers in parentheses denote Hill slopes.
[b]$M_3/M_2$ affinity ratio (times)
[c]$pA_2$ values were determined on 4-6 ileum strips obtained from different animals, and data represent mean ± SD.
[d]Racemic forms.
[e]Isomers based on the chiral center 2.
[f]Isomers based on the chiral centers 2 & 3'.
[g]Isomers based on the chiral centers 2, 3', & 1'.
[h]Data not available or not detectable.

The $pK_i$ of newly synthesized isomers were compared with that of the racemic and 2R isomeric parent soft drugs [the methyl ester Compound (c) and the ethyl ester Compound (d)], racemic and 2R isomeric GA (the zwitterionic metabolite), i.e, Compounds (bb) and (cc), as well as those of glycopyrrolate and N-methylscopolamine. $pK_i$ of the racemic forms, Compound (a) and Compound (b), showed lower receptor binding affinities than their corresponding 2R isomers (7.8-8.3 vs. 8.7-9.5), confirming that stereospecificity is important at these receptors. The potencies of these 2R isomers are similar to those of glycopyrrolate (8.7-9.9) and N-methylscopolamine (9.2-9.9). Resolution of 2 and 3' chiral centers of racemic Compound (a) resulted in four stereoisomers, Compounds (e), (f), (h) and (i) with $pK_i$ values of 9.0-9.5, 7.9-8.9, 7.0-7.6 and 6.0-6.5, respectively. These numbers indicate that among the methyl ester isomers, not only 2R isomers are more potent than the corresponding 2S isomers, but also that 3'R isomers are more potent than 3'S isomers. The 2R3'S isomer of the ethyl ester, Compound (j), showed a $pK_i$ value of 8.2-8.7, the same as the 2R3'S isomer of the methyl ester. In the same table, the $M_3/M_2$ muscarinic-receptor subtype-selectivities were also calculated. Contrary to the previously reported 2R isomer of the methyl and ethyl esters, Compounds (c) and (d), that show no $M_3/M_2$ subtype selectivity, the 2R3'S isomers of the methyl and ethyl esters, Compounds (e) and (j), show significantly increased $M_3/M_2$ muscarinic-receptor subtype-selectivity ($p<0.01$, t-test assuming equal variances). The $M_3$ affinity was 5.0±1.1 times of $M_2$ affinity in the case of Compound (e), and 2.8±0.8 times in the case of Compound (j). This indicates that the configuration of chiral center 3' may play an important role in the safety profile of this type of soft anticholinergics.

The receptor-binding $pK_i$ of racemic (±) GA, i.e., Compound (bb), and isomeric 2R-GA, i.e., Compound (cc), obtained earlier are also shown in Table 6. In agreement with soft drug design principles that the acidic moiety formed by hydrolysis of the parent soft drug ester inactivates the drug, the zwitterions were (±)GA or Compound (bb), 5.5-6.4, vs. Compound (a), 7.8-8.3, and Compound (b), 7.3-7.9; and $pK_i$ of 2R-GA or Compound (cc), 7.5-8.2, vs. Compound (c), 8.9-9.5, and Compound (d), 8.7-8.9 (3-4). As discussed previously, the zwitterionic metabolite retains some activity because the electronic distribution in its structures somewhat resembles those of the neutral, active anticholinergics. In this study, to obtain a better picture of the stereospecificity/stereoselectivity of this type of anticholinergic, the zwitterionic form was chosen as a model compound for the investigation, since the zwitterion GA, either in its racemic or its 2R isomeric form, was very soluble and stable in aqueous solutions (buffer or biological media, pH 6-8). In addition, 2R-GA [Compound (cc)] has been found active at topical sites (e.g. in rabbit eyes), and could be excreted unchanged, rapidly through urine ($t_{1/2}$ 10-15 min after i.v. in rats). In Table 6, the $pK_i$ of the completely resolved eight isomers of ±GA [Compound (bb)], 2R1'R3'R-GA [Compound (dd)], 2R1'S3'R-GA [Compound (ee)], 2R1'R3'S-GA [Compound (ff)], 2R1'S3'S-GA [Compound (gg)], 2S1'R3'R-GA [Compound (hh)], 2S1'S3'R-GA [Compound (ii)], 2S1'R3'S-GA [Compound (jj)], 2S1'S3'S-GA [Compound (kk)] was in a wide range of 4.5-8.6. In all cases, the 2R isomers are more potent than the 2S isomers, and the 1'S isomers are more potent than the 1'R isomers. The comparative potencies for 3'R and 3'S isomers varied depending on the configuration of chiral center 2, e.g. 2R1'R3'S>2R1'R3'R and 2R1'S3'S>2R1'S3'R; but 2S1'R3'R>2S1'R3'S and 2S1'S3'R>2S1'S3'S. Also, the same as previous methyl ester isomers, among 2R isomers of the acid, the 2R3'S isomers (2R1'R3'S and 2R1'S3'S) showed highest $M_3/M_2$ muscarinic-receptor subtype-selectivities (5.2-5.5 times) followed by the 2R3'R isomers (2R1'R3'R and 2R1'S3'R, 3.3-3.5 times). The 2S isomers did not show any $M_3/M_2$ selectivity. Thus, the importance of the chiral center 2 and 3' configuration (2R3'S) on the $M_3/M_2$ selectivity of this type of anticholinergics has been demonstrated.

In order to show the comparative stereoselectivity (times) based on each chiral center, the ratio of binding activities of each corresponding paired isomers was calculated, and the results are shown in Table 7. The results displayed are comparative potencies (times) calculated from the receptor binding affinities, $pK_i$, in Table 6. The difference in receptor binding affinities between 2R and 2S isomers is significant (27 to 447 times for the methyl ester isomers, and 6 to 4467 times for zwitterion isomers). The 3'R isomers of the methyl ester (with chiral center 1 unresolved, 2R3'R & 2S3'R methyl esters) are more active (1.5 to 12.9 times) than their corresponding 3'S isomers (2R3'S & 2S3'S methyl esters). However, in the acid, the 3'S isomers were not always more active than the corresponding 3'R isomers, e.g. in 2R isomers, 3'S>3'R (2R1'R3'S>2R1'R3'R and 2R1'S3'S>2R1'S3'R); but in 2S isomers, 3'R>3'S (2S1'R3'R>2S1'R3'S and 2S1'S3'R>2S1'S3'S). Also, there are more significant differences between 2R1'R3'S and 2R1'R3'R than between 2R1'S3'S and 2R1'S3'R (8.7 to 14.1 times vs. 1.0 to 2.0 times), and between 2S1'R3'R and 2S1'R3'S than between 2S1'S3'R and 2S1'S3'S (11.0 to 23.4 times vs. 4.1 to 6.8 times). These results indicate that the activity based on chiral center 3' can be affected by the configuration of the other two chiral centers, 2 and 1'. When comparing all eight zwitterion isomers (with all three chiral centers resolved), it clearly shows that 1'S isomers were more active than the corresponding 1'R isomers in all cases (1.8-22.4 times).

TABLE 7

Comparative stereoselectivities[a]

| Compound | Subtypes of cloned muscarinic receptors[b] | | | | Description[f] |
|---|---|---|---|---|---|
| | $M_1$ | $M_2$ | $M_3$ | $M_4$ | |
| Methyl Esters | | | | | |
| 2R3'S/2S3'S[c] | 125.9 | 26.9 | 446.7 | 302.0 | 2R > 2S |
| 2R3'R/2S3'R[c] | 57.5 | 61.7 | 117.5 | 75.9 | |
| 2R3'R/2R3'S[d] | 3.1 | 12.9 | 2.9 | 3.8 | 3R > 3S |
| 2S3'R/2S3'S[d] | 6.8 | 5.6 | 11.0 | 1.5 | |
| Zwitterions | | | | | |
| 2R1'R3'R/2S1'R3'R[c] | 14.8 | 6.0 | 25.7 | 16.2 | 2R >> 2S |
| 2R1'S3'R/2S1'S3'R[c] | 28.8 | 19.1 | 85.1 | 72.4 | |
| 2R1'R3'S/2S1'R3'S[c] | 3020.0 | 776.2 | 3467.4 | 4466.8 | |
| 2R1'S3'S/2S1'S3'S[c] | 302.0 | 107.2 | 707.9 | 512.9 | |
| 2R1'R3'S/2R1'R3'R[d] | 8.7 | 9.1 | 12.3 | 14.1 | 3S > 3R |
| 2R1'S3'S/2R1'S3'R[d] | 1.5 | 1.0 | 2.0 | 1.7 | |

TABLE 7-continued

Comparative stereoselectivities[a]

| Compound | Subtypes of cloned muscarinic receptors[b] | | | | Description[f] |
|---|---|---|---|---|---|
| | $M_1$ | $M_2$ | $M_3$ | $M_4$ | |
| 2S1'R3'R/2S1'R3'S[d] | 23.4 | 14.1 | 11.0 | 19.5 | 3R > 3S |
| 2S1'S3'R/2S1'S3'S[d] | 6.8 | 5.5 | 4.1 | 4.2 | |
| 2R1'R3'R/2R1'R3'R[e] | 12.3 | 15.8 | 15.8 | 21.4 | 1R < 1S |
| 2R1'S3'S/2R1'R3'S[e] | 2.2 | 1.8 | 2.6 | 2.6 | |
| 2S1'S3'R/2S1'R3'R[e] | 6.3 | 5.0 | 5.2 | 4.8 | |
| 2S1'S3'S/2S1'R3'S[e] | 21.9 | 12.9 | 12.9 | 22.4 | |

[a]Affinity ratio (times) between each two isomers based on each of the three different chiral centers.
[b]Receptor binding at cloned human muscarinic receptors ($M_1$-$M_4$ subtypes)
[c]Affinity ratio based on the chiral center 2.
[d]Affinity ratio based on the chiral center 3.
[e]Affinity ratio based on the chiral center 1.
[f]Concluded stereoselectivities In all cases, the Hill coefficients (n) were not very different from unity indicating that, in general, drug-receptor interactions obeyed the law of action and binding took place at only one site.

$pA_2$ Studies

The $pA_2$ values determined from guinea pig ileum contraction assays, which represent the negative logarithm of the molar concentration of the antagonist that produces a two-fold shift to the right in an agonist's concentration-response curve, are a classical functional study of anticholinergic affinity (at $M_3$ muscarinic receptors). For the soft anticholinergics of the present study, the $pA_2$ values obtained from ileum longitudinal contractions by using carbachol as agonist with the method of van Rossum [*Arch. Int. Pharcodyn.* 143: 299-330 (1963)] are presented in Table 6. The $pA_2$ values are in general, comparable to the $pK_i$ values obtained in the $M_3$ receptor binding studies. The $pA_2$ values of newly developed zwitterionic isomers significantly differed between 2R and 2S configurations (6.32 to 7.45 and <4 to 5.69, respectively, p<0.01, t-test assuming equal variances). Similar to the above reported 2R isomer (2R-GA), the $pA_2$ values of completely resolved 2R isomers (2R1'R3'R-GA, 2R1'S3'R-GA, 2R1'R3'S-GA, and 2R1'S3'S-GA) are 1 to 2 less than those of the corresponding 2R ethyl and methyl parent ester soft drugs, indicating a one to two order of magnitude less activity of these zwitterionic compounds. The retained moderate activity of some zwitterionic metabolite isomers is probably due to a spatially-close structures that resembles those of the neutral, active anticholinergics. In the active 2R isomers, while 2R1'R3'R-GA showed a lower value (6.32), all others showed a similar moderate contraction activity (about 7.15 to 7.45).

Mydriatic Activities

The mydriatic effects of the fully resolved eight zwitterionic isomers were compared to those of (±)GA, 2R-GA, glycopyrrolate and tropicamide in vivo in rabbits. Following a 100 μl topical administration, the mydriatic responses were recorded at appropriate time-intervals as % changes in pupil size. The maximum response ($R_{max}$, % change in pupil size at 30 min to 1 h after administration) and area under the response-time curve ($AUC^{eff}_{0-168h}$) are shown in Table 8.

TABLE 8

Maximum response ($R_{max}$, maximum % change in pupil size) and area under the response-time curve ($AUC_{eff}$) after topical administration (0.1 mL).[a]

| Compound | Conc. (%) | $R_{max}$ (%) | $AUC^{eff}_{0-168\,h}$ |
|---|---|---|---|
| (±)GA[b] [Cpd (bb)] | 0.01 | 1.85 ± 2.14 | 0.7 ± 0.9 |
| | 1 | 45.37 ± 8.19 | 119 ± 34 |
| 2R-GA[b] [Cpd (cc)] | 0.01 | 31.00 ± 7.14 | 73 ± 24 |
| | 0.1 | 50.34 ± 7.92 | 182 ± 40 |
| 2R1'R3'R-GA [Cpd (dd)] | 0.1 | 24.40 ± 8.33 | 89 ± 50 |
| 2R1'S3'R-GA [Cpd (ee)] | 0.1 | 51.79 ± 16.62 | 308 ± 106 |
| 2R1'R3'S-GA [Cpd (ff)] | 0.1 | 43.90 ± 7.63 | 216 ± 29 |
| 2R1'S3'S-GA [Cpd (gg)] | 0.1 | 47.32 ± 19.64 | 274 ± 134 |
| 2S1'R3'R-GA [Cpd (hh)] | 0.1 | 0.00 ± 0.00 | 0 ± 0 |
| | 0.4 | 7.44 ± 0.60 | 11 ± 1 |
| 2S1'S3'R-GA [Cpd (ii)] | 0.1 | 3.87 ± 4.49 | 13 ± 15 |
| | 0.4 | 14.88 ± 1.19 | 37 ± 3 |
| 2S1'R3'S-GA [Cpd (jj)] | 0.1 | 0.00 ± 0.00 | 0 ± 0 |
| | 0.4 | 0.00 ± 0.00 | 0 ± 0 |
| 2S1'S3'S-GA [Cpd (kk)] | 0.1 | 3.87 ± 4.49 | 13 ± 15 |
| | 0.4 | 11.01 ± 3.81 | 28 ± 2 |
| glycopyrrolate[b] | 0.05 | 48.73 ± 12.66 | 2476 ± 847 |
| | 0.1 | 52.95 ± 10.93 | 3732 ± 866 |
| tropicamide[b] | 0.5 | 44.64 ± 11.17 | 451 ± 121 |

[a]Data represent mean ± SD of four trials.
[b]Data adapted from other testing.

Figure 6:
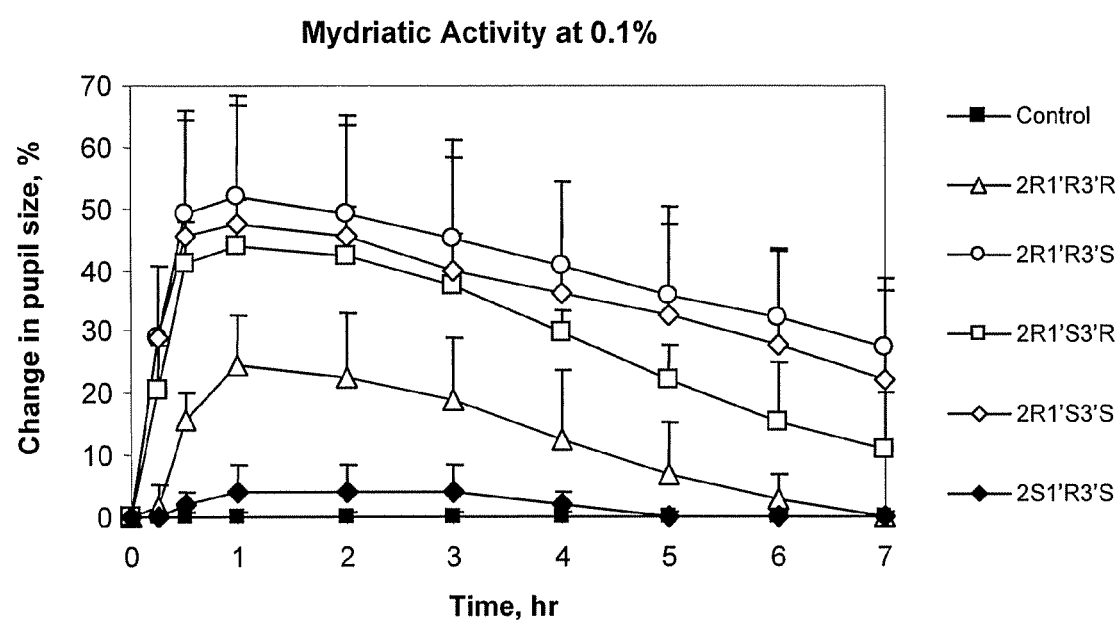
FIG. 6 is a graph of mydriatic activities of various zwitterionic isomers at 0.1% concentrations over a seven hour period.
Figure 7:
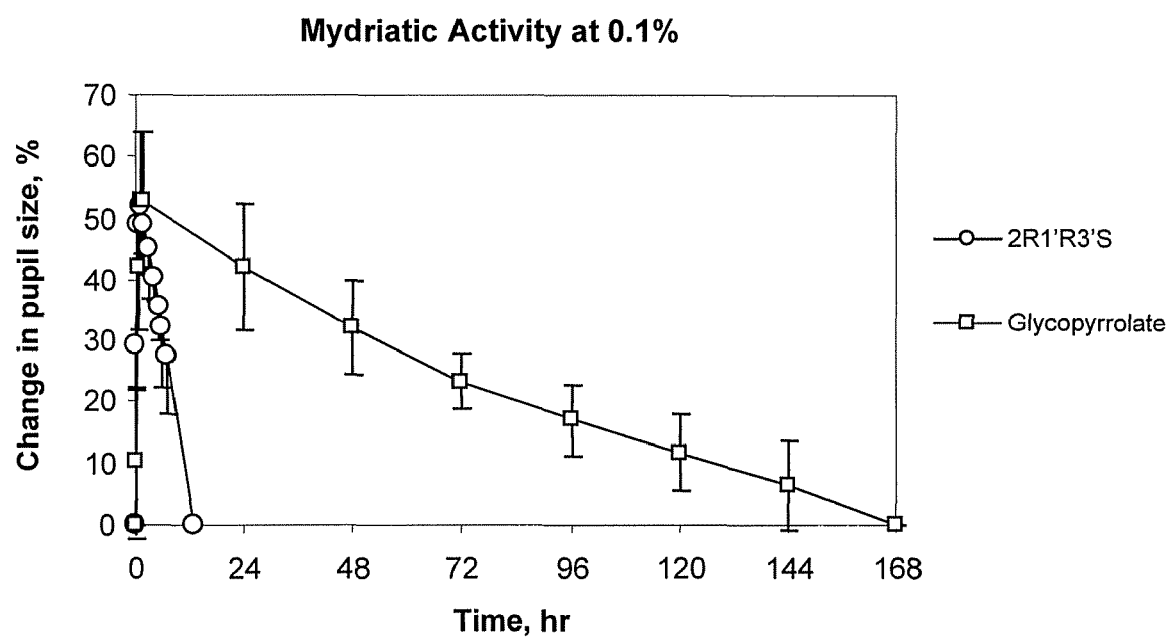
FIG. 7 is a graph comparing the mydriatic activity of the most active zwitterionic isomers with glycopyrrolate at 0.1% concentrations.

The results indicate that, as in the in vitro studies, the 2R isomers are much more potent than the 2S isomers (even when the 2S dose was increased to 0.4%); and 2R1'R3'R-GA is less potent than the other three 2R isomers. In FIG. 6, the activity-time profiles of four 2R and one 1'S isomers (the most active S isomer) at 0.1% are displayed. The pupil-dilating potency of the most potent three 2R isomers at a dose of 0.1% is similar to that of 0.05 to 0.1% of glycopyrrolate and 0.5% of tropicamide, however, their duration of actions was much shorter than that of the "hard" glycopyrrolate (AUC 200-300 vs. 2500, respectively), and somewhat shorter than that of tropicamide, in agreement with soft drug design principles. The activities of 2R1'S3'R-GA (the most active zwitterionic isomer) and glycopyrrolate lasted for 10 h and 144 h, respectively, as displayed in FIG. 7. These results indicate that a good pharmacological effect can be achieved by some 2R zwitterionic isomers, and these isomers can be rapidly eliminated from the body. Furthermore, the active 2R zwitterionic isomers did not cause any observable irritation reactions, such as eye-closing, lacrimation, mucous discharge as well as change in the intraocular pressure during the topical applications; and unlike other conventional anticholinergics, these 2R zwitterionic isomers did not induce dilation of the pupil in the contralateral (water-treated) eyes, indicating no or low systemic side-effects. Therefore, these soft drugs are safe, promising short acting anticholinergics with the possibility of largely reduced unwanted side effects.

Conclusion

Isomers of N-substituted soft anticholinergics based on glycopyrrolate, the methyl and ethyl esters, and their zwitterionic metabolite were synthesized and separated. Their pharmacological activities were evaluated in vitro and in vivo. The receptor binding ($pK_i$) results indicate that stereo-specificity and stereo-selectivity are very important in these soft anticholinergics. There were three chiral centers presented in the structure of these compounds. The most significant improvement of the receptor binding activity was observed in 2R configuration, followed by 1'S. The activities of 3'R and 3'S could be affected by the configurations of the other two chiral centers. The improvement of $M_3/M_2$ muscarinic-receptor subtype-selectivity was found most significant in 2R3'S configurations followed by 2R3'R. The configuration of chiral center 1' showed no effect on $M_3/M_2$ muscarinic-receptor subtype-selectivity. Comparable results obtained from guinea pig ileum assays ($pA_2$), and rabbit mydriasis test on zwitterionic isomers further confirmed the stereo-specificity of these anticholinergics. The pharmacological potency of eight zwitterionic isomers was determined to be 2R1'S3'S=2R1'S3'R=2R1'R3'S>2R1'R3'R>2S1'S3'R>2S1'S 3'S=2S1'R3'R>2S1'R3'S (student t-test, p<0.05). When topically administered (0.1%) in rabbit eyes, some 2R-zwitterion isomers (2R1'S3'S, 2R1'S3'R and 2R1'R3'S) showed similar mydriatic potencies to that of glycopyrrolate and tropicamide, however, their mydriatic effects were of considerably shorter duration, and they did not induce dilation of the pupil in the contralateral, water-treated eyes, indicating that, in agreement with their soft nature, they are locally active, but safe and have a low potential to cause systemic side effects. The usefulness and safety of these glycopyrrolate-based soft anticholinergics have been therefore further proved.

Synthesis and Biological Testing of Tiotropium Derivatives

Structure of the Compounds

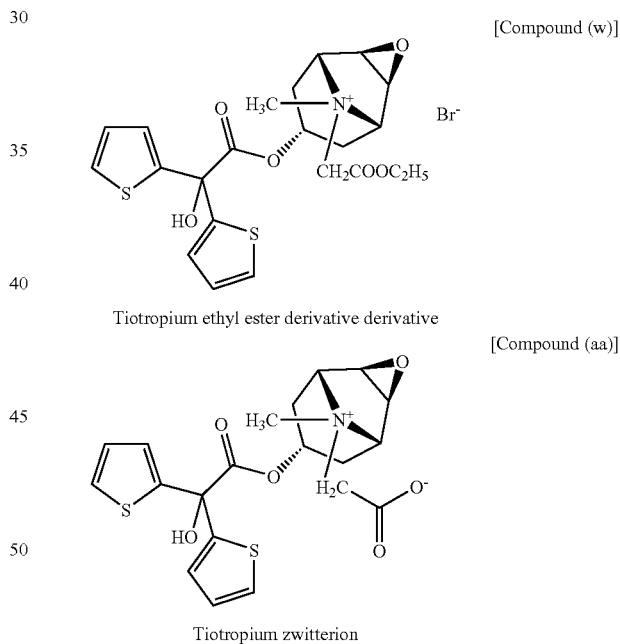

Tiotropium ethyl ester derivative derivative [Compound (w)]

Tiotropium zwitterion [Compound (aa)]

b) Synthesis of a New Tiotropium Analog

By following the inactive metabolite approach, a metabolically sensitive ester function was introduced into the tiotropium molecule resulting in a new soft anticholinergic analog. Intermediate XIII was prepared by the known Grignard reaction of dimethyl oxalate with 2-thienylmagnesium bromide (XII, see Scheme 3 below). Compound XIII was then submitted to known transesterification with scopine (XIV) catalyzed by sodium metal giving the corresponding ester XV. Finally, quaternization with ethyl bromoacetate gave the target compound II (R=Et).

2-Thienylmagnesium bromide was prepared in the usual manner from magnesium and 2-bromothiophene in ether. Scopine (XIV) was obtained from scopolamine hydrobromide by treatment with sodium borohydride in ethanol in moderate yield as described in GB 1,469,781 (1974).

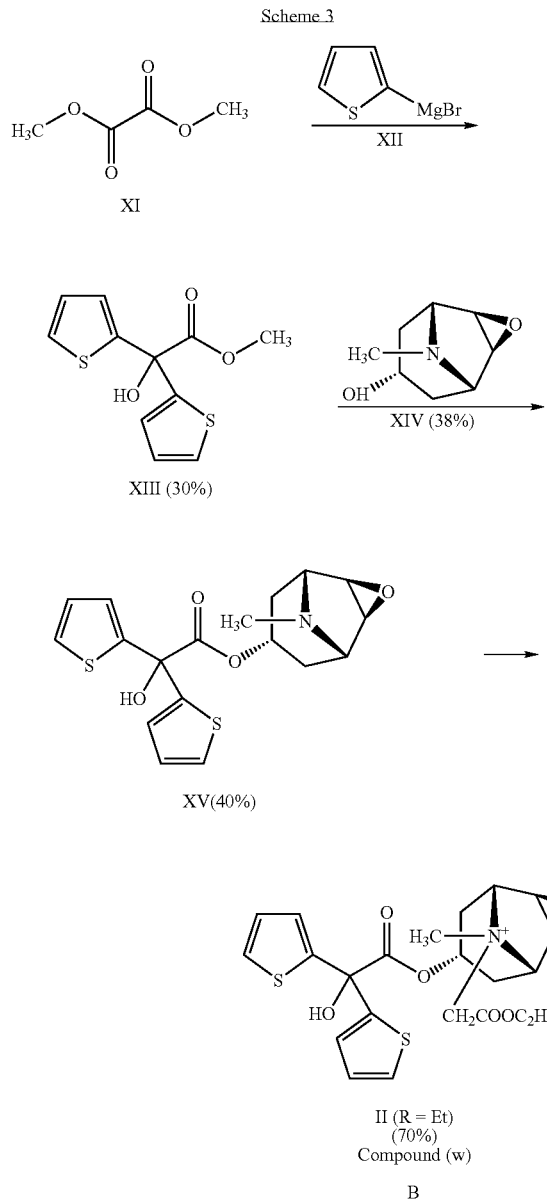

The above synthesis of the soft tiotropium bromide analog leads to a single isomer in a yield of 70%. Tlc indicated no further new component in the reaction mixture of the final quaternization step and it could be shown by NMR (two dimensional ROESY technique) that the ethoxycarbonylmethyl group is in proximity to the oxirane ring. This finding is somewhat surprising as the other isomer with N-methyl pointing toward the oxirane ring would be sterically less crowded.

Stereochemistry of Compound (w) obtained by two-dimensional ROESY experiment:

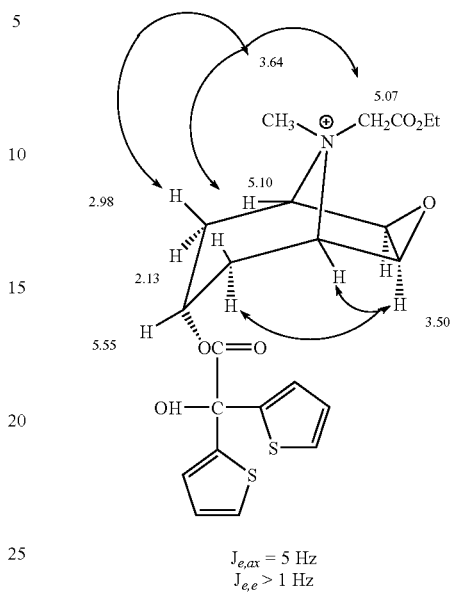

$J_{e,ax} = 5$ Hz
$J_{e,e} > 1$ Hz

The numbers denote $^1$H chemical shifts and coupling constants, the double arrows indicate steric proximities.

Preparation of 6β,7β-epoxy-3β-hydroxy-8-ethoxycarbonylmethyl-8-methyl-1αH,5αH-tropanium bromide, di-2-thienylglycolate, Compound (w)

The scopine ester, represented by formula XV in Scheme 3 above, was prepared as described above, or by conventional methods as described in EP418716 (equivalent to U.S. Pat. No. 5,610,163). Then the scopine ester (70 mg, 0.18 ml) is dissolved in 2 ml of acetone. Ethyl bromocetate (150 microliters, 0.45 mM) is added and the mixture is allowed to react at 20° C. for eight days. The solvent is evaporated in vacuo, 8 ml of water is added and the organic material is extracted with chloroform. The desired quaternary salt is in the aqueous phase and is obtained by lyophilization. Yield 70 mg (70%). Melting point: 115° C. Thin layer chromotography on $Al_2O_3$: $R_f$=0.3 ($CHCl_3$—$CH_3OH$, 4:1) (3 times 4 ml). The product, Compound (w), has the structural formula II shown in Scheme 3 above.

Preparation of 6β,7β-epoxy-3β-hydroxy-8-methyl-8-(2,2,2-trichloroethoxycarbonylmethyl)-1αH,5αH-tropanium bromide, di-2-thienylglycolate, Compound (x)

To the scopine ester XV (0.5 mM) in 3 ml of anhydrous acetonitrile, 1.5 mM of trichloroethyl bromoacetate was added. The mixture was stirred under argon for three days and the acetonitrile was removed under reduced pressure. To the oily residue, 15 ml of water was added and extracted with chloroform (3 times 5 ml). The aqueous solution was lyophilized to give the product as a white solid. Yield: 257 mg (79%). Melting point 105° C., $R_f$=0.65 ($CHCl_3$—$CH_3OH$, 4:1). The product has the structural formula:

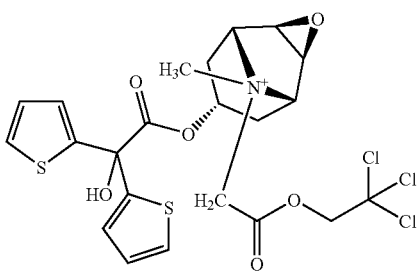

Preparation of 6β,7β-epoxy-3β-hydroxy-8-carboxymethyl-8-methyl-1αH,5αH-tropanium, di-2-thienylglycolate inner salt, Compound (aa)

A suspension of 0.35 mM Compound (x) and Zn dust (0.6 mM) in acetic acid (1.5 ml) was stirred for 3 hours. To that mixture, water (2 ml) and chloroform (2 ml) were added and filtered. The solvents were evaporated in vacuo, 3 ml of water was added and the solution was lyophilized. The crude product was dissolved in methanol (2 ml) and purified by chromatography on Sephadex LH-20. The resulting oil was dissolved in methanol (2 ml) and precipitated with ethyl acetate (1 ml) to give the solid product, Compound (aa). Yield 67 mg (38%), melting point 158-165° C. (decomp). $R_f$=0.45 (CHCl$_3$—CH$_3$OH 4:1) on aluminum oxide. The

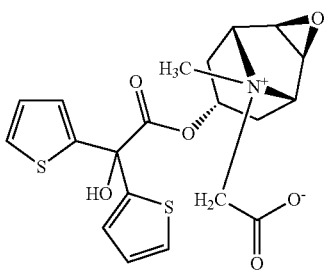

product has the structural formula:
Pharmacology
1: Receptor Binding Assay

Evaluation of the affinity of the compound was made using [$^3$H]QNB as ligand and rat cortical membrane preparation as a source of the receptor. The ethyl ester Compound (w) bound to the muscarinic receptors (mainly M$_1$ in this preparation) with high affinity (Table 9) although this affinity was several-fold lower than those of the reference compounds. The steep Hill slope close to unity indicates the antagonistic nature of its action. Compound (aa) can be evaluated similarly.

TABLE 9

Affinities of tiotropium ethyl ester derivative [Compound (w)] and reference compounds for muscarinic receptors

| Compounds | $K_i$ (nM) | Hill slope | Number of exps. |
|---|---|---|---|
| Atropine | 1.9 ± 0.2 | −1.10 ± 0.04 | 4 |
| Glycopyrrolate | 0.8 ± 0.10 | −1.07 ± 0.03 | 4 |
| Compound (w) | 7.2 ± 0.5 | −1.00 ± 0.04 | 4 |

The $K_i$ values are for inhibition of [$^3$H]QNB binding to rat brain cortex membranes. Values are the mean ± S.E.M. of at least three experiments run in duplicate.

2: Experiments with Isolated Organs

In isolated organ experiments the measurement of antimuscarinic effect of Compound (w) was carried out using guinea pig tracheal ring preparations, where smooth muscle contraction is mediated primarily by muscarinic M$_3$ cholinoceptors although activation of M$_2$-receptors also plays a role in the developing contraction. Compound (w) showed excellent activity in this test; it was more active than atropine and only slightly less effective than ipratropium bromide (Table 10). Compound (aa) can be tested similarly.

TABLE 10

Schild-plot analysis of the antagonism against carbachol in isolated tracheal rings of guinea pigs.

| Antagonist | pA$_2$ | Slope ± S.E. |
|---|---|---|
| Atropine | 8.85 | 0.98 ± 0.02[a] |
| ipratropium Br | 9.18 | 1.11 ± 0.14[a] |
| Compound (w) | 8.82 | 1.03 ± 0.08[a] |

Data are presented of mean estimates in tissue from four animals
pA$_2$: the abscissa intercept of the Schild-plot drawn
[a]Indicates slope estimates not significantly different (P > 0.05) from unity.

3. Determination of the Antagonistic Effect of Anticholinergic Agents on Charbachol Induced Bradycardia in Anesthetized Rats Intravenous administration of the cholinomimetic carbachol causes sinus bradycardia (increasing the PP cycle and RR cycle length of the ECG) in anesthetized rats. This effect, which is mediated mainly by muscarinic M$_2$ receptors, can be prevented by prior administration of anticholinergic agent. The bradycardia protective effect of Compound (w) was compared to those of atropine and ipratropium bromide in this system. Compound (w) was less active than an equimolar dose of atropine, and was slightly less active than a 10-fold lower dose of ipratropium bromide indicating that Compound (w) may have lower affinity for M$_2$ than M$_1$ or M$_3$ muscarinic receptors. Compound (aa) can be similarly evaluated.

Examination of the Time Course of the Anticholinergic Effect of Compound (w) and Compound (aa) in Electrically Stimulated Guinea Pig Trachea
Experimental Procedures:

The procedure described by Takahashi T. et al., (*Am J Respir Crit Care Med*, 150:1640-1645, 1994) was used with slight modifications.

Male Dunkin-Hartley guinea pigs (300-500 g) were exterminated; the tracheas were rapidly removed, and placed in oxygenated normal Krebs buffer solution. The epithelium was removed and the trachea was spirally cut into 15 mm long strips. Two strips from one animal were prepared and suspended between parallel stainless steel wire field electrodes in 10-ml organ baths containing buffer solution, which was continually gassed by a 95% O$_2$ and 5% CO$_2$ mixture. The tissues were allowed to equilibrate for 1 h with frequent washing, under a resting tension of 1.0 g.

Indomethacin 10$^{-5}$(M) was present throughout the studies to block the formation of endogenous prostaglandins. Before the experiment, capsaicin (10$^{-5}$M) was added and washed out 30 min after the pre-treatment to deplete endogenous tachykinins. Tissues were also pretreated with propranolol (10$^{-6}$M) 10 min before the experiment to inhibit the effects of endogenous catecholamines.

Isometric contractile responses were measured using force-displacement transducers (Experimetria, Hungary) connected to a Watanabe polygraph. A stimulator (CRS-ST-01-04, Experimetria) provided biphasic square-wave impulses with a supramaximal voltage of 40 V at source and 0.5 ms duration. Stimulations were applied at a frequency of 4 Hz for 15 sec followed by a 100 sec resting interval. After at least four stable responses of equal magnitude were obtained, the antagonist (submaximal dose) was introduced and was left in the system until the maximal effect of the drug was observed. Thereafter the test drug was washed out. Further stimulations were delivered for at least 6 additional hours or until the responses returned to about 50% of the original responses. Appropriate time controls were run in parallel for all studies.

Statistical Analysis

Contractile responses were expressed as the percentage of the own maximal contraction. The time for offset $t_{1/5}$ or $t_{1/2}$ of action was defined as the time from washout of the test antagonist to attainment of 20 or 50% recovery of cholinergic responses.

Figure 8:
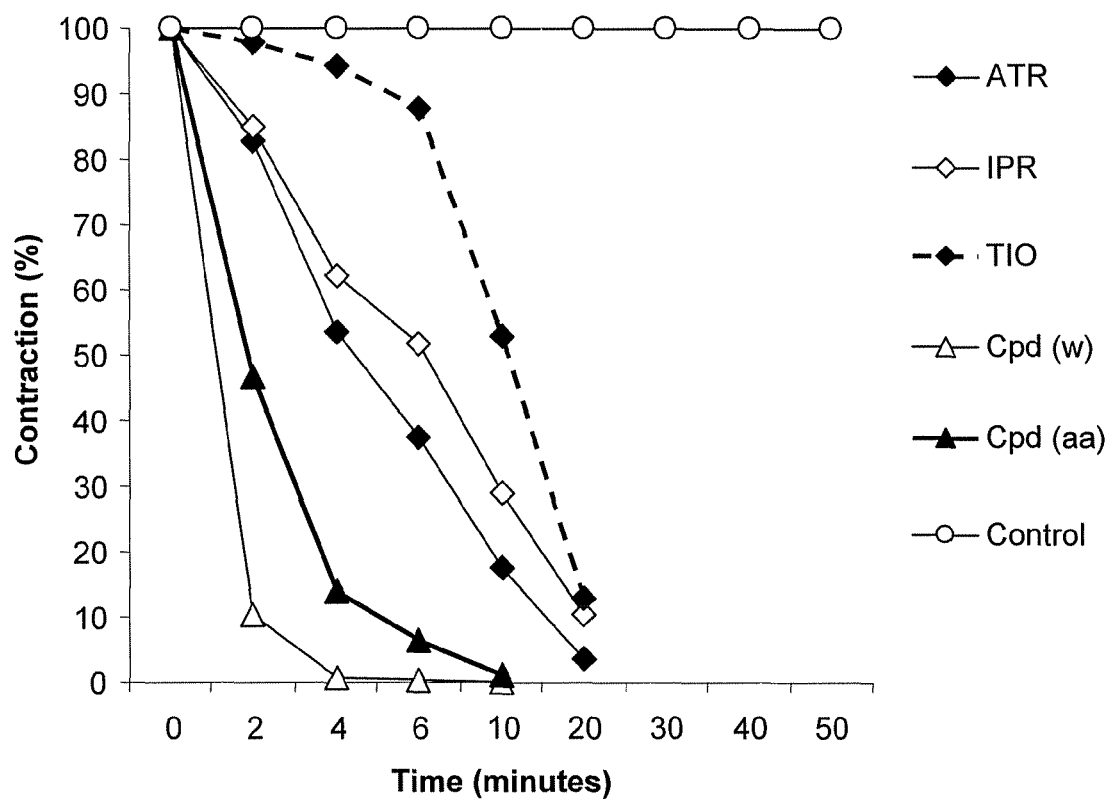
FIG. 8 is a graph showing the time course of action of different anticholinergics, including Compounds (w) and (aa), on electrically stimulated guinea pig trachea.
Figure 9:
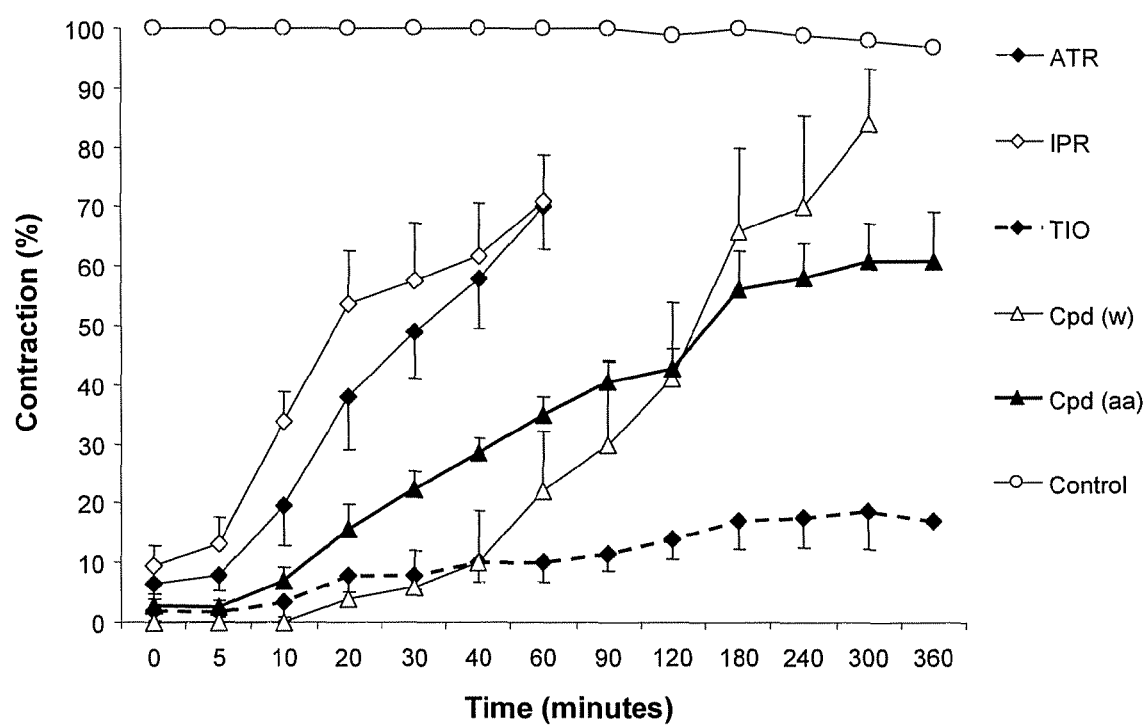
FIG. 9 is a graph showing the time course of the effect of different anticholingerics including Compounds (w) and (aa), after wash out of the test drug on electrically stimulated guinea pig trachea.

Results:

Typical tracings were obtained during the experiments. Continuous, stable, long-lasting contraction is achieved with electrical stimulation. Upon the addition of anticholinergic agents the inhibition develops with varying speed, and the inhibitory effect of the compounds last for very different periods after the washout. In FIG. 8, the time course of action of the different anticholinergic compounds is shown; calculated results are summarized in Table 11. In FIG. 9, the time course of the inhibition of the examined compounds are displayed; the results calculated from this data are summarized in Table 12.

The differences between the on and off rates of the Compounds (w) and (aa) are very notable.

TABLE 11

Time course of action of different anticholinergics in electrically stimulated guinea pig tracheal strips

| Compound | $t_{1/5}$ onset (min) | $t_{1/2}$ onset (min) |
|---|---|---|
| Atropine | 2.5 | 4.6 |
| Ipratropium Br | 3.0 | 7.0 |
| Tiotropium | 8.0 | 12 |
| Cpd (w) | 0.6 | 1.2 |
| Cpd (aa) | 0.9 | 2.0 |

TABLE 12

Time course of recovery from inhibition after washing out of different anticholinergics in electrically stimulated guinea pig tracheal strips

| Compound | $t_{1/5}$ offset (min) | $t_{1/2}$ offset (min) |
|---|---|---|
| Atropine | 10 | 31 |
| Ipratropium Br | 6.5 | 19 |
| Tiotropium | >360 | >360 |
| Cpd (w) | 60 | 130 |
| Cpd (aa) | 27 | 140 |

Investigation of the Anticholinergic Action of Compounds in Acetylcholine Induced Bronchoconstriction in Anesthetized Guinea Pigs Experimental Procedure Male Hartley guinea pigs (320±120 g) (Charles River) are housed under standard conditions. Guinea pigs are anesthetized with urethane (2 g/kg, intraperitoneally), the trachea is cannulated and the animal is respired using a small animal respiratory pump (Harvard Apparatus LTD, Kent UK). Respiratory back pressure is measured and recorded using a rodent lung function recording system (MUMED, London UK). For drug administration the right jugular vein is cannulated. Following the surgical preparation guinea pigs are allowed to stabilize for 20 minutes. Ten minutes before acetylcholine administration the animals are disconnected from the ventilator and either the vehicle (10 mg lactose) or different amounts of the drug (suspended in the same amount of vehicle) are administered intratracheally. The trachea is reconnected to the ventilator and changes in pulmonary mechanics are followed. Acetylcholine (10 µg/kg) is administered intravenously in every 10 minutes six times.

Active compounds exhibit a protective effect on the acetylcholine-induced bronchoconstriction provoked in this test.

This test is a model for asthma, chronic obstructive pulmonary disorder and other obstructive respiratory tract disorders in which the effectiveness of the compounds of formula (Ia) and (Ib) can be tested.

Test for Bronchodilatory Effect of Inhaled Test Compounds in Balb/c Mice

Female BALB/c mice, weight range 19-22 g, are obtained, for example from Charles River Laboratories (Kingston, N.C.). They receive food and water ad libitum.

Compounds for aerosol administration are prepared in sterile Dulbecco's Phosphate Buffered Saline. Mice are placed in a carousel-style, nose only, exposure chamber and allowed to inhale aerosols for five minutes, using an ICN SPAG-2 nebulizer. This nebulizer generates a mean aerosol particle size of 1.3 microns at a rate of approximately 0.25 ml/minute.

Ten minutes and 36 hours later, the mice are moved to whole body plethysmograph chambers. Bronchoconstriction is induced in the mice by administration of an 80 mg/ml methacholine (MC) aerosol into the plethysmograph chambers for 5 minutes. The mice are allowed to inhale an aerosol containing 80 mg/ml methacholine following inhalation treatment with DPBS vehicle (Dulbecco's Phosphate Buffered Saline), or 80 mg/ml methacholine following inhalation treatment with test compound. The average enhanced pause (Penh, lung resistance), corresponding to airflow resistance, is determined and statistically analyzed using Kruskal-Wallis one way ANOVA. In order to determine the baseline, saline aerosol (without methacholine) is also separately administered to the mice.

This procedure is a model for inhalation treatment of asthma, chronic obstructive pulmonary disorder and other obstructive respiratory tract disorders in which the effectiveness of the compounds of formulas (Ia) and (Ib) can be tested.

Test for Frequency of Micturition in Female Sprague-Dawley Rats

Ten female Sprague-Dawley rats having a mean weight of about 245-285 g are anesthetized with urethane (1.2 g/k, sc.). A midline incision is performed to expose the bladder and a 23G catheter is inserted into the bladder dome for the measurement of intravesical pressure. A non-stop transvesical cystometrogram, as described in *J. Pharmacological. Methods*, 15, pp. 157-167 (1986), is used, at a filling rate of 0.216 ml/min. of saline, to access the filling and voiding characteristics of the bladder. Through the continuous cystometry method thus afforded, consecutive micturition can be recorded. Test compound is given at intravenous doses after the initial baseline micturition sequence is reliably measured for approximately 12 min. From these recordings, the absolute values in maximum pressure obtained and the frequency of micturition is measured. A dose response curve illustrating the effect of test compound on the absolute micturition pressures in the range of 1-50 mg/kg can be obtained. This procedure is a model for overactive bladder (OAB) in which the compounds of formula (Ia) and (Ib) can be tested.

The following Examples illustrate numerous formulations suitable for administering the compounds of formula (Ia) and (Ib) to treat various conditions responsive to treatment with an anticholinergic agent.

In these Examples, percentages are by weight unless otherwise indicated.

EXAMPLES OF PHARMACEUTICAL FORMULATIONS

Example 1

| Tablets | per tablet |
| --- | --- |
| Compound of formula (Ia) or (Ib), e.g. Compound (cc) or (ee) or (gg) or (aa) | 400 mg |
| lactose | 140 mg |
| corn starch | 240 mg |
| polyvinylpyrrolidone | 15 mg |
| magnesium stearate | 5 mg |
| | 800 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

Example 2

| Tablets | per tablet |
| --- | --- |
| Compound of formula (Ia) or (Ib), e.g. Compound (cc) or (ee) or (gg) or (aa) | 320 mg |
| lactose | 55 mg |
| corn starch | 190 mg |
| microcrystalline cellulose | 35 mg |
| polyvinylpyrrolidone | 15 mg |
| sodium-caroxymethyl starch | 23 mg |
| magnesium stearate | 2 mg |
| | 640 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

Example 3

| Ampule solution | |
| --- | --- |
| Compound of formula (Ia) or (Ib), e.g. Compound (cc) or (ee) or (gg) or (aa) | 200 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampules which are then sterilized and sealed by fusion. The ampules contain 20 mg, 100 mg and 200 mg of active substance.

Example 4

| Metering aerosol | |
| --- | --- |
| Compound of formula (Ia) or (Ib), e.g. Compound (cc) or (ee) or (gg) or (aa) | 0.020 |
| Sorbitan trioleate | 0.1 |
| Monofluorotrichloromethane and difluorodichioromethane | 2:3 ad 100 |

The suspension is transferred into a conventional aerosol container with a metering valve. Preferably, 50 µl of suspension are delivered per spray. The active substance may also be metered in higher doses if desired (e.g. 0.08% by weight).

Example 5

| Solutions (in mg/100 ml) | |
| --- | --- |
| Compound of formula (Ia) or (Ib), e.g. Compound (cc) or (ee) or (gg) or (aa) | 1333.3 mg |
| Formoterol fumarate | 333.3 mg |
| Benzalkonium chloride | 10.0 mg |
| EDTA | 50.0 mg |
| HCl(ln) | ad pH 3.4 |

This solution may be prepared in the usual manner.

Example 6

| Powder for inhalation | |
| --- | --- |
| Compound of formula (Ia) or (Ib), e.g. Compound (cc) or (ee) or (gg) or (aa) | 24 µg |
| Formoterol fumarate | 6 µg |
| Lactose monohydrate | ad 25 mg |

The powder for inhalation is produced in the usual way by mixing the individual ingredients together.

Example 7

| Powder for inhalation | |
| --- | --- |
| Compound of formula (Ia) or (Ib), e.g. Compound (cc) or (ee) or (gg) or (aa) | 40 µg |
| Lactose monohydrate | ad 5 mg |

The powder for inhalation is produced in the usual way by mixing the individual ingredients together.

Further Formulations Obtained Analogously to Methods Known in the Art

A: Inhalable Powders

Example 8

| Ingredients | µg per capsule |
|---|---|
| Compound of formula (Ia) or (Ib), e.g. Compound (cc) or (ee) or (gg) or (aa) | 400 |
| budesonide | 200 |
| lactose | 4400 |
| Total | 5000 |

Example 9

| Ingredients | µg per capsule |
|---|---|
| Compound of formula (Ia) or (Ib), e.g. Compound (cc) or (ee) or (gg) or (aa) | 400 |
| fluticasone propionate | 125 |
| lactose | 4475 |
| Total | 5000 |

Example 10

| Ingredients | µg per capsule |
|---|---|
| Compound of formula (Ia) or (Ib), e.g. Compound (cc) or (ee) or (gg) or (aa) | 400 |
| mometasone furoate × $H_2O$ | 250 |
| lactose | 4350 |
| Total | 5000 |

Example 11

| Ingredients | µg per capsule |
|---|---|
| Compound of formula (Ia) or (Ib), e.g. Compound (cc) or (ee) or (gg) or (aa) | 400 |
| ciclesonide | 250 |
| lactose | 4350 |
| Total | 5000 |

Example 12

| Ingredients | µg per capsule |
|---|---|
| Compound of formula (Ia) or (Ib), e.g. Compound (cc) or (ee) or (gg) or (aa) | 200 |
| budesonide | 125 |
| lactose | 4675 |
| Total | 5000 |

Example 13

| Ingredients | µg per capsule |
|---|---|
| Compound of formula (Ia) or (Ib), e.g. Compound (cc) or (ee) or (gg) or (aa) | 200 |
| fluticasone propionate | 200 |
| lactose | 4600 |
| Total | 5000 |

Example 14

| Ingredients | µg per capsule |
|---|---|
| Compound of formula (Ia) or (Ib), e.g. Compound (cc) or (ee) or (gg) or (aa) | 300 |
| mometasone furoate × $H_2O$ | 250 |
| lactose | 4450 |
| Total | 5000 |

Example 15

| Ingredients | µg per capsule |
|---|---|
| Compound of formula (Ia) or (Ib), e.g. Compound (cc) or (ee) or (gg) or (aa) | 300 |
| ciclesonide | 250 |
| lactose | 4450 |
| Total | 5000 |

Example 16

| Ingredients | µg per capsule |
|---|---|
| Compound of formula (Ia) or (Ib), e.g. Compound (cc) or (ee) or (gg) or (aa) | 400 |

Example 17

| Ingredients | μg per capsule |
|---|---|
| Compound of formula (Ia) or (Ib), e.g. Compound (cc) or (ee) or (gg) or (aa) | 200 |
| ST-126 | 125 |
| lactose | 4675 |
| Total | 5000 |

Example 18

| Ingredients | μg per capsule |
|---|---|
| Compound of formula (Ia) or (Ib), e.g. Compound (cc) or (ee) or (gg) or (aa) | 400 |
| loteprednol etabonate | 200 |
| lactose | 4400 |
| Total | 5000 |

Example 19

| Ingredients | μg per capsule |
|---|---|
| Compound of formula (Ia) or (Ib), e.g. Compound (cc) or (ee) or (gg) or (aa) | 400 |
| etiprednol dichloracetate | 200 |
| lactose | 4400 |
| Total | 5000 |

Example 20

| Ingredients | μg per capsule |
|---|---|
| Compound of formula (Ia) or (Ib), e.g. Compound (cc) or (ee) or (gg) or (aa) | 400 |
| loteprednol etabonate | 125 |
| lactose | 4475 |
| Total | 5000 |

Example 21

| Ingredients | μg per capsule |
|---|---|
| Compound of formula (Ia) or (Ib), e.g. Compound (cc) or (ee) or (gg) or (aa) | 200 |
| etiprednol dichloracetate | 125 |
| lactose | 4675 |
| Total | 5000 |

Example 22

| Ingredients | μg per capsule |
|---|---|
| Compound of formula (Ia) or (Ib), e.g. Compound (cc) or (ee) or (gg) or (aa) | 400 |
| loteprednol etabonate | 200 |
| $\Delta^1$ - cortienic acid methyl ester | 200 |
| lactose | 4200 |
| Total | 5000 |

Example 23

| Ingredients | μg per capsule |
|---|---|
| Compound of formula (Ia) or (Ib), e.g. Compound (cc) or (ee) or (gg) or (aa) | 400 |
| loteprednol etabonate | 200 |
| $\Delta^1$ - cortienic acid | 200 |
| lactose | 4200 |
| Total | 5000 |

Example 24

| Ingredients | μg per capsule |
|---|---|
| Compound of formula (Ia) or (Ib), e.g. Compound (cc) or (ee) or (gg) or (aa) | 400 |
| loteprednol etabonate | 125 |
| $\Delta^1$ - cortienic acid or $\Delta^1$ - cortienic acid methyl ester | 125 |
| lactose | 4350 |
| Total | 5000 |

-continued

| Ingredients | μg per capsule |
|---|---|
| ST-126 | 250 |
| lactose | 4350 |
| Total | 5000 |

Example 25

| Ingredients | μg per capsule |
|---|---|
| Compound of formula (Ia) or (Ib), e.g. Compound (cc) or (ee) or (gg) or (aa) | 200 |
| loteprednol etabonate | 125 |
| Δ¹ - cortienic acid or Δ¹ - cortienic acid methyl ester | 125 |
| lactose | 4550 |
| Total | 5000 |

B. Propellant-Containing Aerosols for Inhalation (wherein TG 134a is 1,1,1,2-tetrafluoroethane and TG 227 is 1,1,1,2,3,3,3-heptafluoropropane)

Example 26

Suspension Aerosol

| Ingredients | % by weight |
|---|---|
| Compound of formula (Ia) or (Ib), e.g. Compound (cc) or (ee) or (gg) or (aa) | 0.2 |
| budesonide | 0.4 |
| soya lecithin | 0.2 |
| TG 134a:TG227 (2:3) | to 100 |

Example 27

Suspension Aerosol

| Ingredients | % by weight |
|---|---|
| Compound of formula (Ia) or (Ib), e.g. Compound (cc) or (ee) or (gg) or (aa) | 0.08 |
| fluticasone propionate | 0.3 |
| isopropyl myristate | 0.1 |
| TG 227 | to 100 |

Example 28

Suspension Aerosol

| Ingredients | % by weight |
|---|---|
| Compound of formula (Ia) or (Ib), e.g. Compound (cc) or (ee) or (gg) or (aa) | 0.08 |
| mometasone furoate × H$_2$O | 0.6 |
| isopropyl myristate | 0.1 |
| TG 227 | to 100 |

Example 29

Suspension Aerosol

| Ingredients | % by weight |
|---|---|
| Compound of formula (Ia) or (Ib), e.g. Compound (cc) or (ee) or (gg) or (aa) | 0.08 |
| ciclesonide | 0.4 |
| isopropyl myristate | 0.1 |
| TG 134a:TG227 (2:3) | to 100 |

Example 30

Suspension Aerosol

| Ingredients | % by weight |
|---|---|
| Compound of formula (Ia) or (Ib), e.g. Compound (cc) or (ee) or (gg) or (aa) | 0.17 |
| ciclesonide | 0.4 |
| absolute ethanol | 0.5 |
| isopropyl myristate | 0.1 |
| TG 134a:TG227 (2:3) | to 100 |

Example 31

Solution Aerosol

| Ingredients | % by weight |
|---|---|
| Compound of formula (Ia) or (Ib), e.g. Compound (cc) or (ee) or (gg) or (aa) | 0.17 |
| fluticasone propionate | 0.2 |
| absolute ethanol | 0.5 |
| isopropyl myristate | 0.1 |
| TG 134a:TG227 (2:3) | to 100 |

Example 32

Solution Aerosol

| Ingredients | % by weight |
|---|---|
| Compound of formula (Ia) or (Ib), e.g. Compound (cc) or (ee) or (gg) or (aa) | 0.17 |
| mometasone furoate × H$_2$O | 0.6 |
| absolute ethanol | 0.5 |
| isopropyl myristate | 0.1 |
| TG 134a:TG227 (2:3) | to 100 |

Example 33

Solution Aerosol

| Ingredients | % by weight |
| --- | --- |
| Compound of formula (Ia) or (Ib), e.g. Compound (cc) or (ee) or (gg) or (aa) | 0.17 |
| ciclesonide | 0.4 |
| absolute ethanol | 0.5 |
| isopropyl myristate | 0.1 |
| TG 134a:TG227 (2:3) | to 100 |

Example 34

Solution Aerosol

| Ingredients | % by weight |
| --- | --- |
| Compound of formula (Ia) or (Ib), e.g. Compound (cc) or (ee) or (gg) or (aa) | 0.17 |
| ST-126 | 0.6 |
| absolute ethanol | 0.5 |
| isopropyl myristate | 0.1 |
| TG 134a:TG227 (2:3) | to 100 |

Example 35

Solution Aerosol

| Ingredients | % by weight |
| --- | --- |
| Compound of formula (Ia) or (Ib), e.g. Compound (cc) or (ee) or (gg) or (aa) | 0.17 |
| ST-126 | 0.4 |
| absolute ethanol | 0.5 |
| isopropyl myristate | 0.1 |
| TG 134a:TG227 (2:3) | to 100 |

Example 36

| Ingredients | % by weight |
| --- | --- |
| Compound of formula (Ia) or (Ib), e.g. Compound (cc) or (ee) or (gg) or (aa) | 0.2 |
| loteprednol etabonate | 0.4 |
| soya lecithin | 0.2 |
| TG 134a:TG227 (2:3) | to 100 |

Example 37

| Ingredients | % by weight |
| --- | --- |
| Compound of formula (Ia) or (Ib), e.g. Compound (cc) or (ee) or (gg) or (aa) | 0.08 |
| loteprednol etabonate | 0.3 |
| isopropyl myristate | 0.1 |
| TG 227 | to 100 |

Example 38

| Ingredients | % by weight |
| --- | --- |
| Compound of formula (Ia) or (Ib), e.g. Compound (cc) or (ee) or (gg) or (aa) | 0.08 |
| etiprednol dichloracetate | 0.4 |
| isopropyl myristate | 0.1 |
| TG 227 | to 100 |

Example 39

| Ingredients | % by weight |
| --- | --- |
| Compound of formula (Ia) or (Ib), e.g. Compound (cc) or (ee) or (gg) or (aa) | 0.08 |
| loteprednol etabonate | 0.4 |
| isopropyl myristate | 0.1 |
| TG 134a:TG227 (2:3) | to 100 |

Example 40

| Ingredients | % by weight |
| --- | --- |
| Compound of formula (Ia) or (Ib), e.g. Compound (cc) or (ee) or (gg) or (aa) | 0.17 |
| loteprednol etabonate | 0.4 |
| absolute ethanol | 0.5 |
| isopropyl myristate | 0.1 |
| TG 134a:TG227 (2:3) | to 100 |

Example 41

| Ingredients | % by weight |
| --- | --- |
| Compound of formula (Ia) or (Ib), e.g. Compound (cc) or (ee) or (gg) or (aa) | 0.2 |
| loteprednol etabonate | 0.4 |
| $\Delta^1$-cortienic acid or $\Delta^1$-cortienic acid methyl ester | 0.4 |
| soya lecithin | 0.2 |
| TG134a:TG227 (2:3) | to 100 |

Example 42

| Ingredients | % by weight |
| --- | --- |
| Compound of formula (Ia) or (Ib), e.g. Compound (cc) or (ee) or (gg) or (aa) | 0.08 |
| loteprednol etabonate | 0.3 |
| $\Delta^1$ - cortienic acid or $\Delta^1$ - cortienic acid methyl ester | 0.3 |
| isopropyl myristate | 0.1 |
| TG227 | to 100 |

Example 43

| Ingredients | % by weight |
| --- | --- |
| Compound of formula (Ia) or (Ib), e.g. Compound (cc) or (ee) or (gg) or (aa) | 0.16 |
| loteprednol etabonate | 0.4 |
| $\Delta^1$ - cortienic acid or $\Delta^1$ - cortienic acid methyl ester | 0.4 |
| isopropyl myristate | 0.1 |
| TG 227 | to 100 |

Example 44

| Ingredients | % by weight |
| --- | --- |
| Compound of formula (Ia) or (Ib), e.g. Compound (cc) or (ee) or (gg) or (aa) | 0.08 |
| loteprednol etabonate | 0.4 |
| $\Delta^1$ - cortienic acid or $\Delta^1$ - cortienic acid methyl ester | 0.4 |
| isopropyl myristate | 0.1 |
| TG134a:TG227 (2:3) | to 100 |

Example 45

| Ingredients | % by weight |
| --- | --- |
| Compound of formula (Ia) or (Ib), e.g. Compound (cc) or (ee) or (gg) or (aa) | 0.17 |
| loteprednol etabonate | 0.4 |
| $\Delta^1$ - cortienic acid or $\Delta^1$ - cortienic acid methyl ester | 0.4 |
| absolute ethanol | 0.5 |
| isopropyl myristate | 0.1 |
| TG134a:TG227 (2:3) | to 100 |

C. Ophthalmic Formulations

Example 46

| EYE DROPS | |
| --- | --- |
| Compound of formula (Ia) or (Ib), e.g. Compound (cc) or (ee) or (gg) or (aa) | 0.20% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

Example 47

| EYE DROPS | |
| --- | --- |
| Compound of formula (Ia) or (Ib), e.g. Compound (cc) or (ee) or (gg) or (aa) | 0.16% w/v |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

Example 48

| EYE DROPS | |
| --- | --- |
| Compound of formula (Ia) or (Ib), e.g. Compound (cc) or (ee) or (gg) or (aa) | 0.14% w/v |
| Povidone | 0.6% w/v |
| Benzalkonium chloride | 0.02% w/v |
| Sodium edetate U.S.P. | 0.10% w/v |
| Glycerin U.S.P. | 2.5% w/v |
| Tyloxapol U.S.P. | 3.0% w/v |
| Sodium chloride | 0.3% w/v |
| Sodium γ-aminobutyrate | 1.0% w/v |
| Sterile distilled water | q.s. 100 volumes |

The ingredients listed above are combined, then the pH is checked and, if necessary, adjusted to 5.0-5.5 by basifying with sodium hydroxide or acidifying with hydrochloric acid.

Yet other compositions of the invention can be conveniently formulated using known techniques.

While this description has been couched in terms of various preferred or exemplary embodiments, the skilled artisan will appreciate that various modifications, substitutions, omissions and changes may be made without departing from the spirit thereof. Accordingly, it is intended that the scope of the foregoing be limited only by the broadest statements herein and by the scope of the following claims, including equivalents thereof.

What is claimed is:

1. A compound having the formula:

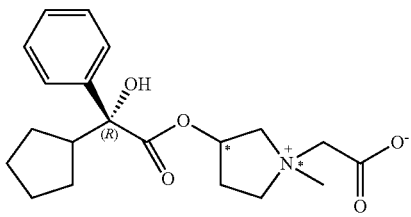

wherein each asterisk marks a chiral center; said compound having the R, S or RS stereoisomeric configuration at each chiral center unless specified otherwise, or being a mixture thereof.

2. The compound which is:
(bb) (±) 3-(2-cyclopentyl-2-phenyl-2-hydroxyacetoxy)-1-(carboxymethyl)-1-methylpyrrolidinium inner salt;
(cc) (2R) 3-(2-cyclopentyl-2-phenyl-2-hydroxyacetoxy)-1-(carboxymethyl)-1-methylpyrrolidinium inner salt;
(dd) (2R,1'R,3'R) 3-(2-cyclopentyl-2-phenyl-2-hydroxyacetoxy)-1-(carboxymethyl)-1-methylpyrrolidinium inner salt;
(ee) (2R,1'S,3'R) 3-(2-cyclopentyl-2-phenyl-2-hydroxyacetoxy)-1-(carboxymethyl)-1-methylpyrrolidinium inner salt;
(ff) (2R,1'R,3'S) 3-(2-cyclopentyl-2-phenyl-2-hydroxyacetoxy)-1-(carboxymethyl)-1-methylpyrrolidinium inner salt;
(gg) (2R,1'S,3'S) 3-(2-cyclopentyl-2-phenyl-2-hydroxyacetoxy)-1-(carboxymethyl)-1-methylpyrrolidinium inner salt;
(hh) (2S,1'R,3'R) 3-(2-cyclopentyl-2-phenyl-2-hydroxyacetoxy)-1-(carboxymethyl)-1-methylpyrrolidinium inner salt;
(ii) (2S,1'S,3'R) 3-(2-cyclopentyl-2-phenyl-2-hydroxyacetoxy)-1-(carboxymethyl)-1-methylpyrrolidinium inner salt;
(jj) (2S,1'R,3'S) 3-(2-cyclopentyl-2-phenyl-2-hydroxyacetoxy)-1-(carboxymethyl)-1-methylpyrrolidinium inner salt; or
(kk) (2S,1'S,3'S) 3-(2-cyclopentyl-2-phenyl-2-hydroxyacetoxy)-1-(carboxymethyl)-1-methylpyrrolidinium inner salt.

3. The compound which is:
(bb) (±) 3-(2-cyclopentyl-2-phenyl-2-hydroxyacetoxy)-1-(carboxymethyl)-1-methylpyrrolidinium inner salt; or
(cc) (2R) 3-(2-cyclopentyl-2-phenyl-2-hydroxyacetoxy)-1-(carboxymethyl)-1-methylpyrrolidinium inner salt.

4. A pharmaceutical composition comprising an anticholinergically effective amount of a compound as claimed in claim 1 and a non-toxic pharmaceutically acceptable carrier therefor.

5. A pharmaceutical composition comprising an anticholinergically effective amount of a compound as claimed in claim 3, and a non-toxic pharmaceutically acceptable carrier therefor.

6. A pharmaceutical composition comprising an anticholinergically effective amount of a compound as claimed in claim 2 and a non-toxic pharmaceutically acceptable carrier therefor.

* * * * *